(12) United States Patent
Schricker et al.

(10) Patent No.: US 8,592,372 B2
(45) Date of Patent: Nov. 26, 2013

(54) PHARMACEUTICAL COMPOSITION AND METHOD OF USE TO IMPROVE ORGAN FUNCTION

(75) Inventors: Thomas P. S. Schricker, Baie d'Urfe (CA); Ralph Latterman, Montreal (CA); Mazen Hassanain, Verdun (CA); Peter Metrakos, Montreal (CA)

(73) Assignee: King Saud University Liver Disease, Riyadh (SA)

(*) Notice: Subject to any disclaimer, the term of this patent is extended or adjusted under 35 U.S.C. 154(b) by 0 days.

(21) Appl. No.: 13/171,597

(22) Filed: Jun. 29, 2011

(65) Prior Publication Data
US 2011/0319323 A1 Dec. 29, 2011

Related U.S. Application Data

(60) Provisional application No. 61/359,496, filed on Jun. 29, 2010, provisional application No. 61/406,293, filed on Oct. 25, 2010.

(51) Int. Cl.
*A61P 3/08* (2006.01)
*A61K 38/00* (2006.01)
*A61K 47/36* (2006.01)

(52) U.S. Cl.
USPC .......................... 514/6.8; 514/777

(58) Field of Classification Search
USPC ......................................................... 514/6.8
See application file for complete search history.

(56) References Cited

U.S. PATENT DOCUMENTS 5,840,770 A * 11/1998 Hill ................................ 514/5.9

OTHER PUBLICATIONS

Leslie et al., British Med. Journal, 13-43-1344, 1978.*
Luksch et al., Daibetologia, 44: 95-103, 2001.*
Albacker et al., Ann Thorac Surg 86: 20-27, 2008.*
Lu et al., Mol. Cancer Res 4: 221-233, 2006.*
Abedini, Sadollah et al., Inflammation in Renal Transplantation., Clin J Am Soc Nephrol 4: 1246-1254, 2009.
Barton, M et al., Exploring beyond viral load testing for EBV lymphoproliferation: Role of serum IL-6 and IgE assays as adjunctive tests., Pediatr Transplantation 2010: 14: 852-858.
Dahle, Dag Olav et al., Inflammation-associated graft loss in renal transplant recipients., Nephrol Dial Transplant (2011) 0: 1-6.
Ioannidou, Effie et al., Elevated Serum Interleukin-6 (IL-6) in Solid-Organ Transplant Recipients is Positively Associated With Tissue Destruction and IL-6 Gene Expression in the Periodontium., J Periodontol • Nov. 2006.
Rossi, J-F et al., Optimizing the use of anti-interleukin-6 monoclonal antibody with dexamethasone and 140 mg/m2 of melphalan in multiple myeloma: results of a pilot study including biological aspects., Bone Marrow Transplantation (2005) 36, 771-779.
Albacker et al., "High dose insulin therapy attenuates systemic inflammatrory response in coronary artery bypass grafting patients", Ann. Thorac. Surg. , 86 pp. 20-27, Jul. 2008.
Finfer et al., "Intensive versus conventional glucose control in critically ILL patients", N.E.J.M., 360, pp. 1283-1297, Mar. 2009.
Svedjeholm et al, "Dopamine and high-dose insulin infusion (glucose-insulin-potassium) after a cardiac operation: Effects on myocardial metabolism", Ann. Thorac. Surg., 51, pp. 262-270, Feb. 1991.
Zuurbier et al., "Perioperative hyperinsulinaemic normoglycaemia clamp causes hypolipidaemia after coronary artery surgery", Br. J. Anaesth,, 100, pp. 442-450, Feb. 2008.
Sato et al., "Perioperative glucose and insulin administration while maintaining normoglycemia (GIN therapy) in patents undergoing major liver resection", Anesth. Analg. 110, pp. 1711-1718, Jun. 1, 2010.

* cited by examiner

*Primary Examiner* — Gyan Chandra
(74) *Attorney, Agent, or Firm* — Benoît & Côté Inc.

(57) ABSTRACT

The present document describes a pharmaceutical composition as well as methods to improve organ function using a high dose of insulin and maintaining normal glycemia. Methods of intensive insulin therapy using the pharmaceutical composition are also described.

12 Claims, 20 Drawing Sheets a) Initial liver glycogen    b) Post-hepatectomy liver glycogen

Liver function score (Schindl et al)

PHARMACEUTICAL COMPOSITION AND METHOD OF USE TO IMPROVE ORGAN FUNCTION

BACKGROUND (a) Field

The subject matter disclosed generally relates to a pharmaceutical compositions and methods to improve organ function, and more specifically to pharmaceutical compositions and methods to improve organ function with high doses of insulin.

(b) Related Prior Art

Evidence suggests that variability of glycemia, rather than the absolute blood glucose value, are associated with outcomes during, and especially after, surgery. Although hyperglycemia is a well-recognized risk factor in the context of cardiac surgery, the relevance of pre-, peri-, and post-operative glycemic control for patients undergoing major noncardiac operations, such as major surgical resections and organ transplantation from either live or cadaveric donors, has received little attention as hyperglycemia is a reflection of heightened inflammatory response to stress. There is a need for a treatment that targets both inflammatory response and stress More recent attempts to achieve tight glucose control in critical patients were associated with a significant incidence of hypoglycaemia. For example, the NICE-SUGAR trial (Finfer S, Chittock D R, Su S Y, et al. *NEJM* 2009; 360:1283-97), a randomized controlled trial involving more than 6000 patients comparing intensive (target blood glucose 81-108 mg/dL) versus conventional (target blood glucose≤180 mg/dL) glucose control, reported a high incidence of severe hypoglycaemia and increased mortality in patients administered with intensive insulin therapy. Therefore, tight glucose control cannot be achieved using the insulin sliding scale together with the occasional measurements of blood glucose. Furthermore, the use of intensive insulin therapy placed critically ill patients with sepsis (VISEP trial) at an increased risk for serious adverse events related to hypoglycaemia. Thus, the benefits of strict glycemic control in the ICU have not been established by either the VISEP or NICE-SUGAR trials. Therefore, there is a need for improved treatment modalities for the control of glycemia Liver disease related to acute systemic inflammation as in brain-dead organ donors and acute ischemia/reperfusion injury for organ transplants where the inflammatory status can affect graft and recipient survival Liver disease related to chronic systemic inflammation example of chronic liver disease from hepatitis C viral infection, and non-alcholic fatty liver disease, where liver disease is a part of a systemic inflammation and insulin resistance, increase mobilization of free fatty acid, increase liver steatosis, diminishing liver glycogen content and ending with liver fibrosis, cirrhosis and liver cancer.

There is therefore a need for pharmaceutical compositions and methods to eliminate or at least reduce the levels of pro-inflammatory markers prior to, during, and following surgical intervention.

There is therefore a need for a technique that can achieve a tight glucose control and avoid hypoglycemia in critically ill patients or surgical patients.

There is therefore a need for pharmaceutical compositions and method to eliminate or at least reduce the levels of pro-inflammatory markers associated both acute and chronic inflammatory status e.g. brain death, surgical stress, insulin resistance, fatty liver diseases, and/or chronic viral liver infections.

SUMMARY

The hormone insulin is an anabolic hormone that offers potent anti-inflammatory properties to the patient and also a potent stimulus of hepatocyte proliferation and prevention of exaggerated apoptosis. Therefore, a goal of the glucose and insulin normoglycemic (GIN) therapy as described herein is to provide high levels of insulin to a human subject and leverage these properties of insulin for therapeutic use. To compensate for the potentially dangerous levels of insulin used during the treatment, glucose is provided to ensure the patient does not reach hypoglycaemia and suffer complications associated with hypoglycaemia such as death.

According to an embodiment, there is provided a pharmaceutical composition to improve organ function that includes
from about 2200 µg to about 22 500 µg of insulin;
at least one salt;
a pharmaceutically acceptable carrier.

The salt may be 20 mmol/L KCl.

The composition may further comprise at least one excipients.

The composition may further comprise a preservative agent, and the preservative agent may be a phenol, a cresol, a methyl parahydroxybenzoate, a propyl parahydroxybenzoate, a butyl parahydroxybenzoate, methyl paraben and mixtures thereof. The cresol may be m-cresol. The methyl parahydroxybenzoate may be methyl p-hydroxybenzoate. The phenol may be phenol and/or alkyl phenol.

The composition may further comprise an active ingredient, and the active ingredient. The active ingredient may be an anti-inflammatory compound, and/or a glucacon-like protein or peptide analog. The anti-inflammatory compound may be at least one of methyl salicilate, salicylic acid, aspirin, indometacin, diclofenac, ibuprofene, ketoprofen, naproxen, ketorolac, mefenamic acid, piroxicam, meloxicam, celecoxib, rofecoxib, parecoxib, etocoxib, nimesulide, and codein. The glucacon-like protein or peptide analog may be exendin-4.

The insulin may be of human, bovine, or porcine origin.

The insulin may be short-acting insulin or long acting insulin.

The composition may comprise zinc.

The insulin may be a zinc containing insulin.

The insulin may be recombinant insulin, research grade insulin, pharmaceutical grade insulin, or generic insulin. The recombinant insulin may comprise amino-acid modifications. The recombinant insulin may comprise amino-acid additions. The insulin may be conjugated to a carrier protein, and the carrier protein may be a serum albumin.

According to another embodiment, there is provided a method of improving organ function comprising:
administering to a subject in need thereof a high dose of insulin and a dose of dextrose sufficient to avoid hypoglycemia for a time sufficient for improving organ function,
wherein the starting blood glucose level of the subject prior to administering may be from about 4 mmol/L and about 6 mmol/L, and
wherein the administering may be for maintaining a target blood glucose level of the subject from about 3.5 mmol/L to less than about 8.5 mmol/L.

The rate of administration of the high dose of insulin may be from about 1 mU/kg/min to about 5 mU/kg/min.

The dose of dextrose is provided from a 20% w/v dextrose solution, and the rate of administration of the dose of dextrose may be adjusted to maintain normoglycemia.

The rate of administration of the dose of dextrose may be 40 ml/hour.

The starting blood glucose level may be from about 6 mmol/L to about 20 mmol/L, administration of the high dose of insulin and the dose of dextrose may be sustained until the target blood glucose level may be from about 4 mmol/L and 6 mmol/L.

The dose of dextrose may be provided from a 20% w/v dextrose solution, and the rate of administration of the dose of dextrose may be 20 ml/hour.

When the starting blood glucose level is from about 12 mmol/L or more, administration of the high dose of an insulin may be started prior to administering of the dose of dextrose, and the administration of the high dose of insulin is sustained until the target blood glucose level is from about 4 mmol/L to about 6 mmol/L.

When the starting blood glucose level is from about 3 mmol/L or less, administration of the dose of dextrose may be started prior to administering of the high dose of insulin, a bolus of dextrose may be administered to the subject, and the administration of the dose of dextrose may be sustained until the target blood glucose level is from about 4 mmol/L to about 6 mmol/L.

When the starting blood glucose level is from about 3.1 mmol/L to about 4.5 mmol/L, administration of the dose of dextrose may be started prior to administering of the of high dose of an insulin, and the administration of the dose of dextrose may be sustained until the target blood glucose level is from about 4 mmol/L to about 6 mmol/L.

When the target blood glucose level is from about 3 mmol/L or less, the rate of administration of the dose of dextrose may be increased, a bolus of dextrose may be administered to the subject, and the administration of the dose of dextrose may be sustained until the target blood glucose level is from about 4 mmol/L to about 6 mmol/L.

The increase in the rate of administration of the dose of dextrose may be by 20 ml/hour.

The bolus may be 20 ml of a 20% w/v dextrose solution.

When the target blood glucose level is from about 3.4 mmol/L or less, a rate of administration of said dose of dextrose may be increased, a bolus of dextrose may be administered to the subject, and the administration of the dose of dextrose may be sustained until said target blood glucose level is from about 4 mmol/L to about 6 mmol/L.

The increase in the rate of administration of the dose of dextrose may be by 30 ml/hour.

The bolus may be 20 ml of a 20% w/v dextrose solution.

The target blood glucose level may be from about 3.5 mmol/L to about 3.9 mmol/L, a rate of administration of the dose of dextrose may be increased, a bolus of dextrose may be administered to the subject, and the administration of the dose of dextrose may be sustained until the target blood glucose level is from about 4 mmol/L to about 6 mmol/L.

The increase in the rate of administration of the dose of dextrose may be by 20 ml/hour.

The bolus may be 10 ml of a 20% w/v dextrose solution.

When the target blood glucose level is from about 4.0 mmol/L to about 4.3 mmol/L, a rate of administration of the dose of dextrose may be increased, and the administration of the dose of dextrose may be sustained until the target blood glucose level is from about 4 mmol/L to about 6 mmol/L.

The increase in the rate of administration of the dose of dextrose may be by 20 ml/hour.

When the target blood glucose level is from about 4.3 mmol/L to about 4.7 mmol/L, a rate of administration of the dose of dextrose may be increased, and the administration of the dose of dextrose may be sustained until the target blood glucose level is from about 4 mmol/L to about 6 mmol/L.

The increase in the rate of administration of the dose of dextrose may be by 10 ml/hour.

When the target blood glucose level is from about 4.8 mmol/L to about 5.4 mmol/L, a rate of administration of the high dose of an insulin and said dose of dextrose may be sustained. The target blood glucose level may be from about 4.6 mmol/L to about 5.5 mmol/L, the rate of administration of the high dose of an insulin and the dose of dextrose may be sustained.

The target blood glucose level may be from about 3.1 mmol/L to about 4.5 mmol/L, the rate of administration of the dose of dextrose may be increased, and the administration of the dose of dextrose may be sustained until the target blood glucose level is from about 4 mmol/L and 6 mmol/L.

The increase in the rate of administration of the dose of dextrose may be by 20 ml/hour.

When the target blood glucose level is from about 5.6 mmol/L to about 6.4 mmol/L, the rate of administration of the dose of dextrose may be decreased.

The decrease in the rate of administration of the dose of dextrose may be by 20 ml/hour.

When the target blood glucose level is from about 5.5 mmol/L to about 5.9 mmol/L, a rate of administration of the dose of dextrose may be decreased.

The decrease in the rate of administration of the dose of dextrose may be by 15 ml/hour.

When the target blood glucose level is from about 6 mmol/L to about 6.4 mmol/L, a rate of administration of the dose of dextrose may be decreased.

The decrease in the rate of administration of the dose of dextrose may be by 30 ml/hour.

When the target blood glucose level is from about 6.5 mmol/L or more, the rate of administration of the dose of dextrose may be decreased.

The decrease in the rate of administration of the dose of dextrose may be by 40 ml/hour.

The time sufficient may be about 8 hours. The time sufficient may be about 8 hours, twice a week. The time sufficient may be about 8 hours, twice a week for 24 weeks.

The target blood sugar level may be from about 4.6 mmol/L to about 5.5 mmol/L.

The target blood glucose level may be measured 10 minutes after starting of the administering.

The target blood glucose level may be measured every 60 minutes until the end of the administering.

The target blood glucose level may be measured every 10 minutes after starting of the administering.

The method may be for the treatment of a condition chosen from sepsis, a severe sepsis, a liver requiring surgical resection, a resected liver, an organ transplant, a liver condition, insulin-resistance syndrome, a metabolic syndrome caused by insulin-resistance, a cancer, a brain death, a major surgery, a coronary heart disease, a cardiomyopathy, a cardiovascular disease, ischaemic heart disease, heart failure, hypertensive heart disease, inflammatory heart disease, and a valvular heart disease and an oxidative stress associated disease.

The treatment may be for a coronary artery bypass grafting.

The organ transplant may be chosen from heart transplant, liver transplant, kidney transplant, pancreas transplant, a β-islet cell transplant, a lung transplant, a bone marrow transplant, an intestine transplant or combinations thereof.

The β-islet cell transplant may be for a diabetic patient.

The method of treatment may be for a transplant donor, a transplant recipient, or both a transplant donor and a transplant recipient.

The donor may be one of a live donor, a deceased donor, a brain dead donor, a potential cadaveric donor.

The cancer may be a cancer of the liver, a cancer of the pancreas, a cancer of the bile ducts, a cancer of the kidney, a cancer that originated in the colorectum and which then metastasized to the liver, a cancer that originated in the breast and which then metastasized to the liver, or a combination thereof.

The oxidative stress associated disease may be Alzheimer's disease, Parkinson's disease, Parkinson's disease with dementia with Lewy body, Huntington's disease, multiple system atrophy (MSA), progressive supranuclear palsy (PSA), corticobasal degeneration (CBD), frontotemporal lobe degeneration, atherosclerosis, heart failure, myocardial infarction, and chronic fatigue.

The liver condition may be alcoholic fatty liver, non-alcoholic fatty liver, alcoholic steatohepatitis, non-alcoholic steatohepatitis, steatohepatitis with fibrosis, early fibrosis, fibrosis, cirrhosis, hepatitis B-infection, hepatitis B-infection with HIV co-infection, hepatitis C-infection, hepatitis C-infection with HIV co-infection, a chronic liver disease, acute liver failure, chronic liver failure, acute fulminant hepatitis and hepatic failure.

The method may be at least one of a pre-operative treatment, a peri-operative treatment, a post-operative treatment, a long term intermittent treatment and a long term continuous treatment or combinations thereof.

The pre-operative treatment may further comprise a pre-operative antibiotic treatment.

The pre-operative antibiotic treatment may comprise an Ampicillin® treatment and a Cephtriaxone® treatment.

According to another embodiment, there is provided a method of intensive insulin therapy comprising:
 a) performing a pre-insulin therapy blood test on a subject;
 b) treating the subject with an intensive insulin therapy according to a method of the present invention; and
 c) performing a post-insulin therapy blood test on the subject.

The pre-insulin therapy blood test may comprise the measurement of at least one of a HbA1C level, C-peptide level, albumin level, a complete blood count, a pre-albumin level, an electrolytes level, renal function, a C-reactive protein (CRP) level and a free cortisol level.

When the intensive insulin therapy is for a pre-operative treatment, the pre-insulin therapy blood test may comprise measurement of at least one of, an albumin level, arterial blood gas (ABG), a lactic acid level, an insulin level, a glucagon level, a free fatty acid (FFA) level, a TNF alpha, an IL-1 beta level, an IL-6 level, an IL-8 level, a complete blood count, a pre-albumin level, an electrolytes level, renal function, a C-reactive protein (CRP) level and free cortisol.

When the intensive insulin therapy is for a pre-operative treatment, a peri-operative treatment, a post-operative treatment, or combinations thereof, the post-insulin therapy blood test may comprise measurement of at least one of a arterial blood gas (ABG), a lactic acid level, an insulin level, a glucagon level, a free fatty acid (FFA) level, a TNF alpha, an IL-1 beta level, an IL-6 level, and an IL-8 level.

The post-insulin therapy blood test may be performed at the arrival of the subject in a post anesthesia care unit, at 4 hours after surgery, or both.

When the intensive insulin therapy is for a pre-operative treatment, a peri-operative treatment, a post-operative treatment, sepsis, cardiogenic shock, liver failure, uncontrolled blood sugar, or combinations thereof, the post-insulin therapy blood test may comprise measurement of at least one of a complete blood count, a pre-albumin level, an electrolytes level, renal function, a C-reactive protein (CRP) level and free cortisol.

The post-insulin therapy blood test may be performed at 24 hours after surgery, at 48 hours after surgery, 7 days after surgery, or combinations thereof.

When the intensive insulin therapy is for a pre-operative treatment, a peri-operative treatment, a post-operative treatment, or combinations thereof, the post-insulin therapy blood test may comprise measurement of at least one of an arterial blood gas (ABG), a lactic acid level, an insulin level, a glucagon level, a free fatty acid (FFA) level, a TNF alpha, an IL-1 beta level, an IL-6 level, an IL-8 level, a complete blood count, a pre-albumin level, an electrolytes level, renal function, a C-reactive protein (CRP) level and free cortisol.

The post-insulin therapy blood test may be performed at 72 hours after surgery.

When the intensive insulin therapy is for a pre-operative treatment, a peri-operative treatment, a post-operative treatment, or combinations thereof, the post-insulin therapy blood test comprises measurement of at least one of a HbA1C level, a C-peptide level, an insulin level, and an albumin level.

The post-insulin therapy blood test may comprise measurement of the level of at least one of IL-2, IL-4, IL-6, IL-10, IL-1b, IL-1, TNF-α, TNF-β, MCP-1, CCL2/MCP-1, CCL3/MIP-1a, CCL4/MIP-1β, TGF-β1, MIP-1a, ICAM-1, CXCL3/KC, CXCL1/GRO-α, CXCL2/GRO-β, CXCL10/IP-10, and INF-γ.

The post-insulin therapy blood test may be at 6 hours, 12 hours, 24 hours, 48 hours, and 7 days post treatment.

According to another embodiment, there is provided a use of a method for improving organ function according to the method of the present invention for the treatment of an intensive care cardiac patient.

The cardiac patient may be suffering from a condition chosen from Coronary heart disease, a cardiomyopathy, a cardiovascular disease, ischaemic heart disease, heart failure, hypertensive heart disease, inflammatory heart disease, and a valvular heart disease.

The cardiac patient may be a heart transplant patient.

The method of improving of organ function may be used prior to, during, and/or after organ transplant.

The following terms are defined below.

The term "insulin" is intended to mean the hormone that is central to regulating the energy and glucose metabolism in the body. The insulin used in the present invention is used in amounts higher than for normal blood glucose regulation, and tied to body weight rather than to blood sugar level, and it may be of any origin (animal or recombinant) and of any composition, so long as it is active as an insulin hormone.

The term "pharmaceutically acceptable carrier" is intended to mean a preservative solution, a saline solution, an isotonic (about 0.9%) saline solution, or about a 5% albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

BRIEF DESCRIPTION OF THE DRAWINGS

Further features and advantages of the present disclosure will become apparent from the following detailed description, taken in combination with the appended drawings, in which.

Figure 1:
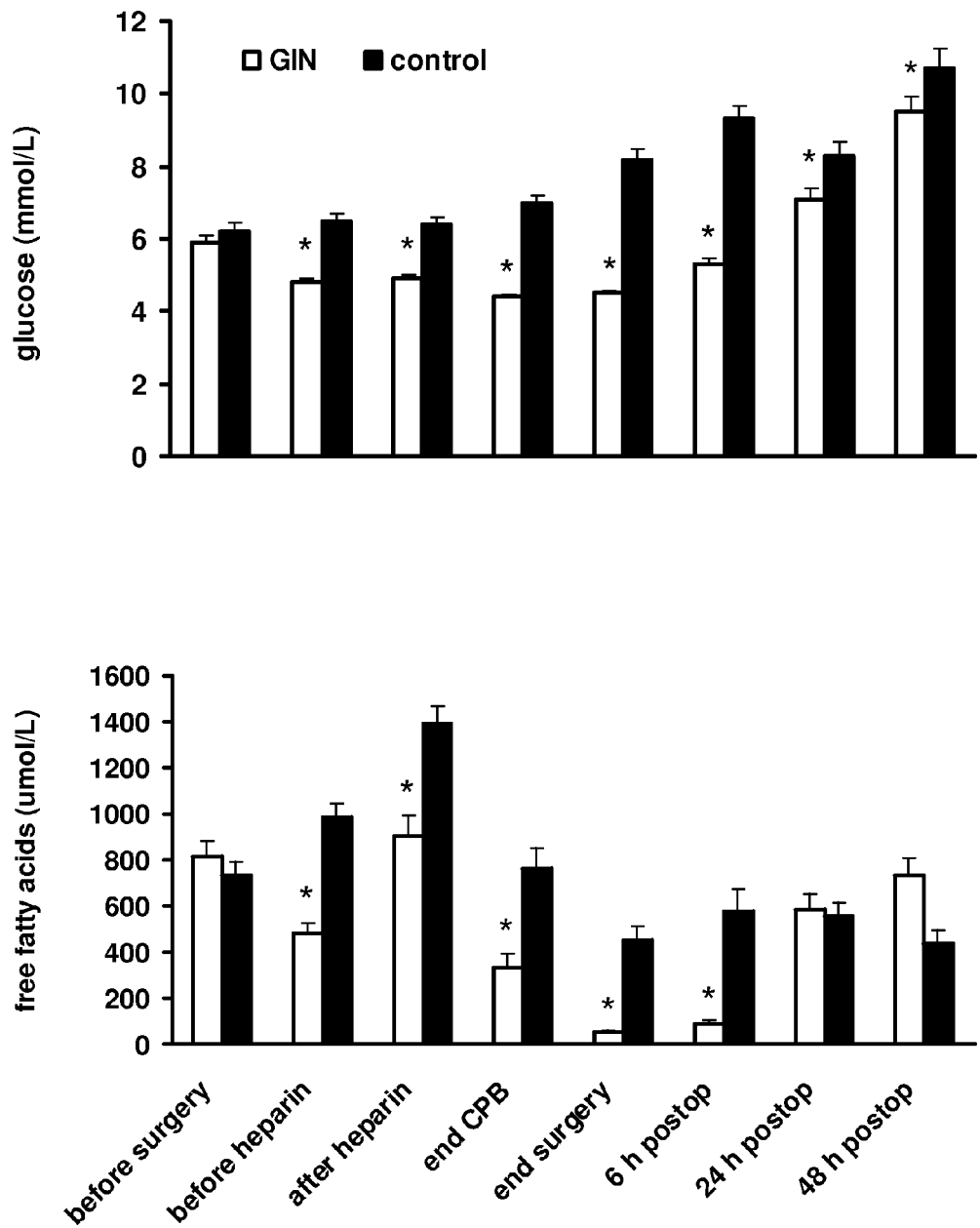
FIG. 1 illustrates plasma glucose (above) and free fatty acid (below) concentrations in control (n=50) and GIN (n=49) groups according to an embodiment of the present invention. Values are mean±SEM. *P<0.05 vs. control.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

The present invention employs the Glucose and Insulin Normoglycemia (GIN) therapy, that is glucose and high insulin dosage administration while maintaining normoglycemia and superior glycemic control to that achieved by the conventional use of insulin for novel treatment avenues.

First, there is provided a novel pharmaceutical composition to improve organ function comprising:
  from about 2200 μg to about 22 500 μg of insulin;
  salts, excipients, preservatives, thickening agents, known in the prior art for insulin formulations);
  salts, such as 20 mmol KCl/L
  Other compounds such as other anti-inflammatory compounds, GLP-1 analogs such as exendin-4); and
  a pharmaceutically acceptable carrier.

The superior glycemic control using GIN therapy as described herein offers tight stable glucose control in critically sick patients including perioperative in addition to the anti-inflammatory effect. Its safety in different clinical scenarios is yet to be proven. GIN therapy may also be employed during and/or following surgical liver resections or organ transplantation (i.e. liver, pancreas, kidney transplantation, independent of the nature of donor organ, (e.g. obtained from either a live or cadaveric donor), from an Extended (Expanded) Criteria Donor (ECD) or Standard Criteria Donor (SCD)). Furthermore, pre-operative, peri-operative, post-operative and long-term GIN therapy is also intended to be used on patients with cancer of the liver, pancreas, and kidney, or any other organ via metastasis. In addition, pre-operative, peri-operative, post-operative and long-term intermittent GIN therapy may be used to improve liver metabolic function in patients infected with either Hepatitis B and/or Hepatitis C who may or may not fail to respond to standard antiviral therapy and who are or who are not eligible for liver transplantation, or patient with non alcoholic fatty liver disease or non alcoholic steatohepatitis. Furthermore, pre-operative, pen-operative, post-operative and long-term GIN therapy as described here may also be used to improve long-term graft survival in diabetic patients who have received β-islet cell transplantation. The β-islet transplantation would be for a diabetic patient, particularly Type I diabetic patients that may or may not require additional whole organ transplant, such as a kidney transplant.

GIN therapy may be used to help minimize or mitigate organ or graft failure and may be beneficial to patients suffering from sepsis, chronic liver disease, acute or chronic liver failure, liver cirrhosis, fatty liver, and brain function abnormalities such as Alzheimer's disease. Overall, GIN therapy as described here may be used for patients receiving palliative care. Government-operated or private clinics devoted to GIN therapy can also be envisioned to provide long-term therapy.

In embodiments there is disclosed a pharmaceutical composition to improve organ function. The composition contains a large dose of insulin (about 2200 μg to about 9000 μg of insulin, suitable for the treatment of individuals of about 50 to 200 kg for 8 hours at a rate of 2 mU/kg/min). In the case of organ donors, a higher dose of 5 mU/kg/min is employed, thus a composition contains about 5500 μg to about 22 500 μg of insulin, suitable for the treatment of individuals of about 50 to 200 kg for 8 hours at a rate of 5 mU/kg/min). Patients may be obese, such as many of those with non-alcoholic fatty liver disease (NAFLD), therefore >100 kg. The insulin may be prepared in such a way that the usual annual dose for a diabetic patient may be supplied in one single (larger) vial or bottle at a similar concentration, or more or less concentrated than the insulin used by diabetic patients. As the administration of insulin as per the present invention is weight and duration related, the range to which it may be provided for use in the present invention is almost endless. This is especially the case in brain dead organ donor where use 5 mU/kg/min may be administered. The pharmaceutical compositions may comprise any suitable pharmaceutically acceptable carrier, as well as additional ingredients such as those found insulin formulations as described in the prior art and which include for example, preservatives such as phenols, cresols (e.g. metacresol), methyl, propyl or butyl parahydroxybenzoate and mixtures thereof, excipients, thickening agents such as hydrophilic polymers and any other additional compounds such as other anti-inflammatory compounds, GLP-1 analogs such as exendin-4 (which may be of use for β-islet cell transplants).

The pharmaceutical composition is used in conjunction with glucose in 'priming' the organ, tissues or cells of interest by reducing inflammation and/or reducing apoptosis to ultimately lead to fewer complications and improved patient survival.

The insulin used in the present invention may be of any origin, and preferably it may be one of human insulin, bovine insulin, or porcine insulin. It may be short-acting insulin or long acting insulin, and it may or may not comprise zinc (Zn). The insulin may be of recombinant origin. And it may comprise amino-acid modifications such as additions or deletions, as long as it remains fully functional as an insulin hormone. It may be conjugated to a carrier protein, such as a serum albumin. It may be research grade, pharmaceutical grade, or generic.

In embodiments, there are also disclosed methods of improving organ function by administering to a subject in need thereof a high dose of an insulin and a dose of dextrose (or any other suitable source of glucose) for a time sufficient for improving organ function. The administration of insulin (normally through infusion) is made in conjunction with glucose, in the form of a dextrose solution (or any other solution capable of providing glucose to the patient), to maintain a normoglycemic condition in the patient to prevent any of the potentially life threatening effects of the administration of a large dose of insulin.

In some embodiments, a group of patients may not be subjected to high insulin and glucose administration so that the effect of the high insulin and glucose treatment may be measure. Such a group may be treated according to the following approach:

Intraop

The blood glucose is measure prior to the induction of anesthesia using Accu-chek®.

The arterial blood glucose is measured at q 30-60 minutes. If blood glucose is 8-10.0 mmol/L, an insulin bolus of 2 U is given, followed by an infusion of 2 U/h. Adjust insulin infusion according to the following sliding scale to a maximum of 20 U/h.

| If blood glucose | action |
| --- | --- |
| >10.0 mmol/L | increase infusion by 2 U/h |
| >6.0 and <10.0 mmol/L | maintain current infusion rate |
| ≤6.0 mmol/L | stop insulin infusion |
| ≤4.0 mmol/L | stop insulin infusion and administer 25 mL D50% |

Postop

The blood glucose is measure every 1 to 2 h, and a blood glucose of between 6.0 and 10.0 mmol/L is targeted.

In patients that are treated with the high insulin and glucose therapy, the administration of insulin and dextrose is started when the blood glucose level of the treated subject is from about 4 mmol/L to about 6 mmol/L, or in embodiments from about 3.5 mmol/L to less than about 8.5 mmol/L. During the course of treatment, a target blood glucose level of about 4 mmol/L and about 6 mmol/L or from about 3.5 mmol/L to less than about 8.5 mmol/L is maintained through regular monitoring of the glycemia. In some embodiments, the glycemia is preferably from about 4.6 mmol/L to about 5.5 mmol/L.

A treatment according to the present invention may follow the following approach:

GIN Group

Blood glucose is checked prior to the induction of anesthesia. A bolus of insulin may be administered according to the measured blood glucose as per the following scale:

| | |
| --- | --- |
| BG 4.1-6 mmol/l | No insulin bolus |
| BG 6.1-8 mmol/l | 2U IV insulin |
| BG 8.1-12 mmol/l | 3U IV insulin |
| BG 12.1-16 mmol/l | 4U IV insulin |
| BG 16.1-20 mmol/l | 5U IV insulin |
| Above 20 mmol/l | 6U IV insulin |

BG = blood glucose

The insulin may be prepared, for example, by mixing 250 U of insulin in a total of 250 ml of Normal saline. The rate of administration of the insulin is from about 2 mU/kg/min to about 5 mU/kg/min, and the concomitant dextrose administration is provided from a 20% w/v dextrose solution at rate adjusted to maintain normoglycemia which is dependent on the status of the patient and degree of insulin resistance, normally of 40 ml/hour. Blood glucose may be checked 5 to 10 minutes after starting insulin infusion. Blood glucose may be checked every 5 to 10 minutes after starting insulin infusion.

However, at the onset of the treatment period, the glycemia of the patient may not be optimal. Should the starting blood glucose level range from about 6 mmol/L to about 12 mmol/L, the administration of insulin and dextrose is sustained until the target blood glucose level is from about 4 mmol/L and 6 mmol/L, and the rate of administration of said dose of dextrose is 20 ml/hour.

When the blood glucose reaches <6.0 mmol/L, the glucose infusion is started (dextrose 20% infusion). The dextrose 20% infusion may be supplemented with phosphate, for example phosphate at 30 mmol/L.

When the starting blood glucose level is from about 12 mmol/L or more, administration of insulin is started prior to administration of the dose of dextrose. The administration of insulin is sustained until said target blood glucose level is from about 4 mmol/L and 6 mmol/L.

Blood glucose is checked every 5 to 30 minutes, and the dextrose infusion rate is adjusted to to normoglycemia (BG 4.0 to 6.0 mmol/L). The following scale may be helpful to select the rate of infusion, but as well known in the art, they have to be adapted to the individual patient.

| | |
| --- | --- |
| If BG ≥6.5 mmol/l | ↓D20W by 40 ml/h |
| If BG 6-6.4 | ↓D20W by 30 ml/h |
| If BG 5.5-5.9 | ↓D20W by 15 ml/h |
| If BG 4.8-5.4 | maintain infusion rate |
| If BG 4.4-4.7 | ↑D20W by 10 ml/h |
| If BG 4-4.3 | ↑D20W by 20 ml/h |
| If BG 3.5-3.9 | ↑D20W by 20 ml/h + bolus 10 ml |
| If BG ≤3.4 mml/l | ↑D20W by 30 ml/h + bolus 20 ml |

According to an embodiment of the present invention, sources of exogenous glucose must be avoided (e.g. antibiotic solutions or magnesium solutions employed during the course of therapy). Moreover, the level of potassium should be closely monitored to avoid the risk of rebound hyperkalemia after the GIN treatment.

Similarly when the starting blood glucose level is from about 3 mmol/L or less, administration of dextrose is started prior to administration of the insulin, and a bolus of dextrose is administered to said subject. Furthermore, the administration of the dextrose is sustained until the target blood glucose level is from about 4 mmol/L to about 6 mmol/L.

Similarly, when the starting blood glucose level is from about 3.1 mmol/L to about 4.5 mmol/L, administration of dextrose is started prior to administration of insulin. The administration of dextrose is sustained until the target blood glucose level is from about 4 mmol/L to about 6 mmol/L.

When the target blood glucose level is from about 3 mmol/L or less, the rate of administration of the dextrose is increased, preferably by about 20 ml/hour, and a bolus of dextrose is administered to the subject (preferably 20 ml of a 20% w/v dextrose solution). The administration of the dextrose is sustained until said target blood glucose level is from about 4 mmol/L to about 6 mmol/L.

Also, when the target blood glucose level is from about 4.6 mmol/L to about 5.5 mmol/L, the rate of administration of insulin and dextrose is sustained at the pre-established rates.

When the target blood glucose level is from about 3.1 mmol/L to about 4.5 mmol/L, the rate of administration of dextrose is increased, preferably by 20 ml/hour, and the administration of said dextrose is sustained until the target blood glucose level is from about 4 mmol/L and 6 mmol/L.

When the target blood glucose level is from about 5.6 mmol/L to about 6.4 mmol/L, the rate of administration of dextrose is decreased, preferably by 20 ml/hour. Similarly, when the target blood glucose level is from about 6.5 mmol/L or more, the rate of administration of dextrose is decreased, preferably by 40 ml/hour.

The high insulin and glucose treatment may be monitored after end of the procedure or treatment Postop Before transferring the patient, reduce insulin infusion to 1 mU Kg$^{-1}$ min$^{-1}$, and check blood glucose level every 30 min for 4 hours, and then every 60 min for total of 72 hours. The dextrose infusion rate to normoglycemia (BG 4.0 to 6.0 mmol/L). The following numbers should help with the adjustment. However, they have to be adapted to the individual patient.

| | |
|---|---|
| If BG ≥6.5 mmol/l | ↓D20W by 40 ml/h |
| If BG between 6-6.4 | ↓D20W by 30 ml/h |
| If BG BTW 5.5-5.9 | ↓D20W by 15 ml/h |
| If BG BTW 4.8-5.4 | maintain infusion rate |
| If BG BTW 4.4-4.7 | ↑D20W by 10 ml/h |
| If BG BTW 4-4.3 | ↑D20W by 20 ml/h |
| If BG BTW 3.5-3.9 | ↑D20W by 20 ml/h + bolus 10 ml |
| If BG ≤3.4 mml/l | ↑D20W by 30 ml/h + bolus 20 ml |

The blood glucose level is verified more often if patient is receiving blood transfusion, receiving other intravenous dextrose solutions or eating and drinking.

The time sufficient for performing a single treatment is about 8 hours, but it may be longer or shorter, as may be required for the specific treatment protocol of the condition being treated. The treatment may be performed several times a week, preferably twice a week. Long term treatments may be performed, for example, for 24 weeks, or for the duration of the patient's life.

During treatment, the glycemia of the subject being treated is measured at numerous occasions. First, the target blood glucose level is measured 10 minutes after starting of said administering, and will be further monitored every 60 minutes until the end of the treatment. Blood glucose measurements are performed using Accu-Check™ (Roche). When the starting blood glucose level is from about 12 mmol/L or more, the target blood glucose level is measured every 10 minutes after starting of the treatment.

The method described herein may be used for the treatment of a condition which may be sepsis, a resected liver, an organ transplant, an organ donor, a deceased organ donor, a brain-dead organ donor, an organ recipient, organs for a patient in coma, a liver condition, pancreas condition, a kidney condition, insulin-resistance syndrome, metabolic syndrome (syndrome X), a metabolic syndrome caused by insulin-resistance, a cancer, a brain function abnormality, or a combination thereof.

Sepsis

Sepsis is a major problem affecting millions around the world each year. In the United States, it has a reported mortality rate between 20 and 40%. The introduction of the "Early Goal Directed Therapy" by Dr. Rivers resulted in a reduction in the relative risk of death between 50-60%. Active areas of research looking at further reducing this rate involve the role of steroids, activated protein C and glucose control. Elevated blood sugar in critically ill patients has been associated with worse outcomes. It has been shown that intensive insulin therapy to achieve tight glucose control (4.4 to 6.1 mmol/L) in critically ill patients reduced morbidity and mortality. Attempts at reproducing these results in different patient populations, however, did not show the same mortality benefits. The intensive insulin therapy RTC in patients with severe sepsis (VISEP trial) was stopped early due to an increased incidence of hypoglycaemia in the treatment group. The beneficial effects of tight glucose control were offset by the increased incidence of significant hypoglycaemia among the intensive insulin therapy group. Hence, initiating a "Normoglycemic, hyperinsulinemic clamp" as part of the early goal directed therapy in patients with severe sepsis and septic shock may decrease insulin resistance, decrease the inflammatory response, and ultimately reduce mortality.

Liver Resection

Liver resection (LR) is the treatment of choice for many primary and secondary liver malignancies. Major liver resection (MLR) (>3 segments) is associated with significant risk of liver dysfunction, morbidity and mortality even when adequate liver mass is left behind. Balanced inflammatory response is required for liver regeneration and prevention of hepatocyte apoptosis. Liver resection is the only treatment of colorectal cancer liver metastasis (CRCLM) and other hepatic malignancies that can provide long-term survival and cure in selected patients. As a result of improved imaging, better perioperative care and more effective chemotherapy there is an increase in liver resections. If the future liver remnant (FLR) left behind after a complete oncologic LR is judged adequate to sustain life then patients are considered resectable. The indications for liver surgery have expanded over the years due to advances in perioperative care and availability of detailed imaging methods for accurately assessing tumour load. Mortality from hepatic surgery has declined remarkably over the past 15 years to less than 2% for the routine resection, but postoperative morbidity rates remain high at 20%-50%.

The liver's capacity to regenerate following major hepatic surgery depends on the magnitude of the resection, the severity of the surgical stress response and the levels of glycogen stored in the hepatocytes. Tissue trauma from surgery triggers an inflammatory response that causes endothelial and epithelial cells as well as neutrophils, macrophages and lymphocytes to stimulate the secretion of proinflammatory mediators TNF-α, IL-1β and IL-6. Severe trauma can lead to persistent upregulation of cytokines and failure of the host defence system marked by increased levels of C-reactive protein (C-RP), IL-6 and acute phase protein in the patient (13, 19-21). Suppressed immune function and liver dysfunction brought about by continued upregulation of cytokines, particularly TNF-α and IL-6, renders patients more susceptible to postoperative infection, morbidity and mortality. The complement system also contributes to the stress response and has been shown to play an important role in the initiation of hepatocyte regeneration in animal models. For example, He at al. proposed existence of a complement activation threshold in deciding regenerative capacity of the liver. According to their results inhibition of C3a activation reduced hepatocyte regeneration whereas increasing C3a/ASP production enhanced the hepatic proliferative response in mice.

Hepatic surgeons want to see initiation of a proliferative response after partial hepatectomy rather than necrosis and apoptosis, which originate from hepatic dysfunction related complications. Adequate nutrition coupled with proper orchestrated interplay between pro- and anti-inflammatory mediators maintains cellular integrity by ensuring a continued energy supply for hepatocyte regeneration. An exaggerated proinflammatory response compounded by preoperative fasting diminishes the livers energy stores and culminates in an insulin resistant state in the patient. This puts the patient at higher risk for developing hyperglycaemia and leads to postoperative liver dysfunction, increased morbidity and complications, especially infections.

According to one embodiment of the present invention, insulin therapy may reduce trauma related insulin resistance, increase glycogen stores, provide an anti-inflammatory effect and improve the immune systems defence against infection.

High-insulin therapy may have an effect on markers of inflammation and hepatocyte regeneration and apoptosis, decreasing the inflammatory response, and ultimately reduce mortality. According to an embodiment of the present invention, GIN therapy may augment liver glycogen content and decrease postoperative liver dysfunction. According to another embodiment of the present invention, GIN therapy during MLR may improve metabolic support and decrease postoperative complications.

Organ Transplant

The organ transplant can be any one of a heart transplant, liver transplant, kidney transplant, pancreas transplant, a β-islet cell transplant or combinations thereof.

In the context of organ transplant, the effect of insulin therapy in addition to the maintenance of normoglycaemia during organ retrieval surgery is to prevent the inflammatory response. There are also other potential benefits from the direct effect of insulin on target organs prior to organ procurement.

A number of physiological changes also occur after brain death. The most prevalent one occurs at the endocrine level resulting in hyperglycaemia. Brain death leads to rapid disturbances that affect the hypothalamus-pituitary-thyroid axis. The hypothalamus stimulates the pituitary gland to secrete the thyroid stimulating hormone (TSH), which prompts the thyroid to release T3 and T4. After brain death, TSH and the peripheral conversion of T4 drops, which results in a rapid decline of T3 levels. This can lead to a progressive loss of cardiac contractility, increased anaerobic metabolism and accumulation of lactic acid. Pancreas production of insulin also drops after brain death leading to a decreased level of intracellular glucose, which will eventually lead to an energy deficit and the body will shift to an anaerobic state leading to acidosis and systemic hyperglycaemia. Therefore, a high dose of insulin infusion is often required to prevent the development of severe osmotic diuresis and profound hypovolemia and maintain plasma glucose within 120-180 mg/dL range. In addition, there has been a correlation between hyperglycaemia and the inflammatory response Furthermore, a high dose of insulin according to the present invention may be helpful as an organ preservation in the case of patient in coma for short or extended periods of time.

In an animal trial (Barklin A et al.), insulin therapy when given to pigs with brain death resulted in an anti-inflammatory effect with a significant reduction of cytokine concentration in donated organs (heart and kidney). In this trial, eight female landrace brain dead pigs (brain death induced by inflation of a balloon in the epidural space) were placed on insulin and eight others were not. The main finding was that insulin suppressed the IL-6 protein response which is associated with inflammation. Prevention of hyperglycemia using insulin therapy have also proved to suppress the inflammatory response in human trials (Schwarc C. et al.).

Brain death induces a massive inflammatory response such as an increased plasma levels of pro-inflammatory cytokines of interleukins (IL-6), tumour necrosis factor (TNF) and an up-regulation of their receptors in the organ. Therefore, this heightened inflammatory response seen in the donor is reflected on the transplanted grafts. A recent study has established that an increased inflammatory response is associated with a decreased recipient survival (Murugan R. et al). Another major study done in the intensive care units of a tertiary care university hospitals in the United-States showed that increased donor interleukin-6 levels before organ procurement is associated with lower recipient six-month hospital-free survival (Murugan R. et al).

Cytokines are the major inflammatory proteins implicated in the inflammatory response related to brain death. Important pro-inflammatory cytokines include tumour necrosis factor (TNF-$\alpha$) and interleukin (IL-1$\beta$) and (IL-$\alpha$). Other adhesion molecules are also implicated in this inflammatory response like ICAM-1 and VCAM-1 and E-selectins. Clinical studies on the inflammatory effect of brain death have been done on organs. An increased level of E-selectin, IL-10, interferron-$\gamma$ and TNF-$\alpha$ were found in kidneys from brain dead donors compared to kidneys from live donors. Furthermore, livers from brain dead donors had a significant increased transcription rate of IL-6, IL-10, TNF-$\alpha$, TGF-$\beta$ and MIP-1a (Kim Y. et al., Koo D. et al., Schwarc C. et al.). Overall, inflammatory markers are more highly expressed in organs from cadaveric donors than in living controls.

Organ of interest which may treated using the present invention include but are not limited to the following:

Heart

Elevated concentrations of inflammatory cytokines, induced during transplantation, in the heart lead to impaired hemodynamics after transplantation such as reduced stroke volume, elevated mean pulmonary artery pressure, and elevated left and right ventricular filling resulting in tachycardia and a reduced left ventricular performance. Additionally, the use of high dose insulin therapy has been shown to promote early metabolic recovery of the heart, myocardial protection and early functional recovery during coronary arteries bypass surgery. Patients that received a high dose insulin therapy had no perioperative myocardial infarction.

Liver

There is a direct link of liver function during transplantation and its glycogen stores (Alibegovic A. et al., Stadler M. Et al., Nettebladt C. G. et al., Astarcioglu I. et al., Caraceni P. et al., Le Couteur D. G. et al., Selzner M. et al.). Animal trials have demonstrated a linear relationship between nutrition status, liver glycogen content, and liver function after transplantation. Portal vein infusion with dextrose during transplantation modified the enzymatic profile of the transplanted livers. High insulin therapy when given to patients undergoing major liver resection resulted in an improved liver glycogen content and postoperative liver function (Hassanain M. et al.).

Kidney

Insulin infusion has been shown to have multiple beneficial effects on kidney function. Insulin therapy can lead to vasodilatation of the renal circulation, increased plasma flow and plasma renin activity (Luksch A. et al, Perlstein et al.). Results have demonstrated the additive effect of glucose and insulin as vasodilator in renal vasculature. Another important property that is also mentioned in the literature concerning insulin infusion to the kidney is reduction of oxidative stress and ischemic-reperfusion injury in the early phase of kidney transplantation. The effects of insulin infusion were also studied in the early phase of kidney transplantation. A study group randomized 20 patients to receive a combined glucose and insulin infusion and were compared to a group using glucose only infusion. Patients in the study group received 200 mg glucose per day with intravenous short-acting insulin to maintain the blood glucose level between 7 and 10 mmol/L and anti-oxidant plasma capacity was measured. After of the first post-transplantation day, antioxidant plasma capacity was found to be stable in the study group and decreased in the control group. Therefore, insulin infusion may help maintain antioxidant defences post-transplantation and decrease ischemia-reperfusion induced injury.

Pancreas

The concept of beta-cell rest evolved in the field of islet transplantation studies and shows a benefit to cell insulin content and function following a period of feedback inhibition of insulin secretion (Iversen J. et al., Draznin B. et al.). In type 1 diabetics, β-cell rest induced by diazoxide or by intensive insulin administration appears to exert a protective effect and prolong β-cell survival. Use of intensive insulin administration appears to exert a protective effect, therefore prolonging β-cell survival and improve graft survival. Experimentally, this phenomenon appears to be related to a link between β-cell functional state, antigenecity and susceptibility to cytokine injury (Mehta V. et al.). The β-islet transplantation would be for a diabetic patient, particularly Type I diabetic patients, that may or may not require an organ transplant, such as a kidney transplant.

There is mounting evidence that metabolic demands on cells with a prominent secretory function may be responsible for imbalances in endoplasmic reticulum (ER) homeostasis and accumulation of misfolded proteins, a condition known as ER stress. Prolonged or severe ER stress may result in permanent cell loss, and in the case of a transplanted organ, may predispose to antigen presentation and risk of alloimmune response.

The method of treatment may be for transplant donor, a transplant receiver, or both a transplant donor and a transplant receiver, as the beneficial effects of insulin on the organ can be harnessed even prior to removal of the organ for transplant. Thus, the donor can be alive, deceased donor, brain dead, or in coma.

Liver Conditions and Metabolic Syndromes

Liver condition can be treated with the method of the present invention and they include alcoholic fatty liver, non-alcoholic fatty liver, alcoholic steatohepatitis, non-alcoholic steatohepatitis, steatohepatitis with fibrosis, early fibrosis, fibrosis, cirrhosis, hepatitis B-infection, hepatitis B-infection with HIV co-infection, hepatitis C-infection, hepatitis C-infection with HIV co-infection.

Fatty liver disease (FLD) is a reversible condition where large vacuoles of triglyceride fat accumulate in liver cells via the process of steatosis (i.e. abnormal retention of lipids within a cell). Despite having multiple causes, fatty liver can be considered a single disease that occurs worldwide in those with excessive alcohol intake and those who are obese (with or without effects of insulin resistance). The condition is also associated with other diseases that influence fat metabolism. Morphologically it is difficult to distinguish alcoholic FLD from non alcoholic FLD and both show micro-vesicular and macrovesicular fatty changes at different stages.

Steatohepatitis is a type of liver disease characterized by inflammation of the liver with concurrent fat accumulation in liver ("steato", meaning fat, "hepatitis", meaning inflammation of the liver). Mere deposition of fat in the liver is termed steatosis, and together these constitute fatty liver changes. Classically seen in alcoholics as part of alcoholic liver disease, steatohepatitis also is frequently found in people with diabetes and obesity. When not associated with excessive alcohol intake, it's referred to as non-alcoholic steatohepatitis, or NASH and is the progressive form of the relatively benign Non-alcoholic fatty liver disease. Steatohepatitis of either etiology may progress to cirrhosis, and NASH is now believed to be a frequent cause of unexplained cirrhosis (at least in Western societies).

Fibrosis is the formation or development of excess fibrous connective tissue in an organ or tissue as a reparative or reactive process, as opposed to a formation of fibrous tissue as a normal constituent of an organ or tissue. Scarring is confluent fibrosis that obliterates the architecture of the underlying organ or tissue.

Liver cirrhosis is an irreversible process that correlates with liver function deterioration. The degree of cirrhosis is currently measured by the Child-Pugh scoring system reflecting the severity of the patients' clinical condition. It also acts as a good prognostic tool with 70-80% accuracy in predicting patient's survival.

Chronic hepatitis C infection is the main cause of chronic liver disease leading to liver transplantation in North America. It is estimated that 123-170 million people are living with Hepatitis C virus (HCV) infection worldwide, and up to 20% of chronically infected individuals will develop liver cirrhosis over the next 20 to 25 year period. Consequently, HCV infection is emerging as the leading cause of both chronic hepatitis and cirrhosis, even in countries where alcoholic liver cirrhosis used to be the predominant cause of cirrhosis. Recent studies showed an important link between HCV and liver metabolic derangement (Balsano C. et al.). It has been shown that HCV causes insulin resistance and metabolic syndrome that will ultimately facilitate the rapid development and evolution of hepatic fibrosis. Moreover, treating insulin resistance in patients with HCV cirrhosis has been speculated not only to avoid complications of metabolic syndrome but also to prevent liver disease progression and increase response to HCV treatment.

The present invention may be useful to treat liver cirrhosis, and especially HCV induced cirrhosis, thus helping to halt or delay the progression of liver disease. An application of the present invention would be to convert non-acutely decompensated HCV induced Child (B) cirrhosis patients into a Child (A) cirrhosis, knowing that Child (A) patients have excellent survival when compared to Child (B) patients.

Multiple recent studies showed an important causal link between HCV and liver metabolic derangement. A link between infection with HCV and an increased risk of type II diabetes mellitus, insulin resistance or hepatic steatosis has been well documented even in non-cirrhotic patients (Delgado-Borrego A. et al., Mason A. et al., Rubbia-Brandt L. et al.). These effects vary in predominance in a genotype-dependent fashion. Metabolic syndrome develops due to a direct effect of the Hepatitis C virus proteins interfering with the insulin signaling cascade by multiple complex mechanisms, and resulting in inflammation, steatosis, fibrosis, cirrhosis, apoptosis, altered gene expression and eventually hepatocellular carcinoma (HCC).

The understanding of these molecular mechanisms and interactions is enhanced with ongoing studies using genomics and proteomics approaches. It is now recognized that the oxidative stress and consequent inflammatory process caused by the HCV proteins—through the mitochondria and endoplasmic reticulum—is the chief initiator of its pathogenesis (Sheikh M. et al.). Multiple cytokines are released, which inhibits the function of insulin receptor substrates and decreases the expression of the glucose transporter and lipoprotein lipase in peripheral tissues. The resulting insulin resistance prevents glucose uptake into hepatocytes and adipocytes causing a state of hyperinsulinemia and hyperglycemia. While the hyperinsulinemic state enhances hepatic steatosis, the hyperglycemia further contributes to an increase in the inflammatory process. Therefore, several pro-inflammatory cytokines such as IL-1, IL-6 and TNF-α are associated with high insulin resistance, and are significantly upregulated in patients with chronic hepatitis C leading to a vicious cycle of chronic hepatic inflammation, and escalating insulin resistance, leading ultimately to increasing fibrosis. Hence, studies have identified increased insulin resistance as an independent key predictor of the rapid progression of hepatic fibrosis (Hui J. et al.).

Insulin resistance and metabolic syndrome influence the progression chronic hepatitis C. The highly variable natural course of HCV infection depends on both viral and host factors. For example, age, male gender, obesity, alcohol consumption and also insulin resistance are defined risk factors for a progressive course of chronic hepatitis C and hepatic fibrosis. Insulin resistance is believed to represent one of the central clinical features of the metabolic syndrome associated with chronic hepatitis C (Balsano C. et al., Bernsmeier C. et al.). Multiple trials have targeted insulin resistance as an adjuvant way to manage hepatitis C liver disease. Life style modifications as well as anti-diabetic drugs such as metformin and thiazolidinediones have been used with some promising results on improving fibrosis and increasing the response to interferon-based therapy. A recent pilot study has also shown improved insulin sensitivity as defined by a significantly improved ratio of HOMA-IR (homeostasis model assessment of insulin resistance) in patients with chronic hepatitis C who were treated with angiotensin II receptor blockers. Additional studies are needed to verify the advantages of insulin sensitization in this population of patients.

Insulin resistance reduces the response to antiviral therapy. It has been proposed that a direct viral effect leads to the inhibition of interferon signaling pathway, eventually reducing the response to antiviral therapy in patients with HCV infection. Then again, another factor that has also shown to have a negative impact on patients' response to antiviral treatment is the increasing insulin resistance associated with HCV infection. Interestingly, multiple studies have demonstrated better treatment responses in HCV patients following trials of insulin-sensitization causing a decrease in insulin resistance (Douglas M. et al., Bernsmeier C. et al.).

It has been proposed that a direct viral effect leads to the inhibition of interferon signaling pathway, eventually reducing the response to antiviral therapy in patients with HCV infection. An additional factor that has also shown to have a negative impact on patients' response to antiviral treatment is the increasing insulin resistance associated with HCV infection. Multiple studies have demonstrated better treatment responses in HCV patients following trials of insulin-sensitization causing a decrease in insulin resistance.

Thus, long term high-dose insulin therapy can be used as an effective adjuvant therapy to patients with HCV chronic liver disease as it targets its pathophysiology at both the cellular and molecular levels. The implementation of drugs to improve glucose metabolism and improve upon insulin resistance is a likely useful method that aims to prevention fibrosis and other liver conditions, and even hepatocellular carcinoma. The liver is a self regenerating organ. Liver progenitor cells (LPCs) are responsible for the regeneration process following liver damage, and therefore, are viewed as a potential therapeutic alternative to organ transplantation. HCV has a significant recognizable impact on the liver histology. Despite continued viral infection, both biochemical and histological studies have demonstrated the ability of the liver to regain improved function in patients with chronic hepatitis C infection following treatments aimed at reducing inflammation.

The method of the present invention may be employed for treating a cancer, such as a cancer of the liver, a cancer of the pancreas, and a cancer of the kidney, or any metastasized cancer.

Recent data have expanded the concept that inflammation is a critical component of tumour progression. Many cancers arise from sites of infection, chronic irritation and inflammation. It is now becoming clear that the tumour microenvironment, which is largely orchestrated by inflammatory cells, is an indispensable participant in the neoplastic process, fostering proliferation, survival and migration. In addition, tumour cells have co-opted some of the signalling molecules of the innate immune system, such as selectins, chemokines and their receptors for invasion, migration and metastasis. These insights are fostering new anti-inflammatory therapeutic approaches, such as high insulin therapy according to the present invention, to cancer development.

Oxidative Stress Associated Diseases

Oxidative stress is caused by an imbalance between the production of reactive oxygen species and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA, which may cause inflammation and result in numerous conditions.

The oxidative stress associated disease can be for example Alzheimer's disease, Parkinson's disease, Parkinson's disease with dementia with Lewy body, Huntington's disease, multiple system atrophy (MSA), progressive supranuclear palsy (PSA), corticobasal degeneration (CBD), and fronto-temporal lobe degeneration. The oxidative stress associated disease may be atherosclerosis, heart failure, myocardial infarction, metabolic syndrome (syndrome X), and chronic fatigue.

The method of the present invention can be used as a pre-operative treatment, a peri-operative treatment, a post-operative treatment, a long term treatment or combinations thereof. When used as a pre-operative treatment, it may further comprise a pre-operative antibiotic treatment, with for example Ampicillin® and Cephtriaxone®.

GIN therapy as described herein can be used for patients receiving palliative care, or pre-operative care. Government-operated or private clinics devoted to GIN therapy can be envisioned to provide therapy to patients over the long-term or prior to surgery, as may be required by the surgical protocol.

In embodiments, there are disclosed a method of intensive insulin therapy which includes
a) performing a pre-insulin therapy blood test on a subject;
b) treating the subject with an intensive insulin therapy; and
c) performing a post-insulin therapy blood test on the subject.

Several blood markers can be tested to assess the health and suitability of the subject receiving the treatment. For example, the pre-insulin therapy blood test may include measurement of HbA1C level, C-peptide, albumin, a complete blood count, pre-albumin level, electrolytes level, renal function, C-reactive protein (CRP) and a free cortisol level.

When the intensive insulin therapy is for a pre-operative treatment, the pre-insulin therapy blood test may include measurements of HbA1C, C-peptide, albumin, arterial blood gas (ABG), lactic acid, insulin, glucagon, free fatty acid (FFA), TNF alpha, IL-1 beta, IL-6, IL-8, a complete blood count, pre-albumin, electrolytes level, renal function, C-reactive protein (CRP) and free cortisol.

When the intensive insulin therapy is for a pre-operative treatment, a peri-operative treatment, a post-operative treatment, or combinations thereof, the post-insulin therapy blood test can include measurement of arterial blood gas (ABG), lactic acid, insulin, glucagon, free fatty acid (FFA), TNF alpha, IL-1 beta, IL-6, and IL-8. The post-insulin therapy blood test can be performed at the arrival of said subject in a post anesthesia care unit, at 4 hours after surgery, or both.

When the intensive insulin therapy is for a pre-operative treatment, a peri-operative treatment, a post-operative treatment, or combinations thereof, the post-insulin therapy blood test can include measurement of a complete blood count, pre-albumin, electrolytes, renal function, C-reactive protein (CRP) and free cortisol. The post-insulin therapy blood test can be performed at 24 hours after surgery, at 48 hours after surgery, 7 days after surgery, or combinations thereof.

When the intensive insulin therapy is for a pre-operative treatment, a peri-operative treatment, a post-operative treatment, or combinations thereof, the post-insulin therapy blood test can include measurement of arterial blood gas (ABG), lactic acid, insulin, glucagon, free fatty acid (FFA), TNF alpha, IL-1 beta, IL-6, IL-8, a complete blood count, pre-albumin, electrolytes, renal function, C-reactive protein (CRP) and free cortisol. The post-insulin therapy blood test can be performed at 72 hours after surgery.

When the intensive insulin therapy is for a pre-operative treatment, a peri-operative treatment, a post-operative treatment, or combinations thereof, the post-insulin therapy blood test can include measurement of HbA1C, C-peptide, insulin, and albumin.

Also, the post-insulin therapy blood test can include comprises measurement of the level of IL-2, IL-4, IL-6, IL-10, IL-1b, IL-1, TNF-$\alpha$, TNF-$\beta$, MCP-1, CCL2/MCP-1, CCL3/MIP-1a, CCL4/MIP-1$\beta$, TGF-$\beta$1, MIP-1a, ICAM-1, CXCL3/KC, CXCL1/GRO-$\alpha$, CXCL2/GRO-$\beta$, CXCL10/IP-10, and INF-$\gamma$.

The post-insulin therapy blood test is can be performed at 6 hours, 12 hours, 24 hours, 48 hours, and 7 days post treatment.

In embodiments, there is disclosed a use of a method for improving organ function as described herein for the treatment of an intensive care cardiac patient. The cardiac patient may be suffering from a condition chosen from Coronary heart disease, a cardiomyopathy, a cardiovascular disease, ischaemic heart disease, heart failure, hypertensive heart disease, inflammatory heart disease, and a valvular heart disease. The cardiac patient may have received or will be receiving a heart transplant. Therefore, the method of improving of organ function is used prior to, during, and/or after organ transplant, as required by the treatment protocol.

In embodiments, there is disclosed a use of a method for improving organ function as described herein for the treatment of a patient for cardioprotection during coronary artery bypass grafting (CABG) surgery. CABG is defined as the prevention or attenuation of myocardial cell death and contractile dysfunction after myocardial ischemia and reperfusion. With cardiac arrest and the institution of cardiopulmonary bypass (CPB) ischemia is induced and concentrations of high-energy phosphates in cardiomyocytes fall, resulting in intracellular acidosis, loss of membrane integrity and ultimately cell death. Restoration of coronary blood flow following CPB (reperfusion) further aggravates myocyte necrosis. Elective CABG can, thus, be viewed as an iatrogenic myocardial infarction (MI) that may be measured by the large elevation in cardiac biomarkers. Despite advances in cardioprotection strategies, myocardial dysfunction following open heart surgery remains an ongoing problem in an increasingly vulnerable patient population.

According to an embodiment of the present invention, the glucose and insulin administration while maintaining normoglycemia (GIN) therapy during CABG using a hyperinsulinemic-normoglycemic clamp technique may be cardioprotective and improves myocardial function.

The present invention will be more readily understood by referring to the following examples which are given to illustrate the invention rather than to limit its scope.

Example 1

Pharmaceutical Composition for Major Liver Surgery

One such composition includes
insulin at 250 U in 250 ml of Normal Saline (1 U/ml);
20 mmol/L KCl (if normal renal function)
The entire composition comprising a total volume of 250 mL (250 U insulin total) is administered at 2 ml/kg/min.

Example 2

Pharmaceutical Composition for Cardiac Patients

One such composition includes
insulin at 500 U in 500 ml of Normal Saline (1 U/ml);
20 mmol/L KCl (if normal renal function)
The entire composition comprising a total volume of 500 mL (500 U insulin total) is administered at 5 ml/kg/min.

Example 3

Treatment of Patients to Improve Organ Function in an HCV Infected Patient

A patient suffering from a hepatitis C virus infection is subjected to a normoglycemic hyperinsulinimic clamp with administered dextrose (from a 20% dextrose solution in water) and insulin (2 mU/kg/min). The duration of the treatment is 8 hours. The blood sugar goal range: 4-5.5 mmol/l, and the blood glucose level measurement are performed using (Accu-Check™) and following the following protocol. The patient will not be allowed to eat during the period of the insulin infusion.

Protocol:
 If blood glucose is within targeted range (4-5.5 mmol/l)
  Start Insulin infusion with Dextrose infusion (20% Dextrose) at 40 ml/hr
  Check blood glucose after 10 min and adjust according to protocol
  Check blood glucose every 60 min till the end of the session
 If blood glucose is above target (5.5-12 mmol/l)
  Start Insulin infusion with Dextrose infusion (20% Dextrose) at 20 ml/hr
  Check blood glucose after 10 min and adjust according to protocol
  Check blood glucose every 60 min till the end of the session
 If blood glucose is high (above 12 mmol/l)
  Start Insulin infusion alone
  Check blood glucose every 10 minutes until blood sugar is below 12 mmol/l and start Dextrose infusion (20% Dextrose) according to protocol Check blood glucose every 60 minutes till the end of the session.

TABLE 1

| Blood glucose level | Dextrose infusion rate |
|---|---|
| Below 3.1 mmol/l | ✓ Increase rate of D20W by 20 ml/hr<br>✓ Give 20 ml bolus of D20W<br>✓ Inform research MD on-call |
| 3.1-4 mmol/l | ✓ Increase rate of D20W by 20 ml/hr |
| 4.1-5.5 mmol/l | ✓ Maintain same infusion rate |
| 5.6-6.4 mmol/l | ✓ Decrease rate of D20W by 20 ml/hr |
| More than 6.4 mmol/l | ✓ Decrease rate of D20W by 40 ml/hr<br>✓ Inform research MD on-call |

Example 4

Intensive Insulin Therapy of Patients with HCV Infection

The patient is subjected to GIN treatment as described in Example 3. The treatment is repeated twice a week, for 24 weeks.

Detailed analysis of liver function status is targeted. Multidisciplinary assessment tools will be used; elements of interviews, clinical examination, blood samples and radiological investigations will be utilized for that purpose. Follow-up blood investigations will be scheduled every 2 months to identify changes in liver function along with the routine blood investigations required for this population of patients.

Liver Function Assessment:

Multiple scoring systems and parameters are used to get a better global view of the liver function related improvements.

TABLE 2

Child-Pugh scoring system

| Measure | 1 point | 2 points | 3 points |
|---|---|---|---|
| Bilirubin (total) μmol/l (mg/dl) | <34 (<2) | 34-50 (2-3) | >50 (>3) |
| Serum albumin g/l | >35 | 28-35 | <28 |
| INR | <1.7 | 1.71-2.20 | >2.20 |
| Ascites | None | Mild | Severe |
| Hepatic encephalopathy | None | Grade I-II (or suppressed with medication) | Grade III-IV (or refractory) |

MELD (Model for End-Stage Liver Disease) Score:—
As Per UNOS (United Network for Organ Sharing)

Liver Function Blood Tests:

Multiple parameters are recorded, including the peaks and trends of ALT, AST, GGT, ALK, Prothrombin time, INR and total and direcet bilirubin.

Dynamic Liver Function Tests:

Generally, dynamic liver function tests are considered distinctive because they are, to a lesser extent, determined by extrahepatic factors. They are used to assess hepatic synthetic capacity and clearance. Stable isotope tracers for albumin, glucose and leucine are used. In addition to non invasive tests: the aminopyrine breath test and the indocyanine plasma clearance using finger tip light sensor.

Hepatitis Related—Quality of Life

Questionnaires (SF-36 and EQ-D5) will be used to assess the quality of life. Both have been extensively used and proven reliable.

Optional biopsies of the liver, muscle, subcutaneous and visceral abdominal fat will be taken. Histological grading of liver cirrhosis, steatosis and fibrosis will be assessed. RT-PCR measures of mRNA activity in liver, fat and muscle examining elements of glucose, fat and protein metabolism, cells energy, apoptosis, and replicative activity.

Insulin resistance, lipid profile and inflammatory and hormonal changes:

HOMA-IR (homeostasis model assessment of insulin resistance):

$$\text{fasting glucose (mmol/L)} \times \text{fasting insulin (mIU/L)} / 22.5 \quad \text{Formula}$$

Lipid profile (LDL, HDL, cholesterol, triglycrides)

Hormonal changes (insulin, C-peptide, glucagon, cortisol, ASP, Free fatty acids, Adiponectin, leptin)

TABLE 3

| Inflammatory cytokines and growth factors: | |
|---|---|
| Interleukins | IL-1, IL-4, IL-6,, IL-8, IL-10, IL-12, IL-15, IL-17, IL-18 |
| Tumour Necrosis Factors | TNF-α, TNF-β |
| Macrophage Chemoattractant Proteins | MCP-1, CCL2/MCP-1, CCL3/MIP-1a, CCL4/MIP-1β |
| Growth Factors | HGF (Hepatocyte growth factor), GF (Growth factor), EGF (epidermal growth factor), VEGF (vascular endothelial growth factor), TGF-β1 (transforming growth factor) |
| Macrophage Inflammatory Protein | MIP-1a |
| Intercellular Adhesion Molecules | ICAM-1 |
| T-cells and Natural Killer cells | CXCL3/KC, CXCL1/GRO-α, CXCL2/GRO-β, CXCL10/IP-10 |
| Suppressor Of Cytokine Signaling Proteins | SOCS-1, SOCS-3, SOCS-7 |
| Interferon | |
| Complement system | |

TABLE 4

Time schedule summarizing the needed investigations at different stages of the study:

| Start of the study | 12th month (half-way) | End of the study | Regular follow ups (every 2 months) |
|---|---|---|---|
| Brief physical exam<br>Basic Labs (CBC, fasting blood sugar and insulin, coagulation profile, LFT's, Renal profile)<br>Cytokines, growth factors and hormones<br>Lipid profile<br>Dynamic liver function test | In addition to regular follow up requirements:<br>Lipid profile<br>Dynamic liver function test<br>Quality of life questionnaires | Brief physical exam<br>Basic Labs (CBC, fasting blood sugar and insulin, coagulation profile, LFT's, Renal profile)<br>Cytokines, growth factors and hormones<br>Lipid profile<br>Dynamic liver function test | Brief physical exam<br>Basic Labs (CBC, fasting blood sugar and insulin, coagulation profile, LFT's, Renal profile)<br>Cytokines, growth factors and hormones |

TABLE 4-continued

Time schedule summarizing the needed investigations at different stages of the study:

| Start of the study | 12$^{th}$ month (half-way) | End of the study | Regular follow ups (every 2 months) |
|---|---|---|---|
| Quality of life questionnaires<br>Abdominal MRI and<br>Fibroscan<br>Portal pressures<br>measurement<br>optional: Biopsies (liver, muscle, fat) | | HCV viral load<br>Quality of life questionnaires<br>Fibroscan<br>Portal pressures measurement<br>optional: Biopsies (liver, muscle, fat) | |

Example 5

GIN Therapy on Intensive Care Cardiac Patients

A patient suffering from a cardiac problems was subjected to a cardiac surgery involving a coronary artery bypass. The patient is subjected to a normoglycemic hyperinsulinimic clamp with administered dextrose (from a 20% dextrose solution in water) and insulin (5 mU/kg/min). The duration of the treatment is 8 hours. The blood sugar goal range: 4-6 mmol/l, and the blood glucose level measurement are performed using (Accu-Check™) and following the following protocol. The patient will not be allowed to eat during the period of the insulin infusion.

The GIN treatment was performed as described in Example 3. The treatment is repeated twice a week, for 24 weeks. During the course of the treatment, the following were measured.

Insulin Resistance, Lipid Profile and Inflammatory and Hormonal Changes:

HOMA-IR (Homeostasis Model Assessment of Insulin Resistance):

$$\text{fasting glucose (mmol/L)} \times \text{fasting insulin (mIU/L)} / 22.5. \quad \text{Formula}$$

Lipid profile (LDL, HDL, cholesterol, triglycrides)

Hormonal changes (insulin, C-peptide, glucagon, cortisol, ASP, Free fatty acids, Adiponectin, leptin)

TABLE 5

Inflammatory cytokines and other factors:

| Interleukins | IL-6,, IL-8 |
|---|---|
| Tumour Necrosis Factors | TNF-α, TNF-β |
| Complement system | C3 and C4 |

TABLE 6

Time schedule summarizing the needed investigations at different stages of the study:

| Start of the study | 12$^{th}$ month (half-way) | End of the study | Regular follow ups (every 2 months) |
|---|---|---|---|
| Brief physical exam<br>Basic Labs (CBC, fasting blood sugar and insulin, coagulation profile, LFT's, Renal profile)<br>Cytokines, growth factors and hormones<br>Low Systemic Vascular Resistance (SVR)<br>Troponin levels<br>Lipid profile<br>Portal pressures measurement<br>Quality of life questionnaires | In addition to regular follow up requirements:<br>Lipid profile<br>Low Systemic Vascular Resistance (SVR)<br>Troponin levels<br>Quality of life questionnaires | Brief physical exam<br>Basic Labs (CBC, fasting blood sugar and insulin, coagulation profile, LFT's, Renal profile)<br>Cytokines, growth factors and hormones<br>Lipid profile<br>Low Systemic Vascular Resistance (SVR)<br>Quality of life questionnaires<br>Portal pressures measurement | Brief physical exam<br>Basic Labs (CBC, fasting blood sugar and insulin, coagulation profile, LFT's, Renal profile)<br>Cytokines, growth factors and hormones<br>Low Systemic Vascular Resistance (SVR) |

Example 6

GIN Therapy on Cardiac Patients Undergoing Coronary Artery Bypass Grafting (CABG)

One hundred patients are enrolled in the study. The patients are scheduled for elective CABG surgery. Patients with elevated baseline cardiac troponin I (cTnI) levels and combined CABG valve procedures are not eligible. Consenting patients are allocated according to a computer-generated randomization schedule to GIN or standard metabolic care (Plan procedure, SAS software).

Surgical and Anesthetic Care

Anesthetic and surgical, treatment is performed following the standards established in the Royal Victoria hospital, Montreal, Canada. Patients receive standardized total intravenous anesthesia using sufentanil, midazolam and pancuronium administered by the same anesthesiologist. After induction of anesthesia a transesophageal echocardiogram (TEE) probe is inserted. Patients are operated by the same surgeon. The CPB is conducted with a roller pump and a membrane oxygenator primed with a solution consisting of 1 L Ringer's lactate, 5000 IU heparin, 750 ml Pentaspan® (Bristol-Myers Squibb Canada Co., St Laurent, PQ, Canada), and 44 mEq bicarbonate. Immediately prior to CPB, heparin 400 IU/Kg is administered intravenously followed by additional doses, if necessary, to maintain an activating clotting time >500 s. During CPB, pump flow is set at 2.4 times the body surface area and mean arterial pressure (MAP) maintained between 50 and 60 mmHg. Temperature is allowed to drift with active rewarming at the end of CPB. Cardioplegia solution is free of glucose and consists of high dose (100 mEq/L) and low dose (40 mEq/L) potassium used at the discretion of the cardiac surgeon. Protamine is administered as 1 mg/100 IU of the heparin dose after separation from CPB. During the pre-CPB period, at separation from CPB and post-CPB, hemodynamic targets are a heart rate (HR) between 50 to 90 bpm with a MAP>60 mmHg and <100 mmHg. Filling pressures are maintained at 10 to 15 mmHg for pulmonary capillary wedge pressure (PCWP) and 5 to 12 mmHg for central venous pressure (CVP). The cardiac index (CI) is maintained >2.0 L min-1 m-2 124 and the mixed venous saturation >55%. Action was undertaken if any of these goals are not met, however, separation from CPB is attempted without use of inotropic support. Heart rate, MAP, CVP, PCWP and CI are measured pre-CPB and post-CPB, after sternal closure. Hematocrit is maintained at a level>30% pre-CPB, >21% during and after CPB.

Experimental Protocol

Control group: prior to the induction of anesthesia, a blood glucose value is determined. Arterial blood glucose measurements are performed every 30 minutes while in the operating room. At any of these measurements if the blood glucose is ≥10.0 mmol/L an insulin (Humulin® 132 R regular insulin, Eli Lilly and Company, Indianapolis, Ind.) bolus of 2 U followed by an infusion of 2 U/h is started. The insulin infusion is then adjusted according to the following sliding scale to a maximum of 20 U/h.

| If blood glucose | action |
| --- | --- |
| >10.0 mmol/L | increase infusion by 2 U/h |
| >6.0 and <10.0 mmol/L | maintain current infusion rate |
| ≤6.0 mmol/L | stop insulin infusion |
| ≤4.0 mmol/L | stop insulin infusion and administer 25 mL Dextrose 50% |

Postoperative blood glucose management is conducted aiming at a blood glucose between 4.0 and 8.0 mmol/L. Blood glucose is measured initially every 1 to 2 hours until blood glucose is within the target range.

GIN group: After obtaining a baseline blood glucose level a 2 U priming bolus of insulin is followed by insulin infusion at a rate of 5 mU $Kg^{-1}$ $min^{-1}$. Additional insulin boluses are given if the blood glucose remains >6.0 mmol/L according to the following sliding scale.

| If blood glucose | |
| --- | --- |
| 6.1-8.0 mmol/L | 2 U |
| 8.1-10.0 mmol/L | 4 U |
| 10.1-12.0 mmol/L | 6 U |
| 12.1-14.0 mmol/L | 8 U |
| >14.0 mmol/L | 10 U |

Ten minutes after commencing the insulin infusion and when the blood glucose is <6.0 mmol/L, a continuous infusion of glucose (dextrose 20%) supplemented with potassium (40 mEq/L) and phosphate (30 mmol/L) is administered at a rate adjusted to preserve normoglycemia between 4.0 and 6.0 mmol/L. The insulin infusion continues until sternal closure and then is decreased to 1 mU $Kg^{-1}$ $min^{-1}$ until discharge from the intensive care unit (ICU) or 24 hours after surgery. Arterial blood glucose is measured every 5 to 20 minutes throughout the procedure by using the Accu-chek® glucose monitor (Roche Diagnostics, Switzerland) and every hour in the ICU.

Echocardiographic Measurements

Echocardiographic data are collected after induction of anesthesia and at skin closure. Two-dimensional (2D) and Doppler echocardiography is performed on a Vivid 7 ultrasound machine (GE Healthcare, Milwaukee, Wis.) with a multiplane TEE probe. All examinations are digitally stored and interpreted by two cardiac anesthesiologists blinded to treatment and intraoperative data. Left ventricular systolic function is assessed by calculating the fractional area change (FAC). The myocardial performance index (MPI), a Doppler-derived interval index that incorporates both systolic and diastolic parameters into a single dimensionless measure, is used to assess global myocardial performance.

Analytical Methods

Blood Samples:

The cTnI was measured on the ADVIA Centaur® (Bayer Corporation, Tarrytown, N.Y.) using two monoclonal antibodies specific for independent epitopes. Plasma insulin, glucose, lactate, free fatty acids (FFA) and serum cortisol are measured using methods described previously (Schricker T., et al.). Epinephrine and norepinephrine plasma concentrations were determined by reversed-phase high performance liquid chromatography.

Muscle Biopsies:

Right atrial appendage muscle biopsies are taken before and after separation from CPB. The muscle specimens are immediately frozen in liquid nitrogen and stored at −80° C. until analysis. Tissue samples were immersed in lysis buffer (20 mM Tris 175 pH 7.5, 140 mM NaCl, 1 mM $CaCl_2$, 1 mM $MgCl_2$, 10% glycerol, 1% NP40, 10 mM NaF, 2 mM $Na_3VO_4$, 1 mM PMSF and 1% of protease inhibitor) and pulverized by glass on glass homogenization. The homogenates are incubated for 1 h (shaken every 10 min) and centrifuged at 13,000 rpm for 10 min. The supernatant is then collected. Protein concentrations are determined by BCA protein Assay (Thermo Scientific). Equal amounts of tissue protein extract (50 μg) are loaded and separated on SDS-polyacrylamide electrophoresis gels. After migration, proteins are transferred on nitrocellulose membranes and incubated at room temperature for 1 hour in 5% non-fat dry milk TBST. Primary antibodies (listed below) are incubated overnight at 4° C. and secondary antibody incubated for 1 hour at room temperature, both in 2.5% milk TBST solution. Bands are detected by chemiluminescence and quantified with Imagequant TL software. A same control sample is loaded on each gel and each band is expressed as a ratio of sample intensity over control. Results are expressed relative to alpha-tubulin band-intensity on the same sample and same gel.

Antibodies Used:

phospho-Akt (Ser 473), 60 kDa, Cell Signalling (9271), AMPK-α, 62 kDa, Cell Signaling (2532), Akt ½, 60 kDa, Santa Cruz Biotechnologies (SC-8312), phosphor AMPK ser 485/491 62 kDa Cell Signaling (4185s).

Glycogen content is measured in muscle samples following acid hydrolysis of glycogen to glucose. In brief, between 5 and 10 mg of muscle is homogenized using a hand-held tissue grinder in 100 μl of 0.5M Perchloric acid, followed by hydrolysis in 1N HCl for 2 hours at 95-100° C. Glucose released from this hydrolysis is then measured using a coupled enzyme reaction with hexokinase and glucose-6- phosphate dehydrogenase. The formation of NADPH from this reaction is followed using a Beckman DU-65 spectrophotometer at 340 nm.

Glycogen synthase activity is determined using a two-step spectrophotometric assay. In brief, 7-10 mg of frozen muscle are homogenized (1:39 w:v) in ice-cold 50 mM TRIS-HCl (pH 7.5), 5 mM EDTA, 5 mM DTT and 50 mM NaF using a hand-held glass-glass homogenizer. In the first step of the assay, uridine-5'-diphosphate glucose (UDP-glucose; 7.1 mM) is at 37° C. in the presence of 50 mM TRIS-HCl (pH 7.5), 5 mM EDTA, 11.25% glycogen (w:v), and 15 mM DTT. This reaction is performed in the presence of 0.1 or 10 mM of glucose-6-phosphate (G6P) to measure, respectively, G6P independent GS activity (I-form activity) or total GS activity (I-plus D-form). The reaction is then stopped by incubating the reaction mixture at 93° C. for 4 minutes, followed by centrifugation at 10000 g for 5 minutes. The supernatant is then used to determine the quantity of UDP produced in the first step using a coupled enzyme reaction containing 50 mM TRIS-HCl (pH 7.5), 5 mM EDTA, 10 mM $MgCl_2$, 7.5 mM DTT, 70 mM KCl, 0.1 mM phosphoenolpyruvate (PEP), 5 U/mL lactate dehydrogenase (LDH), 0.2 mM NADH, 0.0004% (w:v) BSA, and 20 U/mL pyruvate kinase. The consumption of NADH was followed over 15 minutes at 340 nm with a Beckman DU-65 spectrophotometer. The fractional velocity (FV; 100× activity in the presence of 0.1 mM G6P divided by the activity at 10 mM G6P) is used to indicate the active (dephosphorylated) fraction of the total GS activity pool. The protein content of homogenates for glycogen and glycogen synthase is quantified with the Bio-Rad protein assay kit (which is based on the Bradford method with a standard of bovine serum albumin).

Cardiac Outcomes

Cardiac outcomes includes myocardial infarction as defined by the Minnesota code criteria and the need of mechanical circulatory support, i.e. the insertion of an intra-aortic balloon pump. Also recorded are the patients's length of stay in the ICU. A length of stay greater than 30 hours is considered relevant. Research personnel blinded to treatment group and not participating in the care of patients collected postoperative data daily.

Statistics

The sample size is calculated based on expected changes in the cTnI concentration at 24 hours postoperatively. For a power of 0.8 and a of 0.05, 50 patients in each group are sufficient to detect a difference of 5 ng/ml between the two groups. Postoperative cTnI values are evaluated using the unpaired t-test with Welch's correction for unequal variances. Hemodynamics, intracellular proteins, circulating concentrations of metabolic substrates and hormones are compared using two-way ANOVA. Post-test analysis is performed using the Bonferroni-Dunn test. Clinical complications are evaluated using Fisher's exact test. Statistical significance was accepted at P<0.05. All P values are two-tailed.

Results

One hundred patients were enrolled. One patient assigned to GIN therapy was excluded because the surgery was performed off-CPB. No significant intergroup differences regarding the patients' characteristics, co-morbidities and surgical data were observed (Table 7).

TABLE 7

Patient characteristics and surgical data.

| CHARACTERISTIC | GIN | CONTROL |
|---|---|---|
| age (yr) | 64 ± 11 | 66 ± 9 |
| gender (M/F) | 40/9 | 36/14 |
| weight at admission (kg) | 85 ± 19 | 78 ± 12 |
| BMI (kg/m$^2$) | 28.7 ± 5.9 | 27.6 ± 4.5 |
| diabetes | 20 | 20 |
| insulin treatment | 3 | 4 |
| no insulin treatment | 17 | 16 |
| $HbA_{1C}$ (%) | 6.3 ± 1.4 | 6.2 ± 1.1 |
| hematocrit (%) | 42 ± 6 | 41 ± 5 |
| creatinine (µmol/L) | 103 ± 36 | 122 ± 42 |
| duration of anesthesia (min) | 310 ± 64 | 318 ± 71 |
| duration of surgery (min) | 221 ± 50 | 233 ± 67 |
| duration of CPB (min) | 90 ± 33 | 100 ± 33 |
| duration of aortic cross clamp (min) | 74 ± 27 | 83 ± 27 |
| number of grafts | 3.3 ± 0.7 | 3.6 ± 0.9 |
| estimated blood loss (ml) | 576 ± 386 | 643 ± 545 |
| amount of CPB prime solution (ml) | 1375 ± 381 | 1489 ± 353 |
| amount of cardioplegia (ml) | 848 ± 335 | 875 ± 338 |

Values are mean ± SD.
CPB = cardiopulmonary bypass.
GIN: n = 49.
Control: n = 50.

Figure 2:
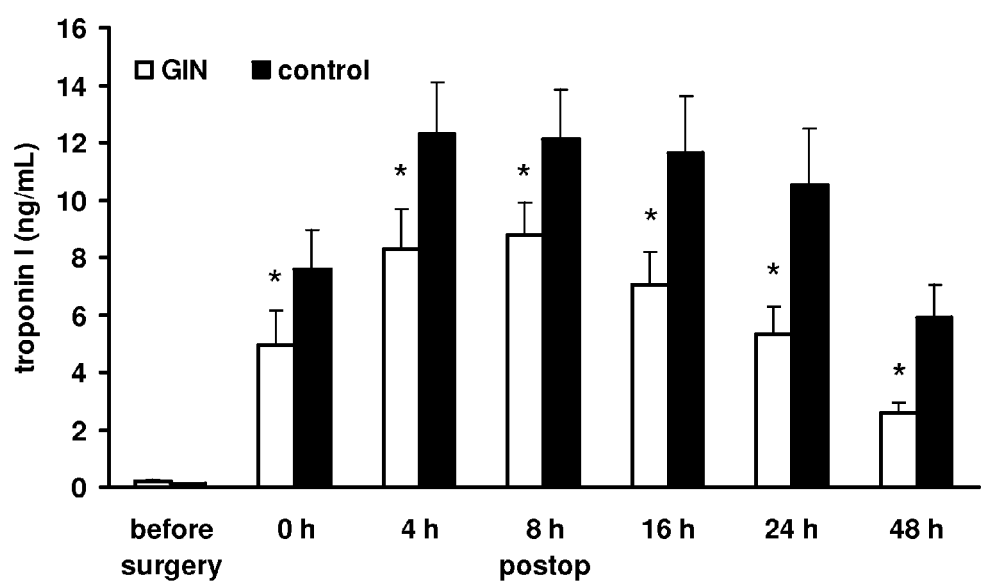
FIG. 2 illustrates plasma cTnI concentration in control (n=50) and GIN (n=49) groups according to an embodiment of the present invention. Values are mean±SEM. *P<0.05 vs. control.

There was no difference in systemic hemodynamic parameters (HR, MAP, CVP, PCWP, CI) between the groups. After surgery GIN therapy is accompanied by a lower MPI (GIN 0.47±0.17; control 0.57±0.24, P<0.01) indicating improved global myocardial function and a trend towards an increased FAC (preoperative: GIN 46±12%; control 49±11%; postoperative: GIN 55±11%; control 52±13%, P>0.05). Circulating epinephrine (preoperative: GIN 348±240 µmol/L; control 302±263 pmol/L, intraoperative: GIN 473±378 pmol/mL; control 345±225 pmol/mL), norepinephrine (preoperative: GIN 1773±1103 pmol/L; control 1448±889 pmol/L, intraoperative: GIN 2050±1644 pmol/mL; control 1508±1062 pmol/mL) and cortisol (preoperative: GIN 386±149 nmol/L; control 379±173 pmol/L, intraoperative: GIN 215±81 nmol/mL; control 194±89 nmol/mL) concentrations remained unchanged indicating comparable suppression of the endocrine response to surgery. The mean insulin plasma concentration is constantly above 3500 pm/L in the GIN group, while it remains under 100 pmol/L in the control group (P>0.0001). All patients in the GIN group are normoglycemic during surgery and no hypoglycemic event (blood glucose<3.5 mmol/L) is detected (FIG. 1). The GIN therapy attenuated the increase in circulating FFA in response to systemic heparinization and CPB, and is associated with complete suppression of FFA at the end of surgery (FIG. 1). Compared to patients in the control group patients receiving GIN had lower cTnI levels throughout the postoperative period (FIG. 2). Peak lactate concentration is less in the GIN group (GIN 2.3±0.7 mmol/L; control 3.6±2.3 mmol/L, P<0.001) and myocardial extraction of glucose and lactate is elevated as compared to the control group (Table 8).

TABLE 8

Arterial and coronary sinus concentrations of glucose and lactate.
Myocardial glycogen content and glycogen synthase activity.

|  | GIN | | CONTROL | |
| --- | --- | --- | --- | --- |
|  | Before CPB | After CPB | Before CPB | After CPB |
| glucose (mmol/l) | | | | |
| arterial | 5.01 ± 0.77 | 4.42 ± 0.48 | 6.70 ± 1.42 | 7.45 ± 1.39 |
| coronary sinus | 4.36 ± 0.73 | 3.95 ± 0.44 | 6.61 ± 1.47 | 7.23 ± 1.48 |
| arterial - coronary sinus | 0.65 ± 0.37 | 0.47 ± 0.25 | 0.09 ± 0.13* | 0.21 ± 0.18* |
| lactate (mmol/l) | | | | |
| arterial | 1.37 ± 0.42 | 1.70 ± 0.55 | 0.88 ± 0.29 | 1.26 ± 0.32 |
| lactate coronary sinus | 0.83 ± 0.34 | 1.56 ± 0.53 | 0.77 ± 0.21 | 1.43 ± 0.46 |
| lactate arterial - coronary sinus | 0.54 ± 0.21 | 0.14 ± 0.20 | 0.11 ± 0.27* | −0.17 ± 0.32* |
| glycogen content (μmol/g protein) | 0.338 ± 0.031 | 0.366 ± 0.047 | 0.335 ± 0.035 | 0.311 ± 0.030 |
| glycogen synthase activity | | | | |
| total activity (7.2 mM G6P) | 0.338 ± 0.031 | 0.366 ± 0.047 | 0.335 ± 0.035 | 0.311 ± 0.030 |
| active form (0.17 mM G6P) | 0.060 ± 0.008 | 0.106 ± 0.016* | 0.049 ± 0.007 | 0.110 ± 0.012* |
| fractional activity (active/total), % | 17.8 ± 2.4 | 30.3 ± 3.2* | 14.4 ± 1.5 | 36.9 ± 4.2* |

Values are mean ± SD.
*P < 0.01 versus GIN.
*P < 0.0001 versus before CPB.
GIN: n = 49.
Control: n = 50.

Figure 3:
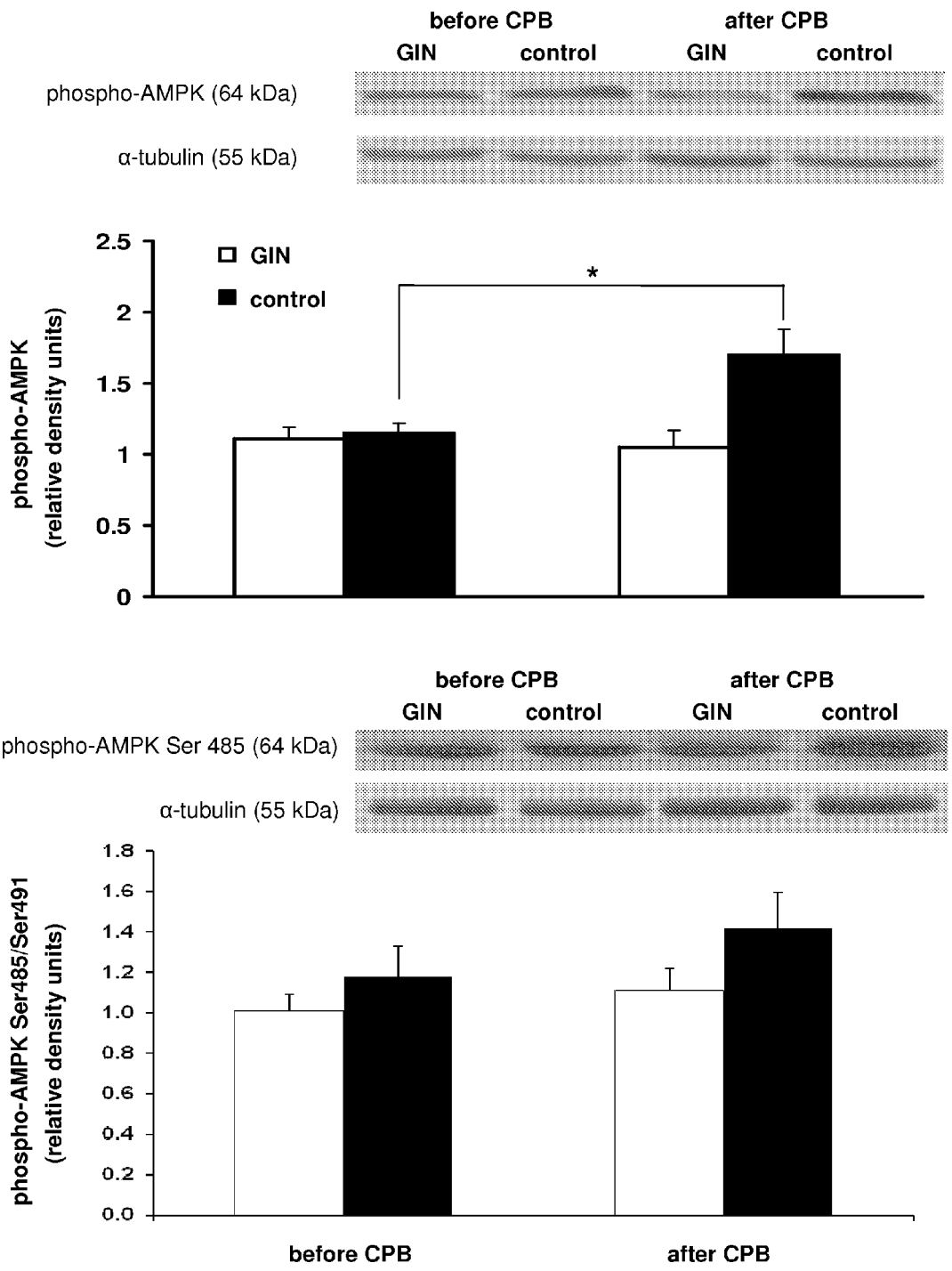
FIG. 3 illustrates AMPK phosphorylation levels (above) and AMPK phosphorylation levels on Ser 485/Ser491 (below) in control and GIN groups. Values were normalized for total AMPK levels. Results are mean±SEM from n=10 patients per group according to an embodiment of the present invention. *P<0.05 vs. before surgery.
Figure 4:
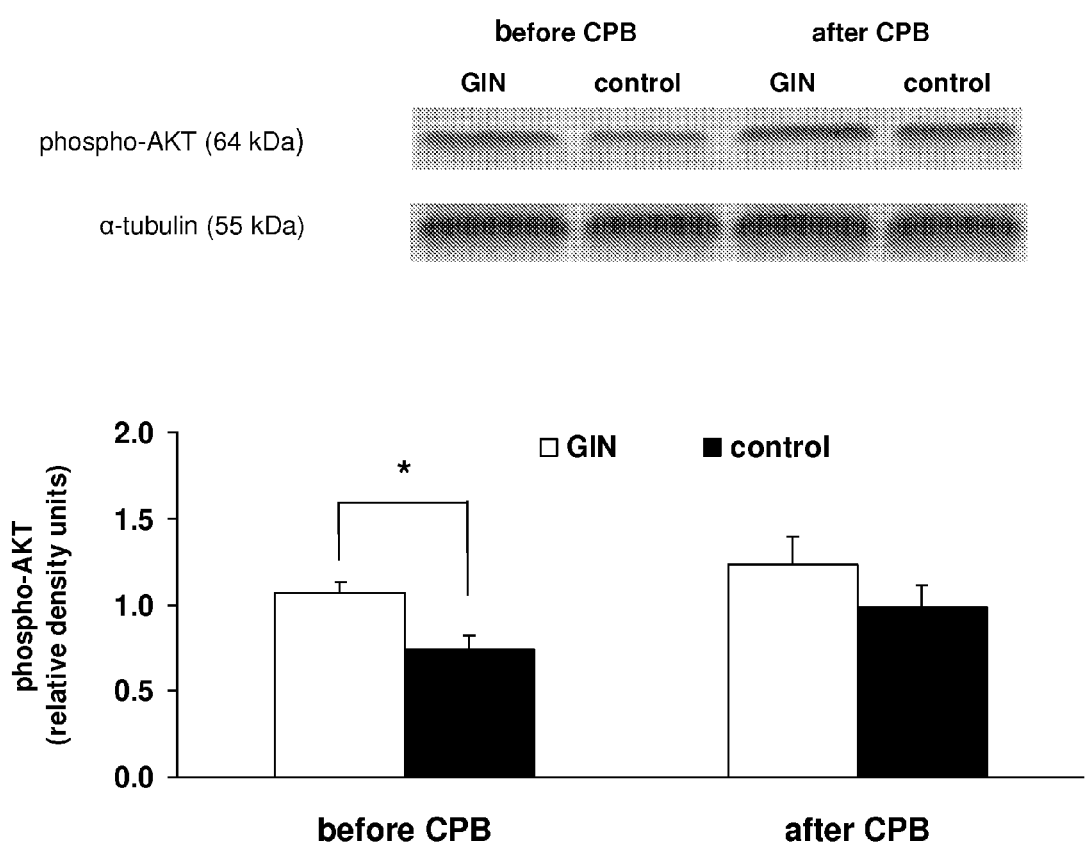
FIG. 4 illustrates Akt phosphorylation levels in control and GIN groups according to an embodiment of the present invention. Values were normalized for total Akt levels. Results are mean±SEM from n=10 patients per group. *P<0.05 vs control.

Intracellular glycogen content tended to be higher after CPB in the presence of GIN without showing statistical significance (Table 8). In all patients, the activities of the activated (dephosphorylated) form of glycogen synthase and the fractional velocity increased following CPB. The AMPK phosphorylation on Thr-172 was significantly increased after CPB in the control group, while it remains unaltered in the GIN group (FIG. 3). There is no evidence for increased Akt dependent Ser485/491 AMPK phosphorylation in the GIN group (FIG. 3). Patients receiving GIN therapy show a higher level of Akt phosphorylation on Ser-473 prior to CPB (FIG. 4). Cardiac Akt phosphorylation remains elevated after CPB but this is no longer different from that seen in control patients. In the control group ten patients suffered a MI and five patients required mechanical circulatory support. In contrast only three patients in the GIN group had a MI and one patient needed an intra-aortic balloon pump (P>0.05). A smaller number of patients in the GIN group required prolonged intensive care >30 hours (GIN 10 (20%); control 22 (44%), P<0.05).

The results of this example demonstrate that the perioperative administration of GIN, i.e. glucose and insulin while maintaining normoglycemia, has cardioprotective effects in humans undergoing surgical coronary revascularization. These benefits appear to be mediated through the suppression of ischemia induced AMPK activation during ischemia-reperfusion.

Patients after CABG and CPB demonstrate a significant elevation in the plasma levels of cardiac biomarkers which typically peak within 12 hours after surgery. The GIN therapy is associated with lower cTnI concentrations when compared to standard metabolic care suggesting intraoperative cardioprotection and a lesser extent of ischemic myocardial injury. Echocardiographic data in the present example further demonstrate improved global cardiac function in the presence of GIN, presumably causing the lower incidence of myocardial ischemia and heart failure requiring mechanical support after surgery. Animal studies demonstrate that the provision of glucose for glycolysis and ATP synthesis as well as the maintenance of normoglycemia are required to produce such inotropic effects of high doses of insulin. A clinical trial evaluating the effect of low dose insulin therapy without establishing normoglycemia found no cardiac risk reduction.

In cardiac surgery, the obligatory administration of large amounts of heparin stimulates lipoprotein lipase leading to a massive release of FFA into the circulation. Insulin is a potent inhibitor of lipolysis and, therefore, limits FFA availability for oxidation. This transition in fuel utilization from FFA to glucose has been proposed as one mechanism underlying improved cardiac recovery with insulin therapy. The FFA levels are normalized in the insulin therapy group at the end of CPB and completely suppressed by the end of surgery. Free fatty acids when used as the main myocardial energy source during reperfusion, are known to delay post-ischemic functional recovery, provoke endothelial dysfunction, impair endothelium-dependent coronary vasodilation and calcium homeostasis, and stimulate free radical production. High levels of FFA accumulate as toxic fatty acid derivatives that depress myocardial contractility and induce arrhythmias. Compared with glucose metabolism, FFA oxidation is less efficient and stimulates myocardial oxygen consumption without a concomitant increase in myocardial performance. Activation of the AMPK pathway is believed to play a major role in this shift towards lipid oxidation in the ischemic myocardium especially in the presence of high levels of FFA. Low-flow ischemia followed by reperfusion has been identified as a potent trigger of AMPK activation in cardiomyocytes. In the control group, elevated AMPK activity combined with enhanced FFA availability probably resulted in the use of FFA as the primary energy source. The combined effect of insulin therapy to limit FFA availability and AMPK activation likely provided cardioprotection through enhanced reliance of glucose as a the main fuel source. The enhanced myocardial arterial-coronary sinus differences for glucose and lactate indicating myocardial uptake of glucose and lactate as demonstrated in the present protocol corroborate this assumption. Several studies emphasize the importance of the timing of insulin therapy in relation to myocardial ischemia. It is not clear whether pre-ischemic therapy, therapy initiated during ischemia or at reperfusion provides the best-quality cardioprotection. The ability of insulin to blunt AMPK activation during ischemia so far has only been observed when insulin was administered prior to the anaerobic episode. Interestingly, at is observed that increased cardiac Akt activation by insulin during the pre-CPB period (i.e. before AMPK phosphorylation is modulated). Insulin therapy in our protocol starts on arrival to the operating theatre andis maintained for at least 60 minutes before CPB, thereby providing time to overcome surgery-induced insulin resistance, favour myocardial glucose utilization and, potentially, allow stimulation of Akt which can further prevent AMPK activation during CBP. One mechanism by which insulin action inhibits AMPK activation is through Akt-dependent inhibitory phosphorylation of the AMPK subunit on Ser485/491. Although AMPKa Ser485/491 phosphorylation was detected, it is not associated with Akt activation (based on its phosphorylation status) suggesting that, in cardiac muscle, other kinases may phosphorylate this site. Because insulin promotes glycogen synthesis and AMPK inhibits this energy consuming process, glycogen repletion in the presence of GIN is expected. Indeed, there is a trend for increased glycogen content pre-CPB in the GIN group, while a small decrease in glycogen content occurred in the control group after CPB. The timing of biopsies may have influenced these results. The second biopsy is performed at the end of CPB 10 to 15 minutes after release of the aortic cross-clamp. During this critical time of reperfusion subjects' hearts are exposed to non-pulsatile flow of systemic blood followed by a few minutes of partial pulsatile flow until separation from CPB. In the control group, elevated blood glucose, by mass effect, may have stimulated glycogenesis. Furthermore, myocardial glycogen synthesis has been shown to increase in the absence of stimulated glucose uptake if lactate is available. This, however, seems unlikely as the lactate arterial-venous difference in the control group is negative, suggesting lactate production by the myocardium. Hence, in agreement with recent observations, insulin-mediated cardioprotection in the present study cannot be explained by modulation of myocardial glycogen levels.

In summary GIN therapy provides cardioprotection and reduces myocardial morbidity after CABG, most likely a consequence of preserved myocardial energy balance during ischemia-reperfusion injury, an effect mediated by the suppression of ischemia-induced AMPK activation.

Example 7

GIN Therapy on Patients Undergoing a Major Liver Resection 60 patients are included in the study. Exclusion criteria included all patients with type 1 Diabetes Mellitus, uncontrolled blood glucose levels (fasting level>180 mg/dL), known chronic liver disease (Child-Pugh B or C) or renal failure (need for dialysis), patients with significant anemia (<10 g/dL), patients on oral beta-blockers, calcium-channel blockers, or acetylsalicylic acid, or patients undergoing a simultaneous resection of other viscera.

Protocol

Randomization is carried out with the assistance of an independent randomization center blinded to the study and orchestrated by the study coordinator, after obtaining consent. The surgical team is not involved in the randomization process.

The study coordinator collects and stores all data. Data collection and accuracy are double checked by an independent clinical research assistant. All demographics, operative data, and postoperative variables including glucose levels, degree of hepatic steatosis, steatohepatitis and fibrosis, complications, and divergence from the postoperative care pathway are collected prospectively.

Fluid and Insulin Management:

Control Group

Patients are fasted from midnight onward except for water and medications. IV normal saline (NS 0.9%) infusion is started just before anesthetic induction, and titrated to hemodynamic parameters and urine output. Arterial-blood glucose levels are checked at induction, and every 30 min thereafter with an Accu-Chek® glucose monitor (Roche Diagnostics, Switzerland). A blood glucose level above 110 mg/dL is treated with a 2 U bolus of IV insulin (Humulin® R regular insulin, Eli Lilly and Company, Indianapolis, Ind.) followed by a 1 U/hour drip infusion adjusted according to a standard sliding scale. Patients are cared for in a step-down unit for the first 24 hours (Table 9).

TABLE 9

Standard Step-down Unit Insulin Infusion Sliding Scale

| If blood glucose mg/dL | Action |
|---|---|
| <63 | Stop insulin infusion. Give dextrose 20% (D20W ®) 10 ml infusion and re-check level in 10 min |
| 63.0-143.0 | Maintain current infusion rate |
| 144.0-180.0 | Increase insulin infusion by 1 units/hour |
| >180.0 | Increase insulin infusion by 2 units/hour |

Study Group

Study patients are instructed by a clinical dietician to follow a clearly written dietary regimen on the day (24 hours) prior to surgery. The three meals are composed of food elements tailored to each patient. The meals provided 35 kcal/kg (ideal body weight) of which 60% is carbohydrate, 20% fat, and 20% protein. Meals are spaced 5-hours apart, and patients ate their last meal at 7 pm. Compliance is checked by the study dietician. Patients who failed to complete their diet as instructed are requested at the clinical dietician's discretion to compensate with food supplements at suppertime. At 8 pm, patients began receiving IV dextrose 10% (D10W®) infused at a rate of 2 mg/kg/min (ideal body weight). Blood glucose levels are checked every 3 hours during the dextrose infusion. Subcutaneous insulin (Humulin® R regular insulin, Eli Lilly and Company, Indianapolis, Ind.) is administered when needed to maintain blood glucose between 72-180 mg/dL as per a sliding scale. In the operating room, the blood glucose level is checked after the insertion of the epidural catheter and prior to intubation. A 2 U bolus of IV insulin is given followed by an IV infusion of 2 mU/kg/min (0.12 U/kg/hour). Dextrose 20% (D20W®) is started when arterial-blood glucose levels fell below 110 mg/dL and then is titrated to maintain blood glucose between 63-110 mg/dL. Blood glucose levels are measured at 5-10 min intervals with an Accu-Chek® glucose monitor (Roche Diagnostics, Switzerland) to ensure euglycemia. Caution is exercised at the time of parenchymal transection and during transfusion of blood products. Following surgery, the insulin infusion is reduced to 1 mU/kg/min (0.06 U/kg/hour) and continues at the step-down unit to complete the 24 hours of insulin therapy. After the operation, the arterial blood glucose level is checked every 60 min and the dextrose infusion was adjusted as per a given sliding scale. In the event that a study patient receives a blood product, the blood glucose level is checked every 30 min during the transfusion. After 24 hours, the insulin therapy is stopped and the dextrose infusion is weaned off over 30 min. Diabetic patients resumed their preoperative treatment. Normal saline (NS 0.9%) infusion is given and adjusted to hemodynamic parameters and urine output (Tables 10, 11, 12).

TABLE 10

Subcutaneous Insulin Sliding Scale for Study Patients Prior to Surgery

| Blood glucose level | Insulin dose | Additional instructions |
|---|---|---|
| <72 mg/dL | None | Call on-call MD |
| 73.0-180.0 mg/dL | None | |
| 181.0-216.0 mg/dL | 2 units | |
| 217.0-260.0 mg/dL | 4 units | |
| 261.0-288.0 mg/dL | 6 units | |
| 280.0-325.0 mg/dL | 10 units | |
| 330.0-360.0 mg/dL | 12 units | |
| >360 mg/dL | 14 units | Call on-call MD |

TABLE 11

Standard Insulin Infusion Sliding Scale While in the Operating Room

| If blood glucose mg/dL | Action |
|---|---|
| <63 | Stop insulin infusion. Give dextrose 20% (D20W ®) 10 ml infusion and re-check level in 10 min |
| 63.0-110.0 | Maintain current infusion rate |
| 111.0-143.0 | Increase insulin infusion by 1 unit/hour |
| 144.0-180.0 | Increase insulin infusion by 2 units/hour |
| >180.0 | Increase insulin infusion by 3 units/hour |

TABLE 12

Dextrose Sliding Scale During the Insulin Infusion in the Postoperative Period

| Blood glucose level mg/dL | Dextrose infusion | Additional instructions |
|---|---|---|
| <63 | ↑ D20W by 15 ml/h, and give 20 ml of D20W bolus | Call research MD on-call |
| 63.0-74.0 | ↑ D20W by 10 ml/h, and give 10 ml of D20W bolus | |
| 75.0-81.0 | ↑ D20W by 5 ml/h | |
| 82.0-98.0 | Maintain same rate | |
| 99.0-110.0 | ↓ D20W by 5 ml/h | |
| 111.0-116.0 | ↓ D20W by 10 ml/h | |
| >126 | ↓ D20W by 50% | Call research MD on-call |

Operative Details and Liver Samples:

All patients receive preoperative antibiotic and anti-thrombosis prophylaxis. Diabetic patients on oral hypoglycemics are asked to discontinue their therapy 24 hours prior to surgery, and those on insulin are asked to omit their evening dose. Anesthesia induction and maintenance, including the use of epidural analgesia, are according to standard protocols. Phenylephrin is given to patients with low intraoperative blood pressure. Perioperative steroid and dextrose containing solutions are not used.

The first liver biopsy (300 mg) is taken with a knife from the FLR after completion of the liver mobilization and the intraoperative ultrasound but prior to parenchymal transection. The transection is performed with the ERBE Helix Hydro-Jet® locking plastic clips and Endo-GIA staplers. Vascular inflow occlusion is rarely employed and only for hilar lesions. A second liver sample (300 mg) is taken after completing the resection, again from the FLR. The time of sample collection is documented relative to the time of skin incision.

Liver samples are snap frozen in liquid nitrogen within 5 min of procurement and stored at −80° C. until processed. Glycogen content in the liver sample is determined by subjecting it to acid hydrolysis with 1M HCl at 100° C. for 3 hours, neutralizing the extracts with 2M TRIS-KOH then assaying the supernatant for glucose using a Glucose Assay Kit (Sigma®). Liver triglycerides (TG) are extracted overnight at 4° C. from 30-50 mg of liver tissue using a heptane/isopropanol solution (3:2). TG content of the transferred extract is measured using a commercial colorimetric kit (Roche Diagnostics®). The remaining tissue is air dried, dissolved in 0.3N NaOH and assessed for protein content using the Bradford method (Bio-Rad, Mississauga, ON, Canada). Results are expressed as pmoles of TG per gram (g) of protein.

Postoperative Clinical Pathway

Patients are given clear liquids on their first postoperative day, followed with regular diet within 24 hours as tolerated. Normal Saline (NS 0.9%®) is used for IV hydration in the first 24 hours until tolerance of oral intake. Patients are discharged when tolerating a solid diet and not requiring nursing assistance. Drains are removed on postoperative day 2 unless a bile leak is detected in which case removal is delayed until the leak stopped.

Assessments and Tests

Serum and plasma samples are taken immediately preceding skin incision, just prior to parenchymal transection, after abdominal closure, and 24 hours after surgery. The arterial lactic acid, base deficit, venous insulin glucagon, and human IL-1β, IL-6, IL-8, IL-10, MCP-1 and TNF-α are measured from these samples. Cytokines are analyzed by suspension bead array immunoassay using a Luminex 200 X-map instrument (Luminex Corp, Austin, Tex., USA). The cytokines are measured using a Milliplex human cytokine kit following manufacturer's specifications (MPXHCYTO-60k, Millipore Corp, Bilerica, Mass., USA). All samples are measured in duplicate and the kit had a sensitivity of 0.4 pg/ml.

Additional samples are taken at 30 days before surgery (or at least three weeks after their last cycle of chemotherapy, in patients receiving preoperative therapy), and 6 h, 12 h, 24 h, 48 h, 72 h, 7 days and 30 days postoperatively to monitor complete blood count, liver enzymes and function test, coagulation profile, albumin, fibrinogen, pre-albumin, electrolytes, fasting serum blood glucose, renal function, CRP (C-reactive protein), and cortisol levels. A liver volumetric analysis is performed on all patients with a triphasic CT-scan at least 6 weeks prior to surgery or 3-4 weeks after a portal vein embolization. Standardized total liver volume (TLV) and future liver remnant (sFLR) are calculated.

Definitions of Outcomes

Liver glycogen measured from liver biopsies as described above, and expressed as pmoles of glucose per gram (g) of liver wet weight. Postoperative liver function is scored using the system developed by Schindl et al. (Schindl M et al. 2005, Archives of Surgery 140(2):183-189). This system grades liver dysfunction according to the levels of lactic acid, total bilirubin, INR and encephalopathy (Table 13). Total scores of 0, 1-2, 3-4, or >4 are used to classify liver dysfunction as absent, mild, moderate or severe, respectively. Surgical morbidity in the 30 days following the operation are ranked as per Clavien (Dindo et al. 2004, Annals of Surgery 240(2):205-213). Morbidities are classified as either infectious or non-infectious (Table 14).

TABLE 13

Liver Function as Per Score Generated by Schindl et al□

| | Total serum bilirubin (μmol/L) | | |
|---|---|---|---|
| | <20 | 20-60 | >60 |
| Prothrombin time (INR) | <4.0 (1.8) | 4.0-6.0 (1.8-2.3) | >6.0 (2.3) |
| Serum lactate (mmol/L) | <1.5 | 1.5-3.5 | >3.5 |
| Encephalopathy grade | None | 1 and 2 | 3 and 4 |
| Given points | 0 | 1 | 2 |

□No dysfunction when score equal to 0 points, mild when 1-2, moderate when 3-4, and Severe dysfunction when >4 points.

TABLE 14

Criteria for Classifying Morbidities as Infections or Noninfectious

| | Description |
|---|---|
| Noninfectious Characteristic | |
| Blood Glucose | >10 mmol/L (hyperglycemia) |
| | <2 mmol/L (hypoglycemia) |
| PONV | Persistent beyond day 2 postoperative |
| Bleeding | Requiring surgical intervention |
| | Hemoglobin drop >4 mg/dL |
| Cardiac event | Symptomatic arrhythmia |
| | Blood troponin >0.5, with ECG changes |
| Pleural effusion | Tapping required for patient relief |
| Abdominal | Ascites: dyspnea or leaking through abdominal wall |
| Acute renal failure | Serum creatine >2 × upper limit of normal |
| Bile leak | Body fluid bilirubin content >2 × upper limit of serum level |
| Infectious Characteristic | |
| Pneumonia | Pneumonic or atelactic changes on chest radiographs with positive sputum culture |
| Wound infection | Erythema and indurations associated with positive bacterial culture |
| Intra-abdominal abscess | Collection of pus in the abdomen with or without necrotic material associated with a positive bacterial culture |
| Urinary tract infection | Urinary symptoms with urine culture positive for bacterial growth >105 colony forming units/ml |
| Central line sepsis | Positive culture of the catheter tip >15 colony forming units in the presence of a febrile episode |

PONV: postoperative nausea and vomiting

Statistics:

The data are expressed as means±SD or medians and range if not normally distributed. Demographic, operative and postoperative variables are compared using the unpaired t-test or Mann-Whitney U test for continuous data. Proportions are compared by the Chi-square or Fisher Exact tests.

Since a large number of study variables are collected (174) the principle component analysis (PCA) method of multivariate analysis was applied to reduce the 174 study variables to a smaller set of uncorrelated variables that capture most of the information (variance) in the original data. Missing values are replaced with the mean. The PCs are rotated using an orthogonal rotation-varimax normalized. Only the components that extracted at least as much variance as the equivalent of 5 original variables (eigenvalues greater than or equal to 5) are retained. Sample factor scores (values) for each component are saved and used in a subsequent logistic regression analysis.

A P-value less than or equal to 0.05 was considered significant. All analyses were done using the Statistica version 9 statistical package.

Results

Figure 5:
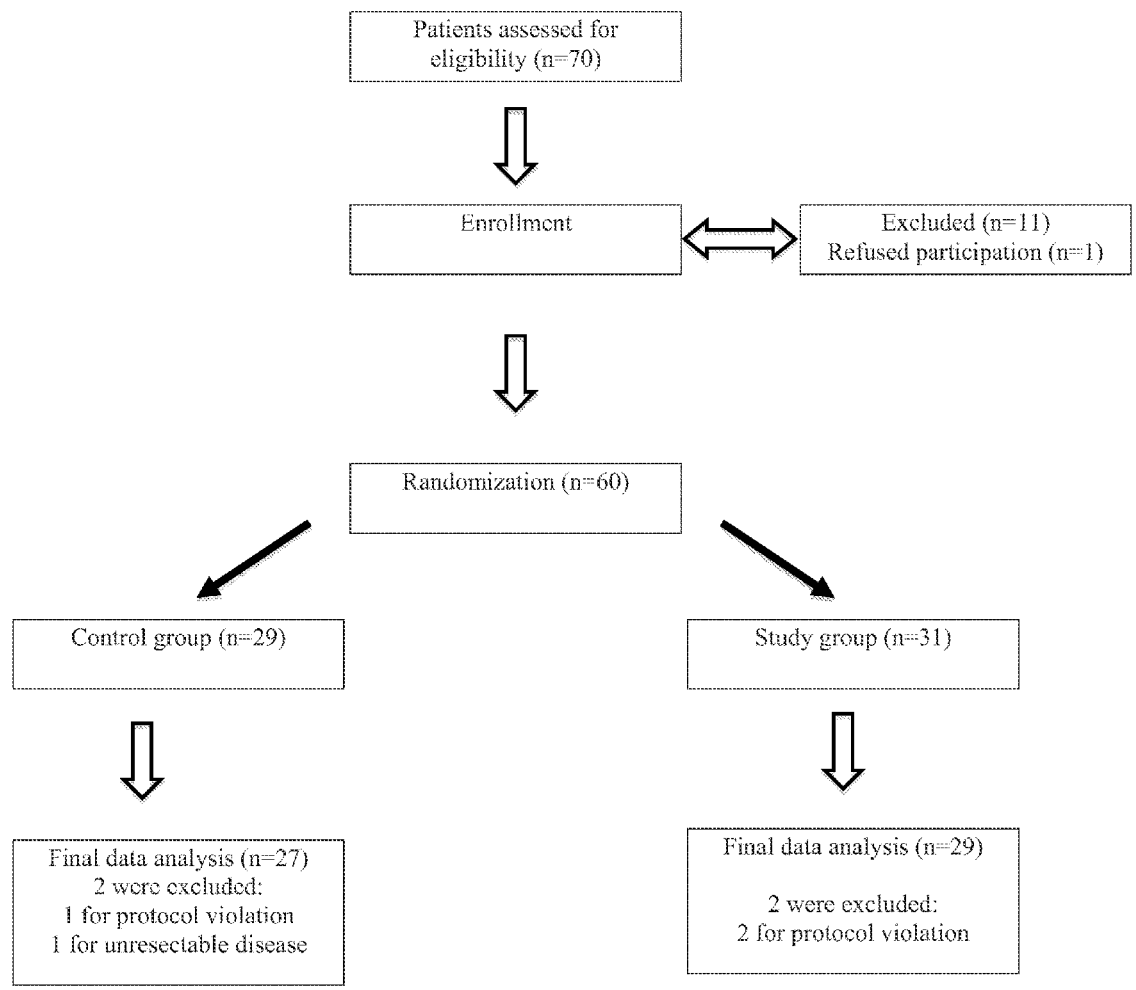
FIG. 5 illustrates a patient distribution. Seventy patients are assessed for eligibility for the study and 60 are randomized. After randomization, 4 patients are excluded, 1 for unresectable disease and 3 for protocol violations.

Sixty of the 70 patients assessed for eligibility are randomized to the protocol including 31 patients in the insulin therapy group (study group) and 29 patients in the control group. 4 patients are excluded: 1 patient is unresectable and 3 had protocol violations; 2 study patients have not received their preoperative IV treatment due to hospital bed shortage, and 1 control patient received IV steroid at induction (FIG. 5). There is no significant difference in patient demographic, preoperative and operative data between the 2 groups (Table 15).

TABLE 15 a) General Demographics and Preoperative Characteristics of Patients in Control and Study Groups

| Variables | Control group N = 27 | Study group N = 29 | P-value |
|---|---|---|---|
| Age (years) | 55.8 (29-87) | 64.8 (41-85) | 0.09 |
| Gender (males, n %) | 16 (59) | 12 (41) | 0.17 |
| Diabetes Mellitus, n (%) | 7 (26) | 7 (24) | 0.26 |
| Hypertension, n (%) | 3 (11) | 7 (24) | 0.20 |
| Heart disease, n (%) | 0.0 (0.0) | 3.0 (10.3) | 0.086 |
| Hyperlipidemia, n (%) | 1.0 (3.7) | 2.0 (6.8) | 0.59 |
| Body mass index kg/m2 | 26.5 (19.6-35.2) | 25.5 (18.8-30.8) | 0.94 |
| Baseline lactic acid (mmol/L) | 0.8 (0.4-1.9) | 0.6 (0.1-1.4) | 0.84 |
| Baseline total bilirubin (μmol/L) | 15.0 (7.5-121.0) | 13.0 (8.0-133.0) | 0.83 |
| Baseline INR | 1.0 (0.9-1.9) | 1.0 (0.9-1.9) | 0.37 |
| Baseline creatinine (μmol/L) | 73 (53-117) | 72 (45-117) | 0.55 |

Data are expressed as n (%) or median (with range).

TABLE 15 b) Operative Characteristics of Patients in Control and Study Groups

| Characteristics | Control group N = 27 | Study group N = 29 | P-value |
|---|---|---|---|
| Re-hepatectomy, n (%) | 3 (11) | 6 (20.6) | 0.33 |
| Trisegmentectomy, n (%) | 6 (22) | 11 (38) | 0.20 |
| Duration of NPO (hours) | 13.5 (8.5-21.0) | 12.0 (9.0-18.0) | 0.26 |
| Number of segments resected | 4 (3-5) | 4 (3-6) | 0.49 |
| Total liver volume (ml) | 1623 (1064-2082) | 1626 (1013-2130) | 0.06 |
| Standardized FLR (%) | 44 (21-84) | 39 (17-88) | 0.92 |
| OR duration (hours) | 3.0 (2.3-6.0) | 3.0 (1.5-7.0) | 0.44 |
| Number of Pringles, n (%) | 1.0 (3.7) | 3.0 (10.3) | 0.4 |
| Pringles duration (min) | 18.00 ± 6.02 | 19.00 ± 5.32 | 0.76 |
| Blood loss (ml) | 1425 (500-5325) | 1155 (400-3400) | 0.11 |
| Blood transfusion, n (%) | 11.0 (40.7) | 12.0 (41.4) | 0.97 |
| Blood transfusion (unit) | 0.0 (0.0-8) | 0.0 (0.0-4) | 0.72 |
| Crystalloid (L) | 3.0 (1.0-6.0) | 3.0 (0.5-5.5) | 0.15 |
| Colloid (L) | 1.0 (0.0-1.5) | 1.0 (0.0-1.0) | 0.80 |
| Fibrosis grade (0-4) | 0.0 (0.0-4.0) | 0.0 (0.0-3.0) | 0.26 |
| Steatohepatitis grade (0-8) | 0.0 (0.0-4.0) | 0.0 (0.0-2.0) | 0.44 |

Data are expressed as n (%) or median (with range).

Figure 6:
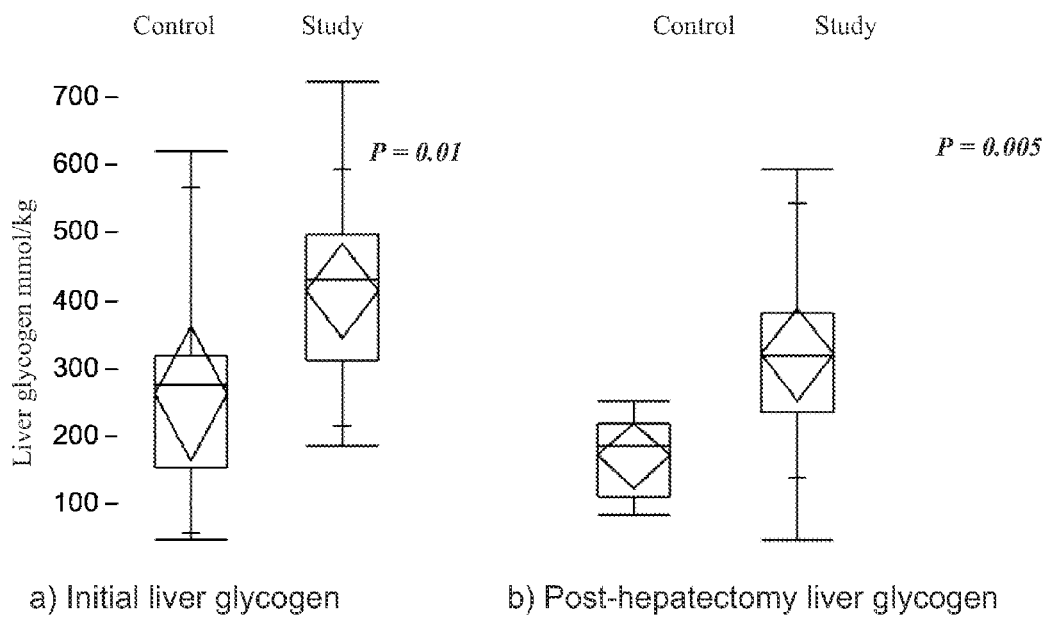
FIG. 6 illustrates a Quantile box plots for results from tissue analysis of patients in control and study groups according to an example of the present invention: (a) initial liver glycogen median (mmol/kg×$10^{-1}$) (P=0.01); (b) posthepatectomy liver glycogen median after hepatectomy (mmol/kg×$10^{-1}$) (P=0.005)
Figure 7:
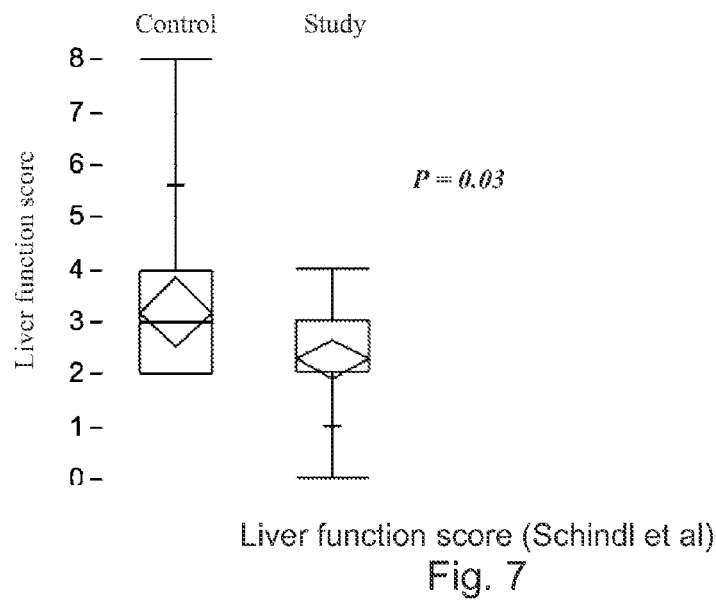
FIG. 7 illustrates a Quantile box plots for liver function score (Schindl et al) of patients in control and study groups (P=0.02).

Primary Outcomes:

Measurements relating to the study's primary outcome are summarized in FIGS. 6 and 7 (Table 14). Patients on protocol have increased liver glycogen content before and after resection compared to the control patients (430 (188-722) and 306 (37-580) vs. 278 (48-620) and 187 (83-255) mmol/kg, P-value of 0.01 and 0.005 respectively) and demonstrated less POLD according to Schindl Scores, 2 (0-4) vs. 3 (2-8), P-value of 0.03 (FIGS. 6 and 7). Sample timing and other tissue analyses did not reveal any significant difference.

Secondary Outcomes:

The protocol achieves a significant reduction in overall complications and in postoperative infections. The incidence of complications decreases from 26% to 17%, while the overall infectious complication rates were 14% and 8% in study and control groups, respectively. Infections of Clavien grade 2 or higher occurred in 11% of patients in the control group and none in the study group. There is no mortality in either group (Table 16).

TABLE 16

Distribution of Complications between Study and Control Groups

| Complication | Type of complication | Study group (n) | Degree as per Clavien for each patient | Control group (n) | Degree as per Clavien for each patient |
|---|---|---|---|---|---|
| Non-infections | PONV | 2 | 1, 3 | 5 | 1, 1, 1, 1, 1 |
| | Ascitis/Plural effusion | 2 | 3, 1 | 2 | 1, 3 |
| | DVT | | | 1 | 4 |
| | Bile leak | 2 | 1, 1 | 3 | 1, 1, 1 |
| | ARF | 2 | 1, 1 | 1 | 4 |
| | Cardiac event | 1 | 3 | | |
| Infections | Wound infection | 5 | 1, 1, 1, 1, 1 | 4 | 1, 1, 3b, 1 |
| | Central line infection | | | 3 | 2, 2, 2 |
| | UTI | 2 | 1, 1 | 2 | 1,1 |
| | Pneumonia | | | 1 | 2 |
| | Intra-abdominal abscess | 1 | 3 | 1 | 2 |
| | Other | | | 3 | 4, 2, 2 |

PONV: postoperative nausea and vomiting,
DVT: deep vein thrombosis,
ARF: acute renal failure,
UTI: urinary tract infection Blood Glucose:

Patients have statistically lower blood glucose levels while receiving insulin therapy, (Table 2). The statistical difference persists regardless of whether the patient is diabetic or not. The study group patients have reached targeted blood glucose levels more often and experience fewer fluctuations compared to the control group, P=0.03 and 0.04 respectively.

TABLE 17

Blood Glucose Level Comparison at Different Time Intervals

| Blood Glucose level mg/dL | Control N = 27 | Study N = 29 | P-value |
|---|---|---|---|
| At baseline | 97.0 (76-270) | 99.0 (68-167) | 0.17 |
| Prior to surgery | 113.0 (76-264) | 112.0 (72-180) | 0.51 |
| Intraoperative | 135.0 (97-247) | 81.0 (42-142) | <0.001 |
| Postoperative 48 hours | 121.0 (73-162) | 119.0 (77-261) | 0.12 |
| Postoperative 7 days | 162.0 (73-180) | 115.0 (81-198) | 0.41 |
| Postoperative 30 days | 108.0 (81-229) | 95.0 (54-198) | 0.13 |

Data are expressed as median (with ranges).

Blood glucose levels measured at baseline, prior to surgery; and at 48 hours, 7 days, and 1 month post surgery are statistically similar between the 2 groups. None of the study group patients experienced a very high (>180 mg/dL) or very low (<40 mg/dL) blood glucose level. One patient in the control group developed a very low (36 mg/dL) level. There are 7 other control patients with at least 10 high blood glucose readings (mean 207 (185-270) mg/dL).

Multivariate Analysis:

PCA extracts 10 components from the data. The proportion of variance accounted for by these factors is approximately 52%. Of these 10 components, only PC1, PC3, PC6 and PC9 are determined to be independently associated with study intervention, infection or complications via logistic regression analysis (Table 18). The beta coefficients indicate the relative strengths of the associations in each analysis. PC1 contained postoperative levels of ALK, GGT, platelet count and serum IL-8 and may be interpreted as liver repair activity. It is positively associated with study intervention (Beta=3.10). PC3 consists of perioperative blood glucose levels. Higher glycemic levels correlated negatively with the study intervention (Beta=−4.27). PC9 contained FLR volume and higher FLR correlated negatively with the intervention (Beta=−1.13). PC6 contained markers of POLD, total bilirubin, INR, and IL-6. The interaction variables suggested that the association between intervention and liver repair activity is blunted by either a rise in glycemic levels or an increase in residual liver volumes. POLD and higher glycemic levels associated positively with infection (Beta=1.99 and 1.49, respectively) but only higher glycemic levels are associated with all complications (Beta=0.64).

TABLE 18

The independent Associates of Intervention, Infections and All Complications in Total Patient Group

| Dominant content of each PC | Beta (Exp beta) | P-value |
|---|---|---|
| Associates of intervention | | |
| PC1. Higher liver repair activity | 3.19 (24.29) | 0.014 |
| PC6. Higher glycemic levels | −4.27 (0.01) | 0.001 |
| PC9. Higher residual liver volumes | −1.13 (0.32) | 0.071 |
| PC1*PC6 | 3.68 (39.65) | 0.024 |
| PC1*PC9 | 2.99 (19.89) | 0.073 |
| Associates of all infection | | |
| PC3. POLD | 1.986 | 0.025 |
| PC6. Higher glycemic levels | 1.488 | 0.004 |
| Associates of all complications | | |
| PC6. Higher glycemic levels | 0.639 | 0.042 |

The collected variables were transformed into 10 principal components (PC). P-values and beta coefficients are presented from a forward stepwise logistic regression run.

Certain groups of low yield laboratory test values are missing in up to 50% of the total values, completely at random. Missing data points are replaced with variable means. Replacing values with means is the most conservative course for assessing the data, short of dropping cases from analysis; but may restrict emergence of potential findings and/or data relationships by decreasing variability and item correlations.

Perioperative dextrose supplementation augments liver glycogen stores and provides a protective effect on the hepatocyte, but when administered alone may compound hyperglycemia and increase postoperative morbidity. Tight-glucose control reduces postoperative morbidity, but also causes significant hypoglycemic complications and mortality. Insulin therapy with a hyperinsulinemic normoglycemia protocol (GIN) according to the present invention counteracts both these effects by sustaining serum glucose homeostasis, inhibiting liver glycogen and inhibiting peripheral fat breakdown. There is evidence that it may also exert an anti-apoptotic effect on hepatocytes and decrease inflammation. According to the present example, the patients on the insulin therapy according to the present invention have significantly lower blood glucose levels, and experienced fewer fluctuations, with no incidence of severe hypoglycemia (Table 17). Our protocol thus permits replenishment of liver glycogen stores while maintaining normoglycemia, limiting the complications associated with hyperglycemia. Study patients in our trial also exhibited a lower rate of morbidity (there was no mortality).

In-vivo studies have demonstrated a linear relationship between liver glycogen content and liver function. Glycogen is essential for maintaining hepatocellular integrity and functions by supplying glucose for ATP generation. ATP depletion leads to a series of events causing cell injury and necrosis that can be reversed with glucose supplementation. The protocol according to the present invention achieved a significant increase in liver glycogen content and reduced POLD compared to standard glucose management (FIGS. 6 and 7). This intervention also decreased the postoperative complication rates (P-value 0.004) and held true for the infectious subset of complications (P-value 0.04) (Table 18).

Normal liver function is important for keeping metabolic and immune system functions intact. Failure of the liver to regenerate and/or insufficient functional FLR following surgery leads to POLD and increases the likelihood of postoperative infections and mortality. A strong parallel is observed between infection complications and both POLD and higher glycemic levels (Table 18). The protocol according to the present invention reduces the incidence of postoperative infection likely because it improves both POLD and glycemia control. Increase in liver repair activity from insulin therapy is also enhanced by both good glycemic control and smaller FLR's (i.e. Larger volume LRs), which is consistent with in-vivo findings.

Both glycemia control and hepatocellular glycogen level maintenance are necessary factors in maintaining hepatocellular integrity, and function during LR. The protocol according to the present invention reduced POLD and increased liver glycogen content by maintaining a balance between these 2 factors (FIGS. 6 and 7). Results from this trial therefore, emphasize the importance of tight-glucose control for improving FLR function.

The present example demonstrates that the glucose/insulin (GIN) protocol according to the present invention achieves elevation in liver glycogen content, improves postoperative liver function and reduces overall postoperative complication rates for patients undergoing major liver resection. The protocol appears to be safe and can be easily applied at a step-down setting.

TABLE 19

Tissue Analysis of Patients in Control and Study Groups

| Characteristics | Control group N = 27 Median | Range | Study group N = 29 Median | Range | P-value |
| --- | --- | --- | --- | --- | --- |
| Liver sample 1 time (hours from skin incision) | 1.0 | 0.5-3.0 | 1.1 | 0.5-3.4 | 0.88 |
| Liver sample 2 time (hours from skin incision) | 2.8 | 1.5-5.5 | 2.8 | 1.0-6.5 | 0.64 |
| Liver glycogen sample 1 (mmol/kg) | 278.0 | 48-620 | 430.0 | 188-722 | 0.01 |
| Liver TG sample 1 (mmol/kg) | 19.0 | 8.5-71.0 | 19.0 | 5.0-67.0 | 0.68 |
| Liver protein sample 1 (g/kg) | 109.0 | 62-158 | 94.0 | 42-152 | 0.13 |
| Liver glycogen sample 2 (mmol/kg) | 187.0 | 83-255 | 306.0 | 37-580 | 0.005 |
| Liver TG sample 2 (mmol/kg) | 26.0 | 9-70 | 18.0 | 5-182 | 0.43 |
| Liver protein sample 2 (g/kg) | 128.0 | 60-180 | 82.0 | 43-178 | 0.01 |

TG: triglycerides

TABLE 20

Hormonal Characteristics

| | Characteristics | Control group | Study group | P-value |
| --- | --- | --- | --- | --- |
| Induction | Insulin | 43.0 (20-52) | 83.0 (28-1611) | 0.35 |
| | Glucagon | 59.0 (39.0-92.0) | 43.0 (25.5-105.5) | 0.08 |
| | Free Fatty Acids | 0.9 (0.3-1.2) | 0.4 (0.2-2.2) | 0.79 |
| | Adiponectin | 124.0 (88.7-156.0) | 179.5 (114.0-271.5) | 0.02 |
| | Adipsin | 0.9 (0.6-1.5) | 1.3 (0.3-1.8) | 0.5 |
| 2-h into surgery | Insulin | 28.5 (45.0-85.5) | 902.5 (318.0-1715.0) | <0.001 |
| | Glucagon | 43.0 (22-81) | 37.0 (20-62) | 0.76 |
| | Free Fatty Acids | 0.80 (0.10-1.50) | 0.20 (0.06-9.40) | 0.57 |
| End of surgery | Insulin | 84.0 (28.0-295.0) | 458.5 (83.0-983.0) | 0.006 |
| | Glucagon | 46.0 (21-124) | 38.0 (18-68) | 0.17 |
| | Free Fatty Acids | 0.60 (0.06-1.50) | 0.10 (0.05-0.70) | 0.006 |
| 24-h after surgery | Insulin | 65.5 (45.5-262.5) | 258.5 (35.5-630.0) | 0.24 |
| | Glucagon | 93.0 (60-182) | 68.0 (26-366) | 0.91 |
| | Free Fatty Acids | 0.60 (0.06-0.90) | 0.20 (0.06-1.40) | 0.29 |

TABLE 20-continued

| Hormonal Characteristics | | | |
|---|---|---|---|
| Characteristics | Control group | Study group | P-value |
| Adiponectin | 77.7 (65.5-135.0) | 144.0 (68.7-230.0) | 0.03 |
| Adipsin | 1.2 (0.8-1.8) | 0.9 (0.3-1.4) | 0.06 |

Data are expressed as median (with range).
Insulin mU/L,
Glucagon pg/mL,
Free fatty Acids µmol/L,
Adiponectin ng/mL and
Adipsin mg/mL.

TABLE 21

| Inflammatory Characteristics | | | |
|---|---|---|---|
| Characteristics | Control group | Study group | P-value |
| Baseline C-RP (mg/L) | 7.0 (0.5-14.5) | 4.4 (1.0-88.0) | 0.57 |
| Intraoperative hours C-RP | 20.0 (3.0-72.0) | 19.0 (9.0-80.0) | 0.73 |
| 48-hours C-RP | 99.0 (59.0-201.0) | 106.0 (21.0-267.0) | 0.79 |
| 7-days C-RP | 153.5 (35.0-190.0) | 69.0 (47.5-170.0) | 0.35 |
| 30-days C-RP | 13.0 (0.8-132.0) | 3.1 (1.1-20.0) | 0.34 |
| Baseline IL-1B (pg/mL) | 0.0 (0.0-48.0) | 0.0 (0.0-75.5) | 0.94 |
| 2-hours into surgery | 0.0 (0.0-16.5) | 0.0 (0.0-67.0) | 0.75 |
| End of surgery | 0.0 (0.0-15) | 0.0 (0.0-24) | 0.59 |
| 24-hours after surgery | 0.0 (0.0-23) | 0.0 (0.0-26) | 0.97 |
| Baseline IL-6 (pg/mL) | 1.5 (0.0-26.0) | 1.5 (0.0-4.0) | 0.03 |
| 2-hours into surgery | 7.8 (3.0-56.0) | 19.0 (2.0-74.0) | 0.32 |
| End of surgery | 167.0 (52.0-489.0) | 86.0 (13.0-350.0) | 0.07 |
| 24-hours after surgery | 180.0 (51.0-360.0) | 126.0 (48.0-198.0) | 0.09 |
| Baseline IL-8 (pg/mL) | 12.0 (2.0-31.0) | 18.0 (3.0-66.0) | 0.07 |
| 2-hours into surgery | 14.0 (5.0-27.0) | 22.0 (5.0-344.0) | 0.10 |
| End of surgery | 48.0 (11.0-82.0) | 53.0 (10.0-489.0) | 0.14 |
| 24-hours after surgery | 36.8 (15.5-51.0) | 55.0 (23.5-152.0) | 0.04 |

Data are expressed as median (with range)

Example 8

GIN Therapy on Patients Undergoing a Major Liver Resection Results in Altered Inflammation, Reduced Apoptosis and Increased Cell Proliferation The sixty patients of Example 7 above, undergoing liver surgery are randomized to receive nutritional therapy coupled with tight glucose control (study) or standard insulin therapy (control). Study patients are given a 24-hour preoperative carbohydrate load at 35 kcal/kg/day followed by dextrose infusion at 2 mg/kg/h for a total of 8 hours. Insulin therapy is then initiated in these patients with the hyperinsulinemic normoglycaemic clamp and involved administering 1.2 U/kg/h intraoperatively and 0.06 U/kg/h postoperatively for a total of 24 hours. Controls fasted preoperatively for 8 hours then received standard sliding scale insulin therapy. Ten patients are randomly selected from each group for inflammatory mediator, and genetic expression testing.

Assessments and Tests

Blood samples are taken from study patients during the morning of the operation just prior to starting the insulin clamp. A second sample is taken 2 hours into the operation and a third one at the end of surgery. The last sample is withdraw 24 hours from the time of first withdrawal. Blood samples are immediately divided into 1 mL sub samples and stored at $-80°$ C. Complement factors C3 and C5a, Adiponectin, Adipsin, growth hormone and TGF-$\alpha$ are measured with commercial ELISA kits (BD OptEIA human C5a ELISA kit, BD Biosciences, C3 Complement Assay, Kamiya Biomedicals, Custom Human Quantibody Array, Raybiotech) and ASP (C3adesARG) is quantified with sandwich ELISA.

Cytokine Analysis

Human IL-6, IL-8, IL-10, MCP-1 and TNF-$\alpha$ are measured by suspension bead array immunoassay with a Luminex 200 X-map instrument (Luminex Corp, Austin, Tex., USA). Analysis of the cytokines is carried out using a Milliplex human cytokine kit following manufacturer's specifications (MPXHCYTO-60k, Millipore Corp, Bilerica, Mass., USA). All samples are analyzed in duplicate and the kit has a sensitivity of 0.4 pg/mL. Concentrations are calculated from the standard curve generated by the MasterPlex QT 4.0 analysis software (MiraiBio Inc, Alameda, Calif., USA).

Tissue Biopsies

Two tissue samples are removed from the liver FLR; one at the time of incision and one at the end of surgery. Samples are snap-frozen and stored at $-80°$ C. mRNA is extracted and purified from the frozen tissues using RNeasy mini kits (Qiagen, Gaithersburg, Md., USA) then reverse transcribed into DNA with a RT2 First Strand kit (SA Biosciences, Frederick, Md., USA). Both steps follow the manufacturer's instructions. 84 genes are quantified from each sample using Human Insulin Pathway PCR array cycle time (Ct) measurements (SA Biosciences, Frederick, Md., USA). Genes for C5L2, C3aR, C5aR, Caspases 8 and 9, BAX and BCL2 are measured individually with QuantiTect primers (Qiagen, Gaithersburg, Md., USA). Relative gene expression is calculated and corrected from measurement of 5 housekeeping genes included in the PCR array. All procedures follow MIQE guidelines.

Statistics

The data are expressed as means±SD or medians and interquartile range if not normally distributed. Demographic, operative and postoperative variables are compared using the unpaired t-test or Mann-Whitney U test for continuous data. Proportions are compared by the Chi-square or Fisher Exact tests. A principle component analysis is applied (PCA; Statistica version 9 statistical package) to reduce the large number of study variables (136) to a smaller set of uncorrelated variables containing most of the information in the original data. Missing values are replaced with the mean. The PCs are rotated using an orthogonal rotation-varimax normalized and only those components with eigenvalues ≥5 are retained. Sample factor scores (values) for each component are saved and used in a subsequent logistic regression analysis. A P-value≤0.1 is considered as significant.

Baseline Data

Study and control patients have comparable demographics with a few exceptions, and both groups exhibited similar baseline liver function and perioperative characteristics (Tables 22 to 24). A greater incidence of hypertension and a borderline higher serum creatinine (renal dysfunction) was found at baseline in our study cohort. Study patients were older and there were non-significantly more males in this group (Table 1). Since older age is a well-known risk factor for liver dysfunction this difference may have created some biases in the study data. In addition, the smaller sample size used in the trial segment described here may explain why the demographics of the original randomized groups were significantly more alike (46).

TABLE 22

Demography of patients

| Variable | Study (n = 10) | Control (n = 10) | P value |
|---|---|---|---|
| Age | 71 (67-82) | 53 (45-59) | 0.006 |
| DM | 1.0 (10%) | None | 0.38 |
| HTN | 4.0 (40%) | None | 0.04 |
| IHD | 2.0 (20%) | None | 0.2 |
| High Cholesterol | 2.0 (20%) | None | 0.2 |
| Sex male % | 5.0 (50%) | 2.0 (20%) | 0.3 |
| BMI | 26.7 (25.5-30) | 25.4 (21.0-25) | 0.34 |

Data are reported as median and (interquartile range) or number and (percentage).

TABLE 23

Laboratory tests at baseline: hepatic and renal function

| Variable | Study | Control | P value |
|---|---|---|---|
| FLR (mL) | 764 (523-1014) | 578 (521-639) | 0.3 |
| TLV (mL) | 1765 (1573-1792) | 1440 (1232-1678) | 0.1 |
| FLR/TLV ratio | 40 (29-75) | 41 (33.6-48.7) | 0.9 |
| Base deficit | 1.8 (0.1-4.0) | 0.7 (−0.7-1.4) | 0.2 |
| Lactic acid mg/dL [mmol/L] | 9.0 (5.9-10.8) [1.0 (0.65-1.2)] | 7.2 (6.3-8.1) [0.8 (0.7-0.9)] | 0.2 |
| Total Bilirubin mg/dL μmol/L | 0.8 (0.7-4.4) [13 (12-76)] | 1.2 (1.0-1.9) [21 (17-32)] | 0.3 |
| INR | 1.0 (1-1) | 1.0 (1-1) | 0.5 |
| Creatinine mg/dL μmol/L | 1.1 (1.1-1.4) [84 (81-104)] | 0.9 (0.8-1.0) [69 (58-75)] | 0.05 |

Data are reported as median and (interquartile range).

TABLE 24

Intraoperative characteristics

| Variable | Study | Control | P value |
|---|---|---|---|
| Trisegmentectomy | 3.0 (30%) | 2.0 (20%) | 0.9 |
| # of segments removed | 4.0 (3.0-4.5) | 4.0 (3.5-5.0) | 0.7 |
| Duration of OR | 3.0 (2.6-3.4) | 3.0 (2.7-3.8) | 0.7 |
| Blood loss | 1100 (500-1800) | 1300 (750-2500) | 0.4 |
| Blood Transfusion | None | 2.0 (20%) | 0.1 |
| Units of RBC given | 0.0 (0-0) | 0.0 (0-2) | 0.1 |
| Crystalloid (L) | 3.0 (1.5-4.0) | 3.8 (2.5-4.0) | 0.4 |
| Colloid (mL) | 500 (400-1000) | 500 (500-1000) | 0.7 |
| Pringles (min) | 0.0 (0-10) | 0.0 (0-7) | 0.8 |
| Fibrosis (0-4) | 0.0 (0-0) | 0.0 (0-2) | 0.3 |
| Steatohepatitis (0-3) | 1.0 (1-1) | 0.0 (0-2) | 0.4 |

Data are reported as median and (interquartile range) or number and (percentage).

Clinical Outcomes

Better clinical outcome are noted on markers in the study patients. These data are reported previously in Example 7 above and will only be summarized here. Study patients have better liver function scores as per Schindl, 2 (range 0-4) compared to 3 (range 2-8) for the controls, (P=0.03) and demonstrate a 26% reduction in overall complications compared to only 17% for the controls. Infections of Clavien grade 2 or higher occurred in 11% of patients in the control group and none in the study group. PCA establishes significant associations between liver repair activity and intervention, and between postoperative liver dysfunction and infections.

Primary Outcomes

Complement System is not Affected

Studies reporting association between blood glucose levels and complement activation are conflicting. In some studies increased complement function associated with higher circulating glucose levels while other studies have shown an opposite trend. Regardless, alteration in complement function consistently resulted from either hyper- or hypoglycaemia. No major intergroup differences in levels of circulating or genetic parameters related to the complement system (C3, ASP, C5a, C5aR, C3aR, C5L2) indicates that neither group experienced blood glucose fluctuations sufficiently out of normal range or often enough to influence complement function. Absence of complement function alterations in adult coronary artery bypass grafting (CABG) patients receiving strict glucose control is also observed by Hoedemakers, in agreement with our findings (Example 6). The absence of modulation in complement activation in addition to lack of a relationship between complement factors and clinical outcomes suggests that the beneficial effects of our protocol are not related to the complement system.

A recent study that looked at changes in complement function occurring after LR reported increases in C3a, and C5b9 by 34% and 112%, respectively, while C4a and C5a levels decreased by 25% and 30%, respectively. The authors did not mention whether or not patients received glucose control therapy. In this study, changes in complement factors after surgery were also found: while C3 levels decreases significantly by −43%, (P<0.0001), C5a levels were mildly but not significantly reduced (−27%, P=0.39) in study and control patients alike.

Inflammatory Mediators and Glucose Balance

Figure 8:
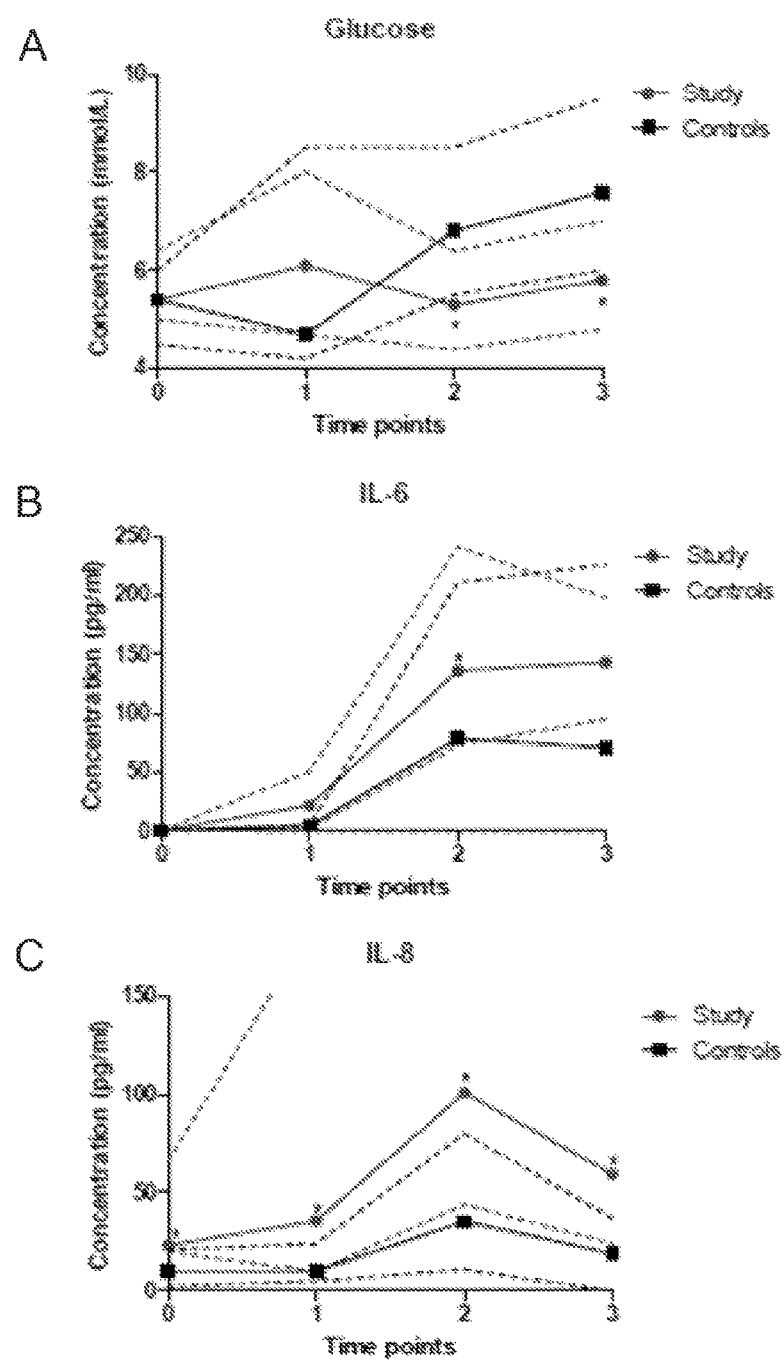
FIG. 8 illustrates the perioperative concentration of glucose (A) and cytokines IL-6 (B), IL-8 (C), TNG-a (D), MCP1 (E), and IL-10 (F); T0=baseline, T1=2 h into surg., T2=end of surg., T4=24 h after surg. Values are shown as mean±range.
Figure 8:
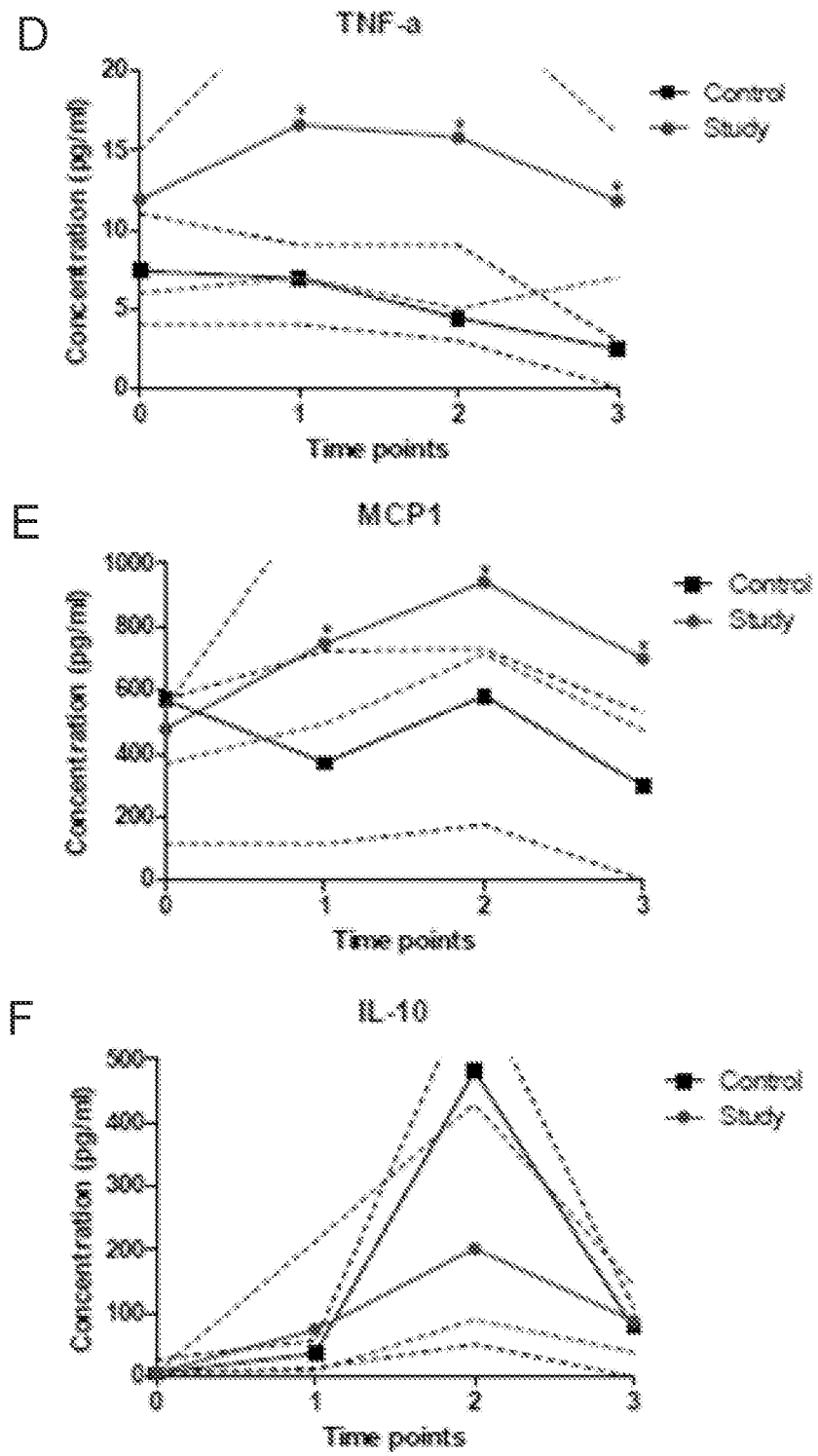

Proinflammatory mediators such as IL-6, IL-8, TNF-α and MCP-1 increase acutely for both the study and control groups during the resection while IL-1β is undetectable, as would be expected for patients undergoing major surgery. However, the study group exhibits significantly higher levels of proinflammatory cytokines at most data collection time points after initiation of surgery, as seen in FIG. 8. There was observed an opposite trend in circulating levels of glucose and the anti-inflammatory factor IL-10. While initial glucose levels are comparable in study and control patients, a rise in serum glucose concentration is detected throughout the surgery for the controls only (Table 25).

TABLE 25

Glucose levels at different time intervals in mg/dL [mmol/L]

| Variable | | Study | Control | P value |
|---|---|---|---|---|
| Prior to surgery | Baseline | 97 (93-108) [5.4 (5.2-6.0)] | 97 (83-108) [5.4 (4.6-6.0)] | 0.8 |
| | Preinduction | 110 (85-117) [6.1 (4.7-6.5)] | 85 (79-135) [4.7 (4.4-7.5)] | 0.6 |

TABLE 25-continued

Glucose levels at different time intervals in mg/dL [mmol/L]

| Variable | | Study | Control | P value |
|---|---|---|---|---|
| During the surgery | 1 hour | 95 (94-108) [5.3 (5.2-6.0)] | 123 (110-144) [6.8 (6.1-8.0)] | 0.02 |
| | 3 hours | 105 (94-117) [5.8 (5.2-6.2)] | 137 (114-162) [7.6 (6.3-9.0)] | 0.04 |

Data are reported as median and (interquartile range).

Interestingly, PCA analysis associates these two findings: a component (PC7), representing activation of glucose/insulin-sensitive genes prior to surgery and perioperative release of circulating proinflammatory molecules, negatively associated with the control group. This suggests that a more pronounced stimulation of glucose metabolism by insulin leads to stable blood glucose throughout the surgery and permits a stronger acute rise in proinflammatory factors known to initiate liver regeneration.

Preoperative Status Influences the Clinical Outcomes

Published results consistently show a strong association between preoperative state of the patient and major clinical outcome parameters. Hepatic glycogen levels in study patients are elevated compared to control subjects prior (+64%, P=0.006) and after (+36%, P=0.04) the surgery (Example 7 above). In the present investigation PCA analysis reveals that other preoperative parameters are associated with clinical benefits. A component (PC4) representing activation of insulin-responsive genes related to PI3K and MAPK pathways prior to surgery, negatively associates with the presence of infectious complications. Additionally, a group of variables (PC8) describing preoperative circulating levels of inflammatory related molecules such as IL-6, TNF-α and IL-10 correlates with postoperative liver dysfunction (r=0.526, P<0.01). These observations suggest that the preoperative state of the patient independently associates with clinical outcomes and strongly advocates further studies for investigating a potential causal relationship.

Postoperative Status Influences the Clinical Outcomes

Figure 9:
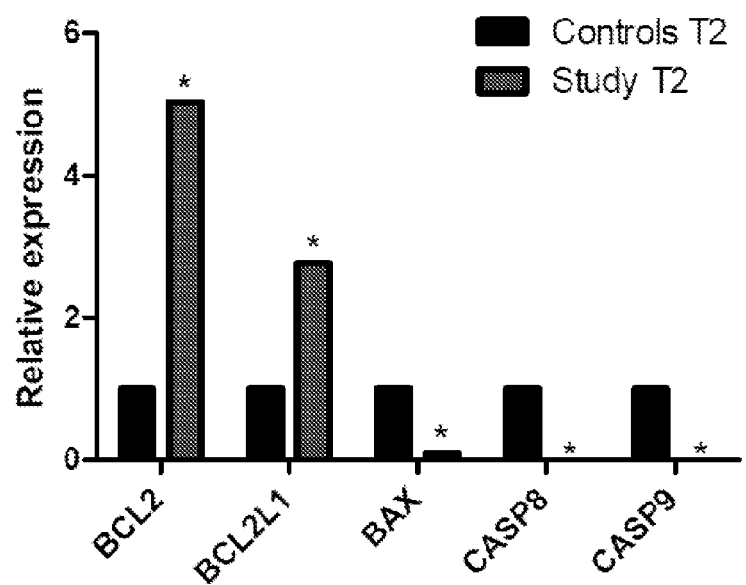
FIG. 9 illustrates the relative apoptotic gene expression levels after liver resection for study (open bars) and control (opaque bars) patients.

Cell death that occurs through apoptosis represents a major complication from LR. Results for the study patients clearly show that the insulin therapy protocol provides an anti-apoptotic protective effect on the hepatocytes. Genes protecting against programmed cell death such as BCL2 (P=0.01), BCL2L1 (P=0.02) are increased in study patient liver biopsies. By contrast, proapoptotic genes such as BAX (P=0.04), Caspase 8 (P=0.004) and Caspase 9 (P=0.01) are higher in control patients (FIG. 9). These findings suggest that the intervention protocol achieves its clinical benefits partly through a reduction in hepatocytes apoptosis.

PCA analysis classifies into one independent component (PC1) a vast set of factors describing proliferation and survival at the end of surgery that mainly occurs through PI3K and MAPK pathways. This component negatively associates with the presence of complications therefore emphasizing the importance of MAPK and PI3K pathway mediated cell proliferation for reducing postoperative complications.

Figure 10:
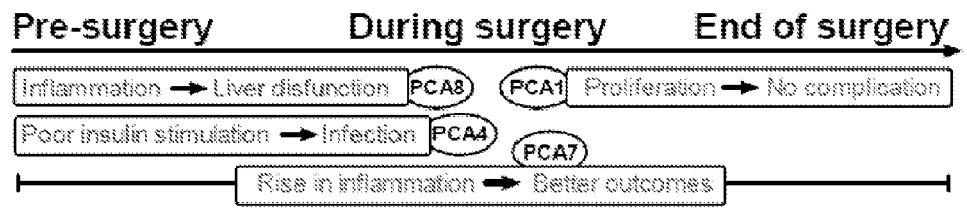
FIG. 10 illustrates the associations between clinical outcomes and biological markers in LR patients at all stages of surgery.

A summary of associations observed between clinical outcomes and biological markers throughout the surgery is summarized in FIG. 10. Many of the published risk factors for POLD and complications are unchangeable, like age or male gender, or unavoidable such as major resection or blood transfusion. This study explores a potential method that can alter and modify LR response and promote improvements in surgical outcome.

Conclusions

The results presented in this example link several clinical outcomes with biological parameters in patients undergoing major liver resection. In particular, insulin therapy reduced postoperative liver dysfunction by suppressing inflammation and associated apoptosis. These results are genuine since the study design does not allow pre-emptive assumptions regarding the effect of intervention on any specific parameter towards altering its clinical outcome.

Example 9

High-Dose Insulin Therapy Reduces Postoperative Liver Dysfunction and Complications in Liver Resection Patients Through Reduced Apoptosis and Altered Inflammation Context:

An exaggerated inflammatory response in patients undergoing major liver resection coupled with poor nutrition diminishes liver regenerative capacity and increases the risk of postoperative complications.

Objectives:

To evaluate the biological context leading to better clinical outcomes in patients undergoing liver resection coupled with hyperinsulinemic-normoglycemic clamp VS standard care (insulin sliding care).

Design and Setting:

Fundamental research analysis of a patient subset from a randomized-controlled study at the McGill University Health Center.

Intervention:

Thirty consenting patients participating in a randomized clinical trial for liver resection received either hyperinsulinemic-normoglycemic clamp technique with 24-hour preoperative carbohydrate load (intervention) or standard glucose control through insulin sliding scale treatment (control).

Main Outcome Measures:

Liver biopsies and plasma samples were taken at various time points pre- and post-surgery. Primary measures included mRNA quantitation for genes related to insulin signalling, inflammation and proliferation, proinflammatory cytokines at various time points and liver function markers. These measurements were associated with clinical outcomes.

Results:

The hyperinsulinemic-normoglycemic clamp technique reduced postoperative liver dysfunction, infections and complications. Markers of energy stores indicated higher substrate availability. Cytokine expression pattern was altered (TNF-α, IL-8, MCP-1, IL-6, IL-10, CRP). Apoptosis was markedly reduced while the complement system was unaltered.

Conclusion:

The hyperinsulinemic-normoglycemic clamp technique reduced postoperative negative outcomes by suppressing apoptosis. This phenomenon appears to be linked with higher substrate availability and altered cytokine secretion profile and may provide a long-term benefit of this therapy on liver resection patients.

Material and Methods

Patients

This study analyses a subset of 30 patients that participated in a liver resection clinical trial (Clinicaltrial.gov Identifier: NCT00774098). The consenting patients undergoing liver surgery were randomized to receive nutritional therapy coupled with tight glucose control (intervention) or standard glucose control (control). Intervention patients were given a 24-hour preoperative carbohydrate load at 35 kcal/kg/day followed by dextrose infusion at 2 mg/kg/h for a total of 8 hours. Insulin therapy was then initiated in these patients with the hyperinsulinemic-normoglycaemic clamp with administration of 1.2 U/kg/h intraoperatively and 0.06 U/kg/h postoperatively for a total of 24 hours. For the control group, patients fasted preoperatively for 8 hours then received standard sliding scale insulin treatment.

Clinical Outcomes

Postoperative liver function was scored using the system developed by Schindl et al (Schindl M et al. 2005, Archives of Surgery 140(2):183-189). This system grades liver dysfunction according to the levels of lactic acid, total bilirubin, INR and encephalopathy postoperatively. Total scores of 0, 1-2, 3-4, or >4 are used to classify liver dysfunction as absent, mild, moderate or severe, respectively. Surgical morbidity in the 30 days following the operation was ranked as per Clavien et al. (Dindo et al. 2004, Annals of Surgery 240(2):205-213). Morbidities were classified as either infectious or non-infectious.

Assessments and Tests

A first blood sample was taken from patients during the morning of the operation just prior to starting the insulin clamp (Surgery sample 1: S1). A second sample was taken 2 hours into the operation (Surgery sample 2: S2) and a third one at the end of surgery (Surgery sample 3: S3). A last blood sample was obtained 24 hours from the time of the first blood sampling (24 h). Additional blood samples were drawn at 12 h, 48 h, 7 days and 30 days from the time of the first blood sampling for select measurement of parameters requiring long-term monitoring (glucose, CRP, ALT/AST). Blood samples were centrifuged and the supernatant immediately divided into 1 mL aliquots and stored at −80° C.

Complement factors C3 and C5adesArg were measured with commercial ELISA kits (BD OptElA for human C5a ELISA kit, C3 Complement Assay from Kamiya Biomedicals). Adiponectin, adipsin, EGF, HGF, IGF-I, GH and TGF-α, TGF-β were measured using a commercial antibody array (Custom Human Quantibody Array, Raybiotech). ASP (C3adesARG) was quantified with a sandwich ELISA assay. These measurements were carried out on blood samples pre- and 24 h post-surgery (S1 & 24 h samples).

Cytokine Analysis

Human IL-1β, IL-6, IL-8, IL-10, MCP-1 and TNF-α were measured using a suspension bead array immunoassay kit following manufacturer's specifications (Milliplex human cytokine MPXHCYTO-60k, Millipore Corp, Bilerica, Mass., USA) on a Luminex 200 X-map instrument (Luminex Corp, Austin, Tex., USA). All samples were analyzed in duplicate and the kit had a sensitivity of 0.4 pg/mL. Concentrations were calculated from the standard curve generated by the MasterPlex QT 4.0 analysis software (MiraiBio Inc, Alameda, Calif., USA).

Tissue Biopsies

Two tissue samples were removed from the future liver remnant; one at the time of incision (Pre) and one at the end of surgery (Post). Samples were snap-frozen and stored at −80° C. mRNA was extracted and purified from the frozen tissues using RNeasy mini kits (Qiagen, Gaithersburg, Md., USA), reverse transcribed into cDNA with a $RT^2$ First Strand kit (SA Biosciences, Frederick, Md., USA). Both steps followed manufacturer's instructions. 84 genes were quantified from each sample using Human Insulin Pathway PCR array cycle time (Ct) measurements (SA Biosciences, Frederick, Md., USA). mRNA for C5L2, C3aR, C5aR, Caspases 8 and 9, BAX and BCL2 genes were measured individually using QuantiTect Primer Assays (Qiagen, Gaithersburg, Md., USA). Relative gene expression was calculated and corrected with a combination of five housekeeping genes included in the PCR array. All procedures followed MIQE guidelines.

Statistics

Data is expressed as mean±SEM. Demographic, operative and postoperative variables were compared using the unpaired t-test or Mann-Whitney U test for continuous data while proportions were compared using Fisher exact test. For each measurement the change from baseline was analyzed using two-factor repeated measures ANOVA to test for differences between intervention groups and over time. Distribution was not normal for all variables except glucose and the distribution of these latter measures was normalized using a logarithmic transformation. Relations between variables were evaluated using Spearman rank's correlation coefficient with further significance determination. A P-value≤0.1 was considered as significant (*=p<0.1, p<0.05, *p<0.01).

Results

Baseline Data

Intervention and control patients had comparable baseline characteristics with the exception of age, as intervention patients were older (Table 26). Both groups exhibited similar baseline liver function and perioperative characteristics.

TABLE 26

Baseline and clinical outcomes

| | Intervention (n = 19) | Controls (n = 11) | p-value |
|---|---|---|---|
| Age (years) | 63.0 ± 10.0 | 53.9 ± 8.5 | 0.02** |
| Sex (female/male) | 11/8 | 5/6 | 0.41 |
| BMI (kg/m$^2$) | 25.7 ± 3.1 | 26.8 ± 3.5 | 0.35 |
| HT (cases) | 5.0 (26%) | 2.0 (18%) | 0.84 |
| HD (cases) | 3.0 (16%) | None | 0.89 |
| High Cholesterol (cases) | 1.0 (5%) | None | 0.73 |
| DM (cases) | 1.0 (5%) | 1.0 (9%) | 0.62 |
| Liver dysfunction (Schindl score) | 2.3 ± 1.1 | 3.5 ± 1.9 | 0.03** |
| Infections (Clavien score) | 0.16 ± 0.40 | 0.55 ± 0.82 | 0.08* |
| Complications (Clavien score) | 0.58 ± 0.69 | 1.36 ± 1.80 | 0.09* |
| Length of stay (days) | 10.9 ± 5.5 | 11.1 ± 8.0 | 0.94 |

Data are presented as mean ± SEM, number of events (% of occurrence in the group).
BMI, body-mass index;
HT, hypertension;
HD, heart disease;
DM, diabetes mellitus.
*P < 0.1;
**P < 0.05;
***P < 0.01.
For controls, n = 11, for intervention, n = 19.

Insulin Therapy Improves Clinical Outcomes

In this study, complications (p=0.09), infectious complications (p=0.08) and liver dysfunction (p=0.03) were all shown as significantly improved in the intervention group (Table 26). The insulin treatment reduced by 27% the cases of complications. Infections of Clavien grade 2 or higher occurred in 18% of the control group and no event was recorded in the intervention group. Similar results were reported in Example 8.

Complement System is Mildly Affected by the Intervention

In order to evaluate the mechanisms through which insulin therapy improved clinical outcomes, changes in several pathways and systems associated with liver regeneration were assessed. A significant reduction in pre-surgery (S1) circulating C3 (−14%, p=0.08) was seen in the intervention subjects. C3 levels were substantially reduced after surgery (24 h) in both groups alike (−48%, p=0.002 controls, −35% intervention, p=0.0001) compared to preoperative levels. However, the cleavage products of complement activation, C5adesArg and ASP (C3adesArg) were not different either pre- vs post-surgery or altered by the intervention.

C3a receptor mRNA tended to be decreased in intervention subjects both prior to and at the end of the surgery (−57%, p=NS). C5a receptor (C5aR) mRNA was decreased in the intervention group preoperatively (−69%, p=0.02). Both intervention and surgery tended to increase expression of C5L2, the receptor for ASP (C3adesArg) and C5a, although non-significantly.

Insulin Therapy Alters the Energetic Status Throughout the Surgery

Figure 11:
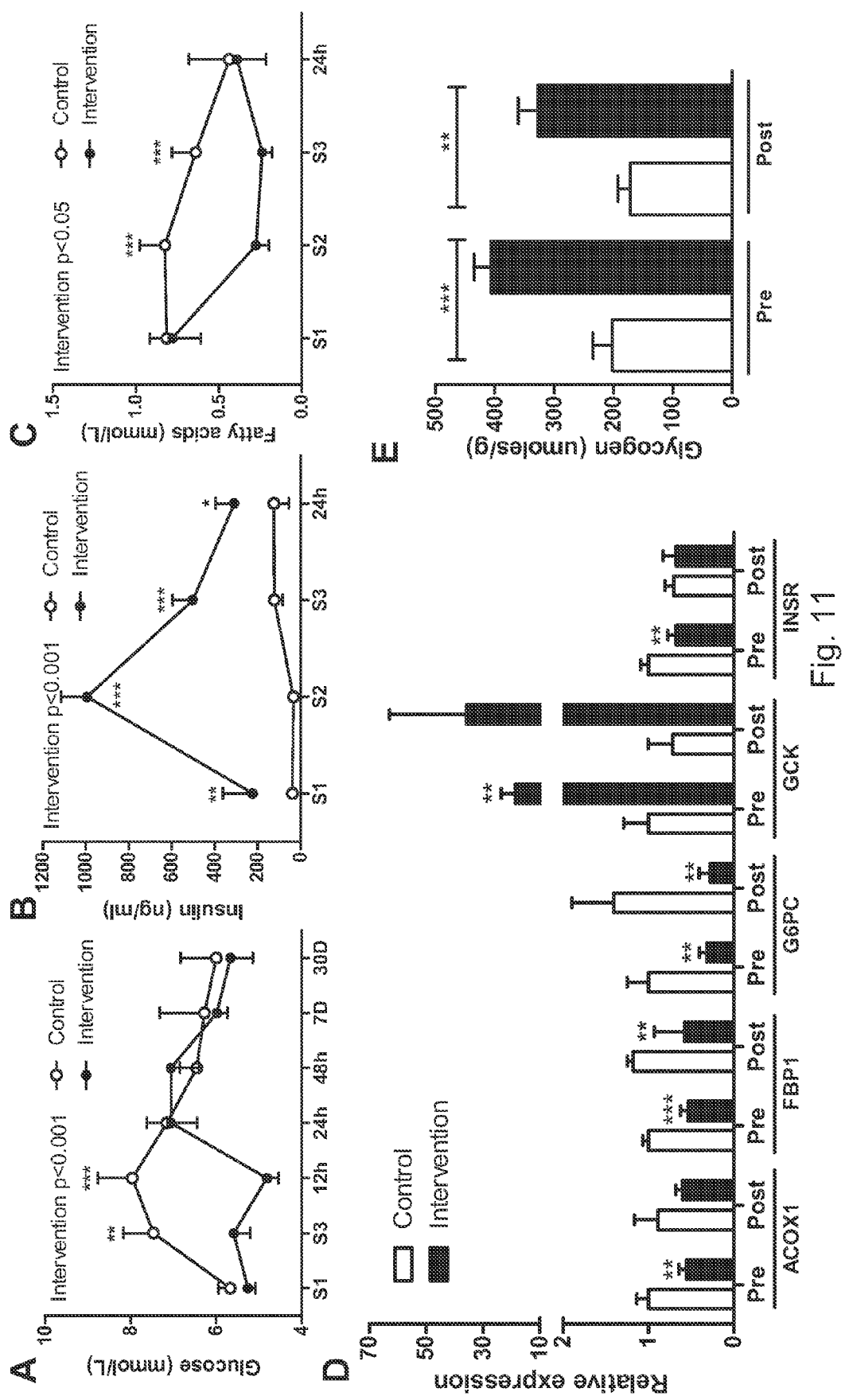
FIG. 11 illustrates energetic status throughout the surgery; A) Plasma glucose during and up to 30 days post-surgery. B) Circulating insulin during and 24 h post-surgery. C) Plasma fatty acid during and 24 h post-surgery. D) Relative expression of genes related to energy metabolism. Values for each gene are relative to pre-surgery control group values. E) Hepatic glycogen pre- and post-surgery. Data are presented as mean±SEM. ACOX, acetyl-CoA carboxylase; FBP1, fructose 1-6-biphosphatase; G6PC, glucose 6-phosphatase; GCK, glucokinase; INSR, insulin receptor. *P<0.1; P<0.05; *P<0.01. For controls, n=9-11, for intervention, n=17-19 (A-C, E). For controls, n=7-8, for intervention, n=7-8 (D).

Blood glucose, fatty acids, insulin and glucagon as well as mRNA content of hepatic enzymes were assessed to quantify metabolic changes due to the treatment. Patients undergoing insulin therapy prior and during the surgery were able to maintain a tighter glucose control throughout the operation and in the hours following (S3, p=0.05, 12 h, p=0.001) when compared to control patients (FIG. 11A) although pre- and post-insulin therapy glucose levels (S1, 24 h, respectively) were comparable. Associated perioperative insulin levels (S2, S3), provided through clamp administration, were also substantially increased in intervention patients (p<0.001) (FIG. 11B) while preoperative (S1) glucagon levels were mildly decreased (p<0.05). Circulating fatty acids were significantly higher in control patients during the surgery (S2, p=0.002, S3, p=0.009), potentially reflecting the lack of sufficient glucose availability (FIG. 11C).

Elevated insulin levels and high glucose availability in subjects receiving insulin treatment altered hepatic energetic metabolism prior to surgery. Liver mRNA content of several key enzymes was changed preoperatively: acetyl-CoA carboxylase (ACOX1) was significantly lowered in treated patients, which suggests lower fatty acid oxidation (p<0.05) (FIG. 11D). Conversely, mRNA content of genes indicative of a positive cellular balance of glucose were altered: glucokinase (GCK, p<0.05) mRNA was strongly increased while fructose-1,6-biphosphatase (FBP1, p<0.01) and glucose 6-phosphatase (G6PC, p<0.05) mRNA were decreased. FBP1 and G6PC mRNA content were also significantly reduced post-surgery (p<0.05 for both), suggesting lasting and profound effects of the insulin therapy on substrate availability (FIG. 11D). Statistical correlation between insulin or hepatic glycogen levels at the end of the surgery with clinical outcomes were however not significant (Table 27).

Consistent with increased expression of genes associated with high substrate availability in intervention patients, hepatic glycogen levels were also significantly elevated prior (p=0.0002) and post-surgery (p=0.003) (FIG. 11E), as previously demonstrated in Example 8.

TABLE 27

Correlations between clinical outcomes, plasma cytokines and energy markers

| | Liver dysfunction | | Infectious complications | | All complications | | Lenght of stay | |
|---|---|---|---|---|---|---|---|---|
| | p value | r | p value | r | p value | r | p value | r |
| TNF-α | 0.091* | −0.42 | 0.472 | 0.143 | 0.272 | 0.218 | 0.153 | 0.282 |
| IL-8 | 0.52 | 0.129 | 0.569 | 0.113 | 0.264 | 0.222 | 0.004*** | 0.536 |
| MCP-1 | 0.11 | 0.312 | 0.059* | 0.367 | 0.025** | 0.429 | 0.056* | 0.371 |
| IL-6 | 0.011** | 0.492 | 0.056* | 0.379 | 0.056* | 0.379 | 0.013** | 0.48 |
| IL-10 | 0.141 | 0.289 | 0.258 | 0.224 | 0.349 | 0.186 | 0.033** | 0.411 |
| CRP | 0.389 | 0.263 | 0.045** | 0.583 | 0.263 | 0.341 | 0.635 | 0.148 |
| Adiponectin | 0.374 | −0.243 | 0.209 | −0.338 | 0.602 | −0.143 | 0.281 | −0.293 |
| TGF-α | 0.211 | 0.328 | 0.014** | 0.597 | 0.064* | 0.47 | 0.738 | 0.089 |
| Insulin | 0.586 | −0.153 | 0.255 | −0.313 | 0.329 | −0.271 | 0.700 | 0.109 |
| Liver glycogen | 0.133 | −0.309 | 0.565 | −0.121 | 0.321 | −0.207 | 0.389 | −0.180 |

Correlations are presented as p value and Spearman correlation coefficient (R).
CRP, C-reactive protein;
MCP-1, monocyte chemoattractant protein 1.
*P < 0.1;
**P < 0.05;
***P < 0.01.
For all correlations, n = 27-30.

TABLE 28

Correlations between apoptosis-related genes, plasma cytokines and energy markers

| | BCL2 | | CASP8 | | CASP9 | | BCL2L1 | | BAX | |
|---|---|---|---|---|---|---|---|---|---|---|
| | p value | r | p value | r | p value | r | p value | r | p value | r |
| TNF-a | 0.051* | 0.752 | 0.084* | −0.645 | 0.095* | −0.628 | 0.442 | 0.349 | 0.129 | −0.63 |
| IL-8 | 0.012** | 0.866 | 0.248 | −0.463 | 0.285 | −0.432 | 0.202 | 0.549 | 0.439 | −0.352 |
| MCP-1 | 0.057* | 0.74 | 0.304 | −0.417 | 0.363 | −0.373 | 0.807 | 0.115 | 0.442 | −0.349 |
| IL-6 | 0.709 | −0.197 | 0.158 | 0.595 | 0.165 | 0.588 | 0.379 | −0.396 | 0.912 | −0.058 |
| IL-10 | 0.254 | −0.5 | 0.296 | 0.424 | 0.109 | 0.609 | 0.196 | −0.555 | 0.027 | 0.812 |
| CRP | 0.206 | −0.68 | 0.005*** | 0.975 | 0.056* | 0.869 | 0.574 | −0.426 | 0.238 | 0.647 |
| Adiponectin | 0.959 | −0.033 | 0.885 | −0.077 | 0.588 | −0.282 | 0.576 | 0.34 | 0.444 | −0.453 |
| TGF-a | 0.191 | −0.56 | 0.125 | 0.635 | 0.286 | 0.471 | 0.075* | −0.767 | 0.347 | 0.47 |

TABLE 28-continued

Correlations between apoptosis-related genes, plasma cytokines and energy markers

| | BCL2 | | CASP8 | | CASP9 | | BCL2L1 | | BAX | |
|---|---|---|---|---|---|---|---|---|---|---|
| | p value | r | p value | r | p value | r | p value | r | p value | r |
| Insulin | 0.016** | 0.894 | 0.039** | −0.779 | 0.026** | −0.813 | 0.017** | 0.842 | 0.012** | −0.911 |
| Liver glycogen | 0.054* | 0.747 | 0.035** | −0.742 | 0.01** | −0.834 | 0.127 | 0.634 | 0.005*** | −0.904 |

Correlations are presented as p value and Spearman correlation coefficient (R).
CRP, C-reactive protein;
MCP-1, monocyte chemoattractant protein 1.
BCL2, B-cell lymphoma 2 protein;
BCL2L1, B-cell lymphoma 2-like protein;
CASP8, caspase 8; CASP9, caspase 9;
BAX, B-cell lymphoma 2-associated X protein.
*$P < 0.1$;
**$P < 0.05$;
***$P < 0.01$.
For all correlations, n = 12-16.

Inflammatory Response is Affected by the Intervention

Figure 12:
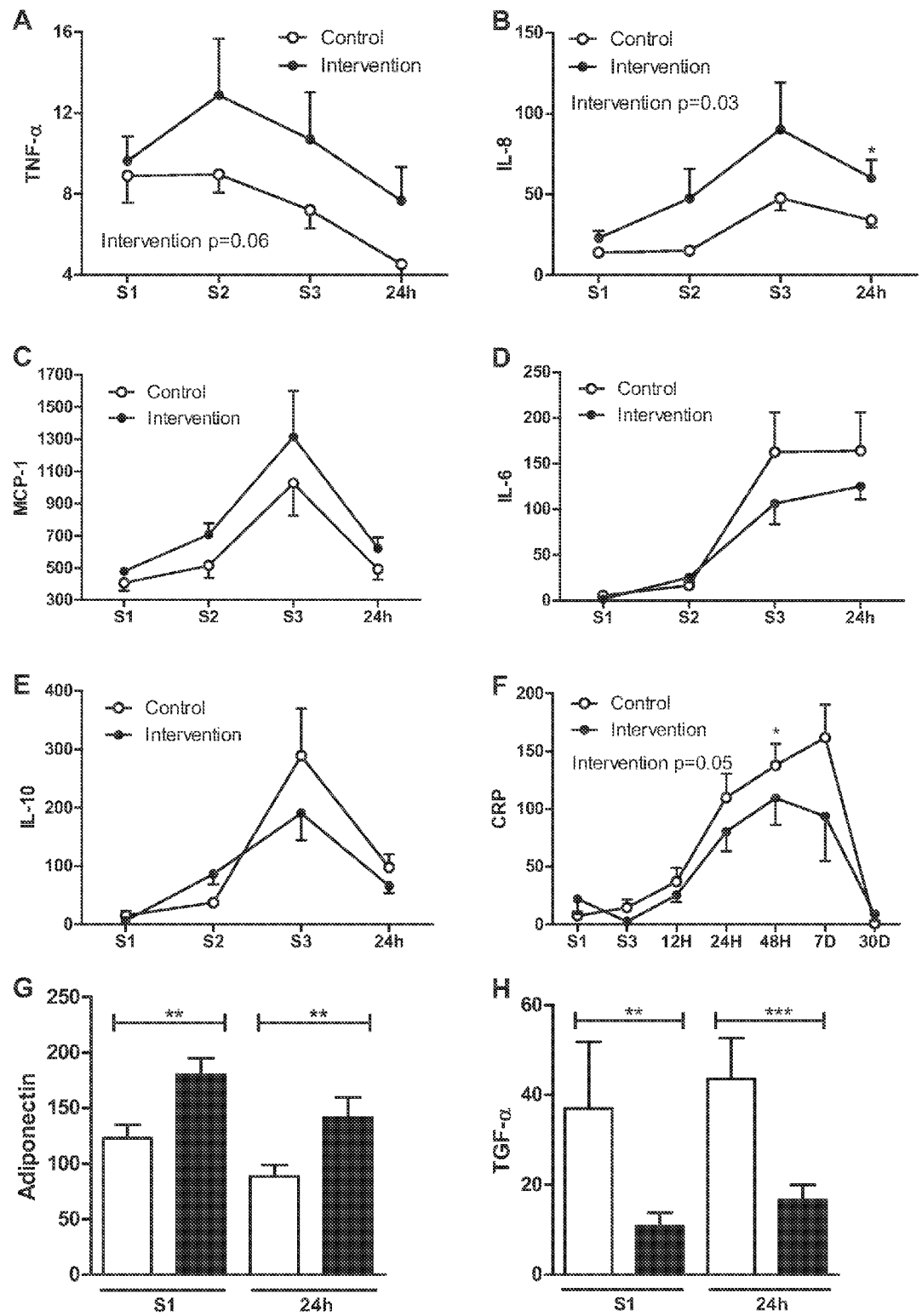
FIG. 12 illustrates cytokines secretion profile; A) Plasma TNF-α during and 24 h post-surgery. B) Plasma IL-8 during and 24 h post-surgery. C) Plasma MCP-1 during and 24 h post-surgery. D) Plasma IL-6 during and 24 h post-surgery. E) Plasma IL-10 during and 24 h post-surgery. F) Plasma CRP during and up to 30 days post-surgery. G) Plasma adiponectin pre- and 24 h post-surgery. H) Plasma TGE-α pre- and 24 h post-surgery. Data are presented as mean±SEM. CRP, C-reactive protein; MCP-1, monocyte chemoattractant protein 1. *P<0.1; P<0.05; *P<0.01. For controls, n=9-11, for intervention, n=17-19.

The concentration of several inflammatory mediators (IL-1β, IL-6, IL-8, IL-10, TNF-α, MCP-1, CRP) was followed throughout the surgery (FIG. 12A-F). IL-1β was undetectable. At the beginning of the surgery (S1), there was no significant difference in cytokine levels between control and intervention patients. However, during (S2 and S3) and after surgery (24 h), the intervention altered the profile in a cytokine-specific fashion. While TNF-α, IL-8 and MCP-1 peaks, which were primarily attained at S3, were higher in intervention subjects, IL-6 and IL-10 were higher in control subjects, as seen in FIG. 12A-E. After surgery (24 h), most cytokine levels were comparable to pre-surgery levels (S1) for both control and intervention groups, with the exception of IL-6, which remained elevated. C reactive protein (CRP) increased with surgery, remaining elevated up to 7 days after surgery, returning eventually to baseline after 30 days, with a consistent increase in the control group vs. the intervention group (FIG. 12F).

Adiponectin, adipsin, EGF, HGF, IGF-1, GH and TGF-α, TGF-β were also measured in plasma sample pre- and 24 h post-surgery (S1, 24 h, respectively). Most factors remained unaffected by the intervention (adipsin, EGF, HGF, GH) or were undetectable (IGF-1, TGF-β). However, adiponectin levels were significantly increased prior to and after surgery in the intervention group (S1, p=0.02, 24 h, p=0.03) while TGF-α levels were substantially reduced (S1, p=0.01, 24 h, p=0.007) (FIG. 2G-H).

Peak cytokine levels at the end of the surgery (S3) were correlated with clinical outcome parameters (Table 27). TNF-α correlated inversely with liver dysfunction (r=−0.42, p=0.09), IL-8 with length of hospital stay (r=0.54, p=0.004) and MCP-1 with infections (r=0.37, p=0.06), all complications (r=0.43, p=0.03) and length of stay (r=0.37, p=0.06). IL-6 correlated with liver dysfunction (r=0.49, p=0.01), infections (r=0.38, p=0.06), complications (r=0.38, p=0.06) and length of stay (r=0.48, p=0.01), while IL-10 correlated with length of stay (r=0.41, p=0.03). CRP, adiponectin and TGF-α levels at the end of surgery (S3, for CRP) or immediately following the surgery (24 h, for adiponectin and TGF-α) also correlated with clinical outcomes (Table 27). CRP correlated with infections (r=0.58, p=0.04) while TGF-α correlated with infections (r=0.60, p=0.01) and complications (r=0.47, p=0.06).

Intervention Alters Apoptosis and Necrosis of Hepatocytes

Figure 13:
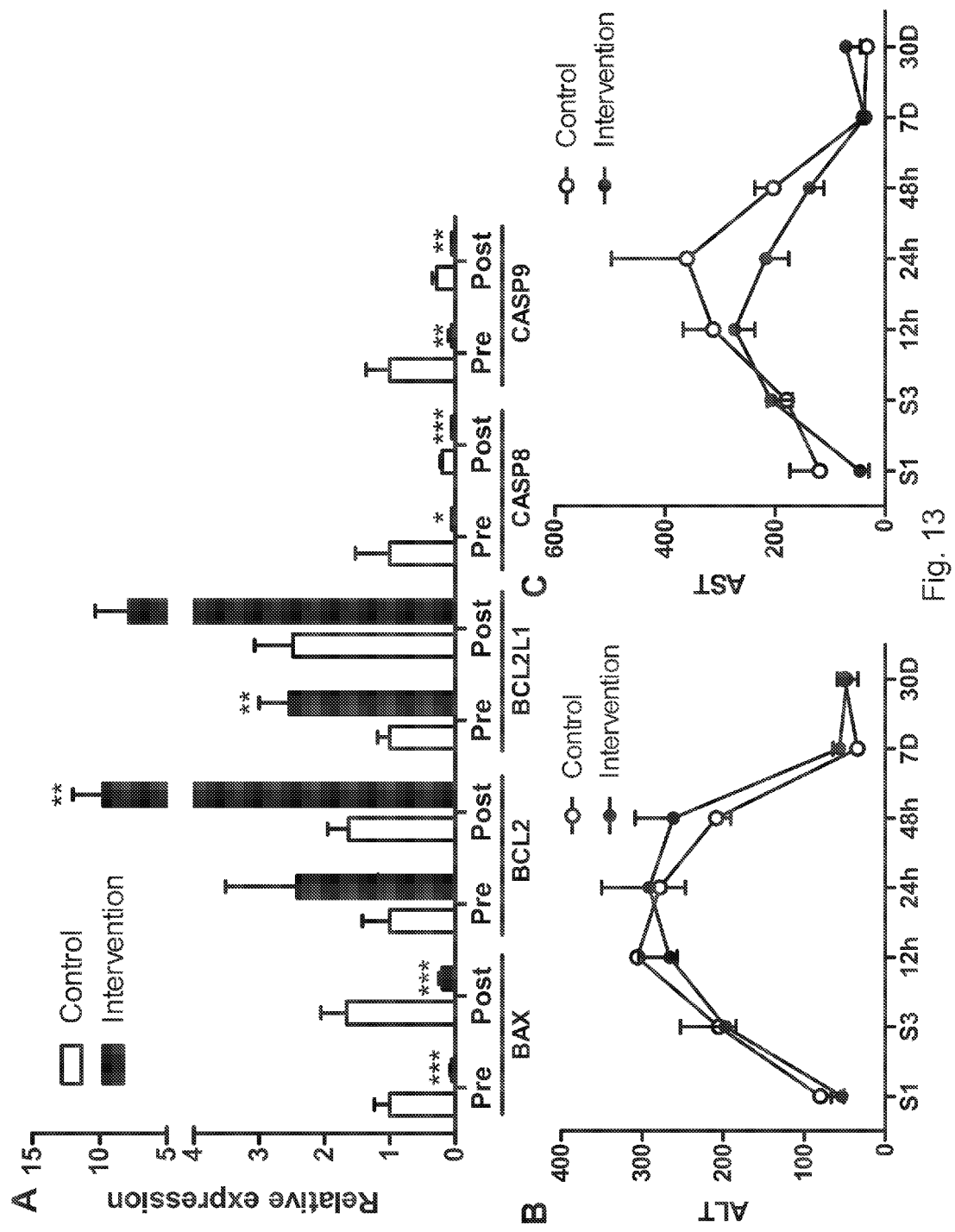
FIG. 13 illustrates apoptosis and liver function markers; A) Relative expression of genes related to apoptosis. Values for each gene are relative to pre-surgery control group values. B) Circulating ALT during and up to 30 days post-surgery. C) Circulating AST during and up to 30 days post-surgery. Data are presented as mean±SEM. BAX, B-cell lymphoma 2-associated X protein; BCL2, B-cell lymphoma 2 protein; BCL2L1, B-cell lymphoma 2-like protein; CASP8, caspase 8; CASP9, caspase 9; ALT, alanine transaminase; AST, aspartate transaminase. *P<0.1; P<0.05; *P<0.01. For controls, n=7-8, for intervention, n=7-8 (A). For controls, n=9-11, for intervention, n=17-19 (B-C).

The effects of the intervention on genes involved in apoptosis were evaluated in biopsies taken at the beginning (Pre) and at the end of the surgery (Post) (FIG. 13A). Genes involved in protection from programmed cell death such as BCL2 (post, p<0.05) or BCL2L1 (pre, p<0.05, post, p=0.13) were increased in the intervention group either prior and/or post-surgery. By contrast, pro-apoptotic genes such as BAX (pre & post, p<0.01), caspase 8 (CASP8, pre, p<0.1, post, p<0.01) and caspase 9 (CASP9, pre & post, p<0.05) had lower hepatic expression in the intervention group.

Post-surgery mRNA levels of apoptosis-related genes was correlated with several biochemical markers related to energy stores, hormones and cytokines (Table 28). Anti-apoptotic gene BCL2 correlated with TNF-α(r=0.75, p=0.05), IL-8 (r=0.87, p=0.01), MCP-1 (r=0.74, p=0.06), insulin (r=0.89, p=0.02) and liver glycogen (r=0.75, p=0.05) at the end of the surgery. As well, the anti-apoptotic gene BCL2L1 correlated with insulin (r=0.84, p=0.02) and correlated inversely with TGF-α (r=−0.77, p=0.08). Pro-apoptotic gene BAX correlated inversely with insulin (r=−0.91, p=0.01) and glycogen (r=−0.90, p=0.005). CASP8 correlated with CRP (r=0.98, p=0.005) and correlated inversely with TNF-α(r=−0.65, p=0.08), insulin (r=−0.78, p=0.04) and glycogen (r=−0.74, p=0.03). CASP9 correlated with CRP (r=0.87, p=0.06) and correlated inversely with insulin (r=−0.81, p=0.03) and glycogen (r=−0.83, p=0.01):

The extent of liver damage was assessed with two liver function markers, alanine transaminase (ALT) an enzyme specific to hepatocytes, indicative of liver damage, and aspartate transaminase (AST) a non-specific marker of acute hepatic damage. Both ALT and AST levels increased during the surgery and reached a peak 24 h post-surgery (FIG. 3B-C). Interestingly, the extent of the rise was altered by the intervention in a marker-specific fashion. While the ALT peak did not change significantly, the overall AST peak was decreased, suggesting that general surgery-related trauma was decreased, consistent with the persistently lower IL-6 and CRP levels.

Discussion

Overall, the plasma and liver expression profile suggests that intervention with insulin-glucose therapy results in increased availability of hepatic energy stores with increased glycogen and better insulin sensitivity during the surgery with increased adiponectin levels. A rapid and transient increase in proflammatory cytokines involved in the regenerative response such as TNF-α, MCP-1 and adiponectin, was more pronounced in the intervention patients. Increased protection from cell death with increased anti-apoptotic genes such as BCL2 and BCL2L1, decreased pro-apoptotic gene expression of BAX, CASPB, CASP9, and lower related cytokines such as IL-6, IL-10 and CRP was also noted in intervention patients.

It is important to discuss baseline differences between the intervention and the control group, as the intervention group is significantly older. Older age is a well-known risk factor for increased liver dysfunction, and this difference may, if anything, have hindered the measurable benefits of the intervention. Clinical benefits from the insulin-glucose therapy may therefore be even greater in age-paired cohorts.

The changes in levels of circulating or gene expression parameters related to the complement system (C3, ASP (C3adesArg), C5adesArg, C5aR, C3aR, C5L2) between intervention and control patients suggest that complement system, while important in regeneration, is not responsible for the beneficial effects of the insulin therapy protocol.

Animal studies have demonstrated conflicting liver repair actions of IL-6 depending on length of exposure. Hepatocyte death that arises through apoptosis represents a major complication from liver resection, and IL-6 has been postulated to play a central role: while acute upregulation of IL-6 improved hepatic regeneration and repair, chronic exposure abolished the protective effects of IL-6 and increased the likelihood of liver failure through apoptosis. The authors suggested that pro-apoptotic effects of IL-6 are potentially mediated through increased induction of the mitochondrial destabilizing pro-apoptotic protein BAX and associated CASP9 activation. In the present study, increased IL-6 levels in the control patients may therefore contribute to postoperative liver dysfunction through a pro-apoptotic BAX pathway. That BAX and CASP9 expressions were substantially lower, as was IL-6, in intervention patients suggests our protocol benefits are partially obtained via these protective mechanisms in response to surgical trauma. This theory is further supported by the correlation of high IL-6 postoperative levels with negative clinical outcomes (Barton, M et al. Pediatric Transplantation 2010: 14; 852-858; Ioannidou E., et al. J. Periodontol. 2006: 11; 1871-8).

In addition to its role in apoptosis, the role of IL-6, together with IL-10, in infection has received attention. Among several cytokines, chemokines and stress hormones investigated postoperatively in liver resection patients, Kimura et al determined a strong significant relationship between IL-6, IL-10, and infection. Increased IL-6 both pre- and postoperatively also accurately predicted onset of infection in cardiac surgery patients receiving perioperative tight glucose control therapy. Surgical trauma related stimulation of IL-6 release, leading to immunosuppression, was cited as a possible cause for increased risk of infection in both studies. Several other studies have proposed IL-10 as a deactivating cytokine capable of increasing infection susceptibility when elevated. The negative roles of IL-6 and IL-10 were also seen in the present study, as peak levels of both cytokines correlated with negative clinical outcomes. Further supporting the protective role of the insulin therapy intervention, IL-6 and IL-10 were two of the cytokines elevated in control patients at the end of the surgery.

In the present study, CRP concentrations measured at the various postoperative time points followed similar trends to those seen for IL-6 and IL-10, where higher CRP levels persisted past 7 days, decreasing only at postoperative day 30 in control subjects. Lowering of circulating CRP concentrations in response to insulin was proposed as a factor that reduced organ failure and mortality among critically ill patients receiving tight glucose control therapy. A more rapid return of CRP levels to baseline seen in our study cohort suggests that tight glucose control with the hyperinsulinemic-normoglycaemic clamp more effectively manages the inflammatory response to surgery than does standard glucose management, and as such, is associated with a better patient prognosis.

TNF-α plays a central role in hepatic physiology, as it plays a role in several processes including local inflammation, injury, cell death and proliferation. TNF-α production after liver resection is critical in order to induce a mitogenic response. The circumstances of TNF-α stimulation can radically alter the direct outcomes, from induction of apoptosis to increased proliferation. Upon binding and activation of the cellular signalling cascade, the TNF-α pathway can bifurcate to either Fas-dependent apoptosis or NF-κB-dependant proliferation or inhibition of apoptosis. Higher TNF-α in intervention subjects and correlations between TNF-α levels and pro-apoptotic levels of BCL2, CASP8 and CASP9, and with subsequent postoperative liver dysfunction, all suggest that TNF-α action in patients with intervention followed the protective anti-apoptotic direction.

TNF-α also directly triggers IL-8 secretion by immune cells and hepatocytes, a cytokine not produced under normal conditions. The role of IL-8 in liver resection is still unclear and has been suggested to be linked with severity of surgical trauma. In our study, intervention subjects show higher IL-8 levels. IL-8 levels correlated with anti-apoptotic gene BCL2 but also surprisingly correlated with length of hospital stay.

The same can be said of MCP-1, which has been found to be elevated in some cases of acute inflammation or complications post-resection. We have found the same association in this study, with correlations between peak MCP-1 levels and several negative clinical outcomes. Our protocol however induced a modest rise in MCP-1 but a decrease in most negative clinical outcomes. The action of MCP-1 has not yet been clearly linked with regenerative biological processes or clinical outcomes and results from this study suggest conflicting roles.

TGF-α is another factor that was correlated with clinical outcomes and reduced in intervention patients. The clear role of TGF-α is yet unknown, and the lack of association with apoptotic markers suggest that TGF-α could contribute to the clinical benefits through a different pathway.

It is hypothesized here that the insulin therapy, globally, promotes cell survival ultimately through reduced apoptosis, consequent to enhanced energy stores, inflammatome fine-tuning and direct insulin action. Early liver regeneration seems to be delayed by the therapy, which focuses on stabilizing hepatocyte energy reserves and cellular integrity. It is likely that proliferation is only postponed for the better, as post-surgery liver dysfunction and complications were reduced by the intervention. These results also suggest that liver regeneration is a complex process that needs proper organ priming in order to be most effective. Early regeneration under improper energetic and inflammatory conditions can therefore potentially be more harmful than beneficial. This clinical trial showcases a procedure that effectively reduces negative outcomes through liver priming therapy.

Conclusions

The results presented in this study link several clinical outcomes with biological parameters in patients undergoing major liver resection. In particular, insulin therapy reduced postoperative liver dysfunction by suppressing apoptosis. This study demonstrates that a potential method, the hyper-insulinemic-normoglycaemic clamp prior and during liver resection, can alter hepatic response and promote improvements in surgical outcome.

Example 10

High-Dose Insulin Therapy in a HCV Infected Patient

One patient infected with hepatitis C is subjected to a high-dose insulin therapy according to the schedule shown in Table 29. Following multiple administrations of GIN clamp, the liver scores are improved. Specifically, the level of billirubin changes significantly, which impacts significantly on the liver score, measured either by the Child-Pugh scoring system or the MELD scoring system.

TABLE 29

Insulin infusion schedule of one individual suffering from Hepatitis C

| date | S1 04-avr | S2 06-avr | S3 12-avr | S4 14-avr | S5 19-avr | S6 21-avr | S7 26-avr | S8 28-avr | S9 02-mai | S10 10-mai |
|---|---|---|---|---|---|---|---|---|---|---|
| Total insulin infused (units) | 57 | 56 | 54.2 | 49.5 | 50 | 52 | 54 | 52 | 51 | 53.2 |
| Patient weight | 76 | 76.3 | 76.1 | 76.2 | 76.2 | 79.5 | 79.3 | 79 | 78.2 | 77.3 |
| Length (hrs) | 6.75 | 6.5 | 6.5 | 6 | 6 | 5.9 | 6 | 5.75 | 5.9 | 6.1 |
| Total D10 before termination phase | 1436 | 985 | 1347 | 772 | 1130 | 1132 | 1034 | 1232 | 1148 | 832 |
| Boluses | 7 | 1 | 3 | 1 | 3 | 1 | 2 | 2 | 1 | 1 |
| Fasting Glucose | 8.9 | 8.4 | 10.2 | 11.7 | 11.1 | 10 | 17.5 | 10.8 | 10.2 | 11.5 |
| Time before reaching goal range (min) | 55 | 80 | 50 | 130 | 90 | 90 | 100 | 95 | 80 | 135 |
| Maximum rate of dextrose infusion | 400 | 220 | 280 | 220 | 360 | 320 | 320 | 380 | 380 | 280 |
| Maintenance rate | 400 | 220 | 280 | 280 | 360 | 320 | 320 | 380 | 360 | 280 |
| Insulin infusion rate (u/hr) | 9.1 | 9.1 | 9.1 | 9.1 | 9.1 | 9.5 | 9.5 | 9.5 | 9.4 | 9.3 |

| date | S11 12-mai | S12 17-mai | S13 19-mai | S14 24-mai | S15 26-mai | S16 02-juin | S17 07-juin | S18 09-juin | S19 14-juin |
|---|---|---|---|---|---|---|---|---|---|
| Total insulin infused (units) | 54 | 54 | 54.9 | 58 | 55.4 | 50.2 | 55 | 55.6 | 55.3 |
| Patient weight | 77.8 | 77.8 | 78.3 | 77 | 77.8 | 77.5 | 77.7 | 78 | 77.8 |
| Length (hrs) | 6 | 6 | 6.1 | 6.4 | 6.1 | 5.8 | 6 | 6 | 6 |
| Total D10 before termination phase | 750 | 1260 | 880 | 1196 | 1037 | 1040 | 852 | 970 | 1118 |
| Boluses | 0 | 3 | 2 | 3 | 2 | 0 | 1 | 0 | 1 |
| Fasting Glucose | 14.7 | 12.3 | 14.8 | 13.4 | 13.4 | 12.4 | 13.8 | 15.3 | 17.4 |
| Time before reaching goal range (min) | 135 | 100 | 130 | 105 | 95 | 85 | 125 | 120 | 105 |
| Maximum rate of dextrose infusion | 280 | 420 | 300 | 360 | 300 | 280 | 300 | 300 | 380 |
| Maintenance rate | 240 | 360 | 300 | 360 | 300 | 280 | 260 | 260 | 300 |
| Insulin infusion rate (u/hr) | 9.3 | 9.3 | 9.4 | 9.3 | 9.3 | 9.3 | 9.3 | 9.4 | 9.3 |

TABLE 30

Laboratory results from one individual suffering from Hepatitis C treated with high dose of insulin

| set | CBC_N# | CBC_M# | CBC_Plt | CDC_R | CDC_W | Hgb | PT | PTT | INR |
|---|---|---|---|---|---|---|---|---|---|
| 1 | 2.02 | 0.38 | 66 | 4.62 | 4.48 | 155 | 13.8 | 33.3 | 1.07 |
| 2 | 1.98 | 0.38 | 74 | 4.81 | 4.35 | 159 | 13.9 | 31.1 | 1.08 |
| 3 | 1.92 | 0.34 | 61 | 4.38 | 4.08 | 143 | 13.1 | 27 | 1 |

TABLE 30-continued

Laboratory results from one individual suffering from Hepatitis C treated with high dose of insulin

| set | AFP | ALT | AST | ALP | GGT | Bili_T | Urea | Creat |
|---|---|---|---|---|---|---|---|---|
| 1 | 18 | 138 | 159 | 166 | 269 | 43 | 3.9 | 65 |
| 2 | 9 | 220 | 159 | 122 | 120 | 39 | 3.4 | 46 |
| 3 | 4 | 134 | 108 | 100 | 78 | 25 | 2.9 | 50 |

| set | estimated gfr | Albu | Sodium | Potassium | HCV PCR | Insulin_F | Glucose_F |
|---|---|---|---|---|---|---|---|
| 1 | 104 | 36 | 141 | 4.2 | | | |
| 2 | 119 | 39 | 138 | 3.7 | 7244360 | 82.5 | 10.2 |
| 3 | 115 | 37 | 137 | 4.5 | refused | 102.4 | 12.7 |

| set | HBA1C | HOMA_IR | Cortisol | C3 | C4 | Cholestrol |
|---|---|---|---|---|---|---|
| 1 | | | | | | |
| 2 | 7.9 | 1.8 | | 0.9 | 0.08 | 3.57 |
| 3 | 8 | 2.4 | 302 | 0.96 | 0.1 | 3.8 |

| set | TG | HDL | LDL | Chol/HDL | CRP | Lipase | Child | MELD | Bx |
|---|---|---|---|---|---|---|---|---|---|
| 1 | | | | | | | 6 | 8 | (in JGH) insuffecient |
| 2 | 0.93 | 1.11 | 2.04 | 3.2 | 0.8 | 31 | 6 | 6 | |
| 3 | 2.46 | 0.89 | 1.79 | 4.3 | 1.2 | 26 | 5 | 6 | |

Example 11

Human Islets of Langerhans from GIN Clamp Donor

Figure 14:
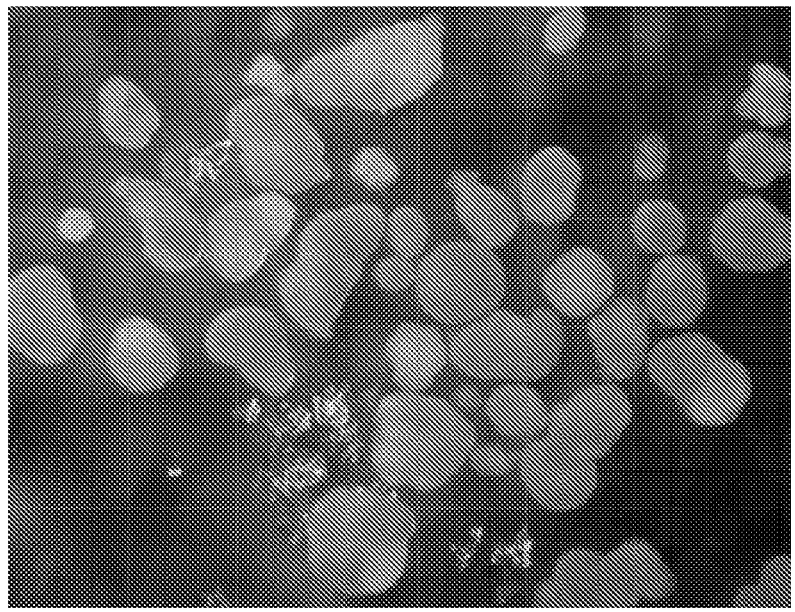
FIG. 14 illustrates Human islets of Langerhans from a GIN clamped donor stain positive for zinc-containing insulin granules after 6 weeks in culture.
Figure 15:
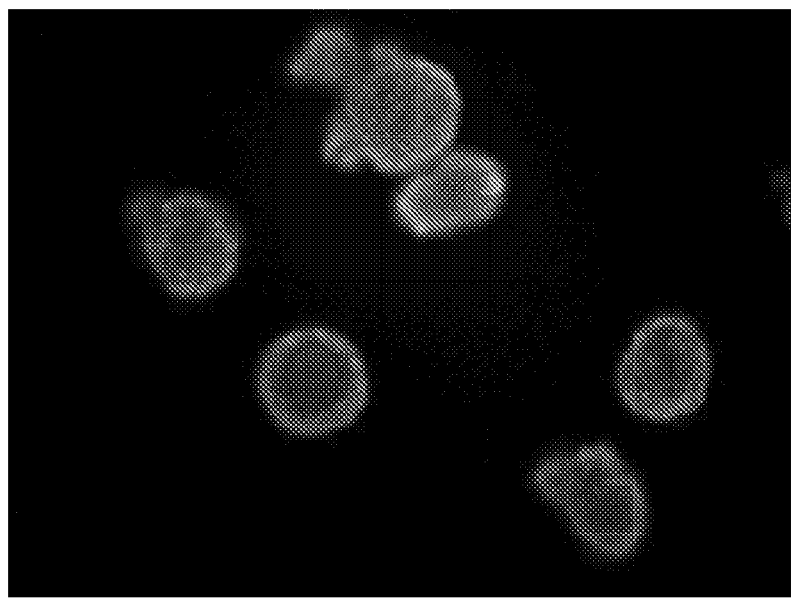
FIG. 15 illustrates Human islets of Langerhans from a GIN clamped donor remain viable after 6 weeks in culture. Islets were stained for viability with membrane exclusion dyes SYTO Green (green; viable) and ethidium bromide (red; dead cells—none shown).

Islets of Langerhans are purified from a donor pancreas where the deceased donor was administered the GIN clamp prior to organ retrieval, followed by islet isolation procedures. Contrary to standard practice the islets are kept for 7 weeks in culture. By 7 weeks, non-treated purified islets are normally reduced significantly both in number and in quality (ie. responsiveness to releasing insulin in-vitro to a glucose challenge. Now referring to FIG. 14, human islets of Langerhans from a GIN clamped donor stain positive for zinc-containing insulin granules after 6 weeks in culture. Typically islets diminish in culture within one month. Also, referring to FIG. 15, the human islets of Langerhans from a GIN clamped donor were stained for viability with membrane exclusion dyes SYTO Green (green; viable) and ethidium bromide (red; dead cells—none shown). As shown in Table 31, the hyperinsulinemic normoglycemic clamping of a deceased donor pancreas resulted in high purity, viability and yield of isolated islets of Langerhans, despite lengthy cold ischemic time which is normally associated with poor outcomes. Even following 7 weeks in culture, the hyperinsulinemic normoglycemic clamping of a deceased donor pancreas resulted in significantly higher viability (approx. 50%) of islets of Langerhans and responsiveness (ie. insulin secretion) to glucose challenge as compared to islets isolated from a unclamped donor.

TABLE 31

Donor parameters and islets of Langerhans cell quality.

| Age | Body Mass Index | Cold Ischemic Time (hrs) | Purity (%) | Viability (%) | Yield (Islet Equivalents) |
|---|---|---|---|---|---|
| 58 | 25.75 | 17.9 | 98 | 98 | 271 296 |

Example 12

Association of Preoperative Glycemic Control, Intraoperative Insulin Sensitivity, and Outcomes after Cardiac Surgery Context:
The impairment of insulin sensitivity, a marker of surgical stress, is important for outcomes.

Objective:
The aim is to assess the association between the quality of preoperative glycemic control, intraoperative insulin sensitivity, and adverse events after cardiac surgery.

Design and Setting:
A prospective cohort study is conducted at a tertiary care hospital.

Subjects:
Nondiabetic and diabetic patients scheduled for elective cardiac surgery are included in the study. Based on their glycosylated hemoglobin A (HbA$_{1c}$), diabetic patients are allocated to a group with good (HbA$_{1c}$<6.5%) or poor (HbA$_{1c}$>6.5%) glycemic control.

Intervention:
The hyperinsulinemic-normoglycemic clamp technique is used.

Main Outcome Measures:
The primary outcome is insulin sensitivity measurement. Secondary outcomes are major complications within 30 d after surgery including mortality, myocardial failure, stroke, dialysis, and severe infection (severe sepsis, pneumonia, deep sternal wound infection). Other outcomes included minor infections, blood product transfusions, and the length of intensive care unit and hospital stay.

Results:
A total of 143 nondiabetic and 130 diabetic patients are studied. In diabetic patients, a negative correlation (r=−0.527; P<0.001) is observed between HbA$_{1c}$ and intraoperative insulin sensitivity. Diabetic patients with poor glycemic control had a greater incidence of major complications (P=0.010) and minor infections (P=0.006). They received more blood products and spent more time in the intensive care unit (P=0.030) and the hospital (P<0.001) than nondiabetic patients. For each 1 mg·kg$^{-1}$·min$^{-1}$ decrease in insulin sensitivity, the incidence of major complications increased (P=0.004).

Conclusions:

In diabetic patients, HbA$_{1c}$ levels predict insulin sensitivity during surgery and possibly outcome. Intraoperative insulin resistance is associated with an increased risk of complications, independent of the patient's diabetic state.

Subjects and Methods

Patients scheduled for elective coronary artery bypass grafting (CABG), valve procedure, or a combination of both are approached at the Royal Victoria Hospital. Patients scheduled for off-pump CABG, emergency procedures, or procedures with anticipated deep hypothermic circulatory arrest are excluded. Also excluded are patients who are on hemodialysis or have troponin I levels of at least 0.5 ng/liter.

Patients not known for diabetes presenting with blood glucose levels greater than 7.0 mmol/liter or HbA$_{1c}$ greater than 6.0% also are not eligible. Only patients with a confirmed diagnosis of type 2 diabetes mellitus and receiving treatment (oral antihyperglycemic agents, or insulin) are considered diabetic. Based on their HbA$_{1c}$ concentrations, diabetics are allocated to a group with good (HbA$_{1c}$<6.5%) or poor (HbA1c>6.5%) glycemic control.

Patients receive standardized iv anesthesia using sufentanil and midazolam supplemented with inhaled sevoflurane. During cardiopulmonary bypass (CPB), mean arterial pressure is maintained between 50 and 70 mmHg. Moderate hemodilution (hematocrit 20-25%) and mild hypothermia (34° C.) are tolerated during CPB.

Insulin sensitivity is assessed by the hyperinsulinemic-normoglycemic clamp technique. Before induction of anesthesia, insulin (Humulin R; Eli Lilly&Company, Indianapolis, Ind.) is administered IV at 5 mU·kg$^{-1}$·min$^{-1}$. Approximately 10 min after starting the insulin infusion, and when the blood glucose was less than 6.1 mmol/liter, dextrose 20% supplemented with phosphate (30 mmol/liter) is administered. Arterial blood glucose concentrations are determined every 5 min, and the dextrose infusion is adjusted to maintain blood glucose at 5.0 mmol/liter (90 mg/dL). The dextrose infusion rate during steady-state conditions, before and toward the end of CPB, is used as an indicator of insulin sensitivity. Steady-state conditions is assumed if the coefficient of variation of five subsequent dextrose infusion rates is less than 5%.

At the end of surgery (skin closure), the insulin infusion is stopped. The dextrose infusion is maintained for 2 h to avoid hypoglycemia. In the intensive care unit (ICU), following the routine guidelines for this patient population at the Royal Victoria Hospital, an insulin sliding scale is applied aiming at a blood glucose between 4.0 and 8.0 mmol/liter. Blood glucose is measured every 1 to 2 h, and the average blood glucose during the first 24 h after surgery is calculated.

Complications are assessed 30 days after surgery. Major complications included all-cause mortality, myocardial failure (cardiac index□1.8 liter·min$^{-1}$·m$^{-2}$ and mixed venous saturation □55%, despite adequate fluid replacement, and high-dose inotropic support requiring either intraaortic balloon pump, right and/or left ventricular assist device, and/or extracorporeal mechanical oxygenation after separation from CPB), stroke (new focal or global neurological deficit confirmed by clinical findings and computed tomographic scan), dialysis, and serious infection (severe sepsis, pneumonia requiring mechanical ventilation, deep sternal wound infection). Other complications include minor infections such as pneumonia not requiring mechanical ventilation, superficial wound and urinary tract infection, and blood product transfusions. Also documented are the peak postoperative creatinine plasma concentration, the duration of intubation, as well as length of ICU and hospital stay.

Patient demographics, blood glucose concentrations, and insulin sensitivity are compared using one-way ANOVA with Tukey-Kramer multiple comparisons posttest or $\chi^2$ test for categorical variables. The paired t test is used for comparisons within groups regarding changes in intraoperative insulin sensitivity. Stepwise multiple regression analysis is performed between intraoperative insulin sensitivity and preoperative patient variables including age, body weight, body mass index, HbA$_{1c}$ concentration, fasting blood glucose concentration, mean blood pressure, and plasma creatinine.

The difference in the incidence of complications is analyzed by the Kruskal-Wallis test with Steel-Dwass multiple comparisons posttest or □$\chi^2$ test for categorical variables. The Pearson correlation coefficient and linear regression are used to describe the association between plasma HbA$_{1c}$ and insulin sensitivity as expressed by the dextrose infusion rate during steadystate conditions toward the end of CPB. A logistic regression model assesses the relationship between insulin sensitivity and adverse outcomes while adjusting for potential confounders. Variables in Table 32 are put into the multivariable model. Two-sided P values less than 0.05 are considered statistically significant. Sample size is calculated on the basis of the primary study hypothesis assuming a negative correlation between plasma HbA$_{1c}$ and insulin sensitivity during CPB. A sample size of 120 achieves 80% power to detect a slope of 0.5 under the alternative hypothesis when the SD of the HbA$_{1c}$ is 2, the SD of the dextrose infusion rate is 4, and the significance level is 0.05.

TABLE 32

Demographics

|  | Non-DM | DM HbA$_{1c}$ < 6.5% | DM HbA$_{1c}$ > 6.5% |
|---|---|---|---|
| n | 143 | 61 | 69 |
| Age (yr) | 65 ± 14 | 68 ± 9 | 66 ± 10 |
| Body mass index (kg/m$^2$) | 27.5 ± 5.1 | 28.5 ± 5.7 | 29.2 ± 5.9 |
| Gender (males/females) | 109/34 | 43/18 | 48/21 |
| HbA$_{1c}$ (%) | 5.4 ± 0.3 | 6.1 ± 0.3[c] | 7.6 ± 0.9[a, b] |
| Parsonnet score | 17 ± 11 | 19 ± 10 | 18 ± 11 |
| Euro score | 3.0 ± 1.8 | 3.2 ± 1.5 | 3.1 ± 1.8 |
| Ejection fraction (%) | 52 ± 11 | 51 ± 12 | 50 ± 12 |
| ACE inhibitors | 79 (55.2) | 36 (59.0) | 42 (61.0) |
| β-Blockers | 98 (68.5) | 47 (77.0) | 48 (70.0) |
| Ca channel-blockers | 34 (23.8) | 21 (34.4) | 20 (29.0) |
| Statins | 98 (68.5) | 48 (78.7) | 54 (78.3) |
| Corticosteroids | 6 (4.2) | 2 (3.3) | 3 (4.3) |
| Insulin | 0 | 14 (23.0) | 19 (27.5) |
| Thiazolidinediones | 0 | 3 (4.9) | 5 (7.2) |
| Biguanides | 0 | 31 (50.8) | 35 (50.7) |
| Sulfonylureas and meglitinides | 0 | 14 (23.0) | 16 (23.2) |
| Hematocrit (%) | 39.0 ± 5.5 | 38.7 ± 5.0 | 38.5 ± 5.6 |
| Creatinine (μmol/liter) | 93 ± 19 | 90 ± 21 | 94 ± 23 |
| Fasting blood glucose (mmol/liter) | 5.6 ± 0.8 | 6.6 ± 1.6[c] | 8.5 ± 2.1[a, b] |
| Mean blood pressure (mmHg) | 84 ± 15 | 85 ± 14 | 85 ± 17 |
| CABG | 86 (60.1) | 35 (57.3) | 43 (62.3) |
| Valve | 29 (20.3) | 12 (19.7) | 12 (17.4) |
| CABG and valve | 28 (19.6) | 14 (23.0) | 14 (20.3) |
| Aortic cross clamp time (min) | 85 ± 33 | 84 ± 28 | 86 ± 31 |
| CPB time (min) | 104 ± 42 | 107 ± 45 | 108 ± 43 |
| Minimum temperature during CPB (C) | 33.7 ± 1.1 | 33.9 ± 1.5 | 34.0 ± 1.4 |

TABLE 32-continued

| | Demographics | | |
|---|---|---|---|
| | | DM | |
| | Non-DM | HbA$_{1c}$ < 6.5% | HbA$_{1c}$ > 6.5% |
| Duration of surgery (min) | 218 ± 63 | 217 ± 55 | 211 ± 56 |

Data are expressed as mean ± SD or number (percent).
DM, Diabetes mellitus;
ACE, angiotensin-converting enzyme.
[a] P < 0.05 non-DM vs. DM HbA$_{1c}$ > 6.5%.
[b] P < 0.05 DM HbA$_{1c}$ < 6.5% vs. DM HbA$_{1c}$ > 6.5%.
[c] P < 0.05 non-DM vs. DM HbA$_{1c}$ < 6.5%.

Results 143 nondiabetic and 130 diabetic patients are studied. Patient demographics are similar in all groups except for plasma HbA$_{1c}$ and fasting blood glucose concentration, which are increased in the two diabetic groups (P≤0.001; Table 32).

Figure 16:
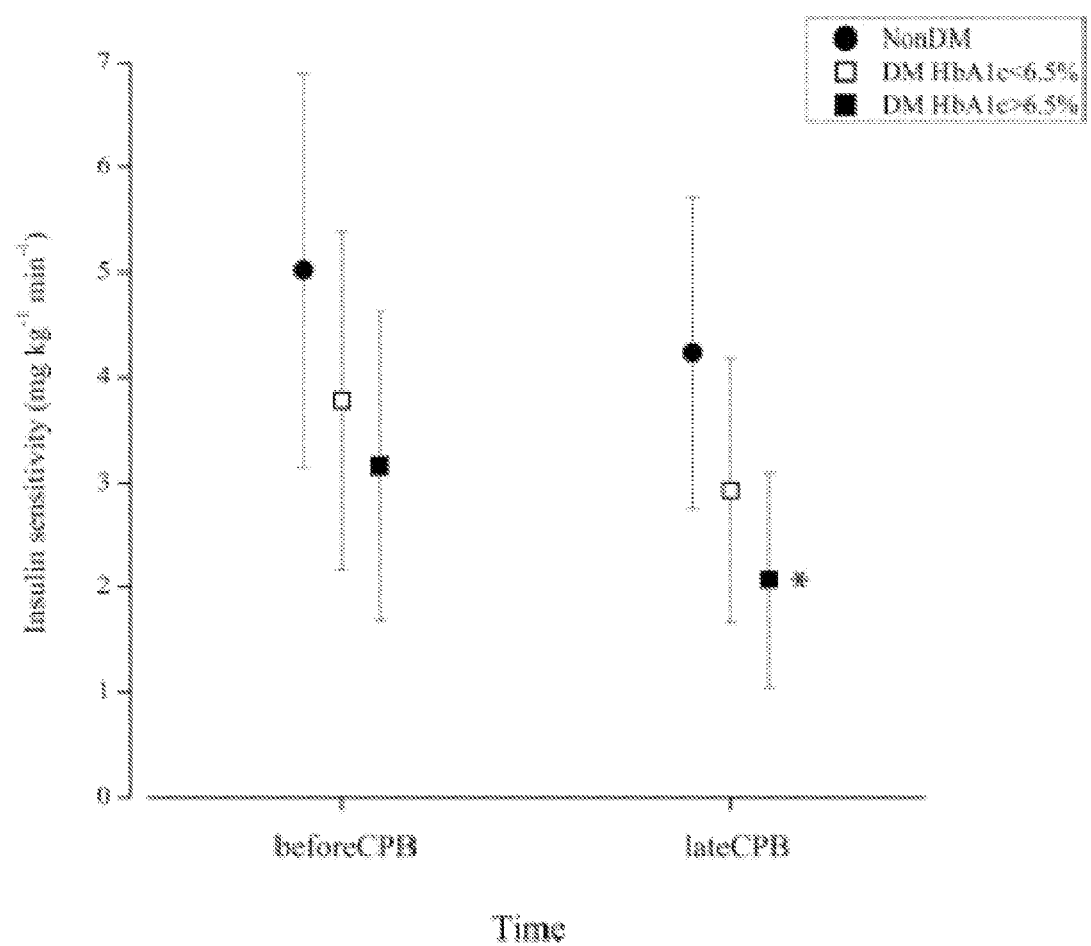
FIG. 16 illustrates Insulin sensitivity in nondiabetic and diabetic patients before and during late CPB (DM HbA1c<6.5%=good glycemic control group; DM HbA1c>6.5%=poor glycemic control group). Data are expressed as means±SD. The dextrose infusion rate (mg·kg$^{-1}$·min$^{-1}$) during steady-state conditions is used as an indicator of insulin sensitivity. Insulin sensitivity during late CPB in diabetic patients with poor preoperative glycemic control was lower than in nondiabetic patients and diabetic patients with good glycemic control. *, P<0.01. DM, Diabetes mellitus; NonDM, non diabetes mellitus; beforeCPB, before CPB; lateCPB, before separation from CPB.

In all patients, insulin sensitivity decreased during CPB when compared with before CPB (P<0.001). Diabetic patients with poor preoperative glycemic control show a greater degree of insulin resistance before separation from CPB (FIG. 16; P<0.001) and an increased blood glucose concentration in the ICU (see Table 34; P<0.001) when compared with well-controlled diabetic and nondiabetic patients.

Figure 17:
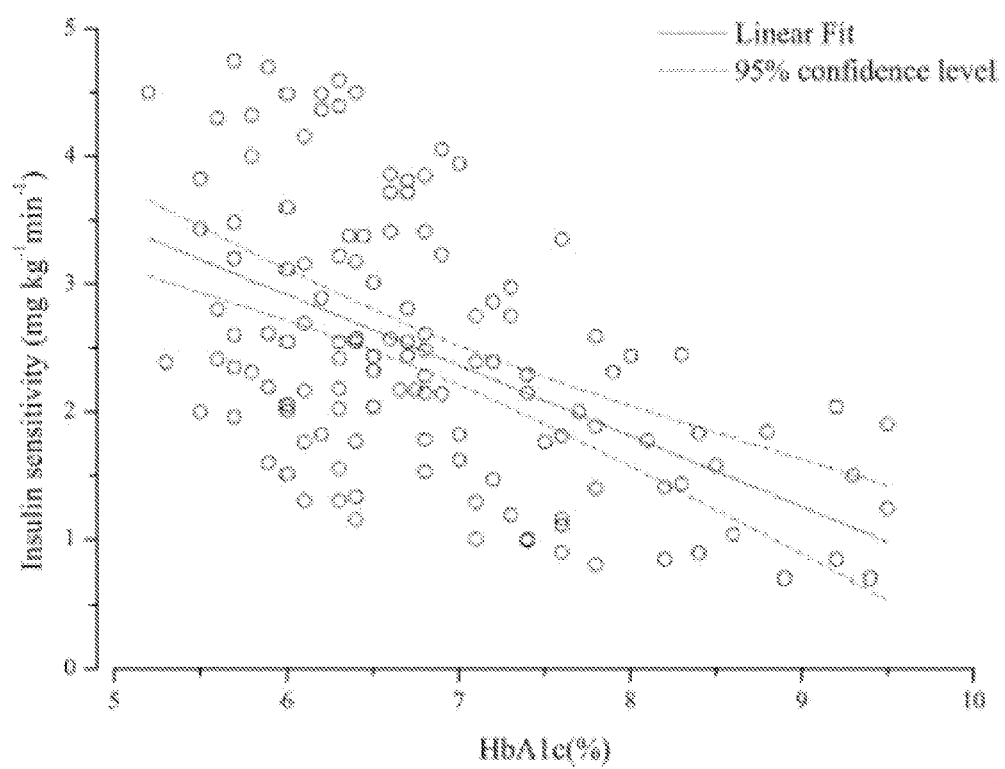
FIG. 17 illustrates the association between preoperative HbA1c levels (%) and insulin sensitivity during late CPB in diabetic patients. The dextrose infusion rate (mg·kg$^{-1}$·min$^{-1}$) during steady-state conditions is used as an indicator of insulin sensitivity. A significant negative correlation is observed between the two variables (Pearson r=−0.527; P<0.001). The linear regression of that relationship can be described as insulin sensitivity=−0.554·[HbA1c]+6.238.

In patients with diabetes, a weak but significant negative correlation (FIG. 17; r=−0.527; P <0.001) is observed between preoperative HbA$_{1c}$ concentrations and insulin sensitivity before separation from CPB.

This relationship can be described as insulin sensitivity=−0.554[HbA$_{1c}$]+6.238.

Furthermore, intraoperative insulin sensitivity negatively correlates with body mass index (Table 33). In nondiabetic patients, negative correlations are observed between insulin sensitivity and body weight, fasting blood glucose, and plasma creatinine (Table 33).

The incidence of complications in nondiabetic patients and diabetic patients with good preoperative glycemic control is similar. The peak creatinine plasma concentration after surgery is higher in well-controlled diabetics than in the nondiabetic study group (P=0.042). The number of patients who suffered a major complication is significantly increased in diabetics with poor preoperative glycemic control when compared with normals (P=0.010; Table 34). Diabetic patients showing a HbA$_{1c}$ concentration greater than 6.5% had a greater incidence of severe (P=0.035) and minor infections (P=0.006), received more blood products (packed red blood cells, P=0.046; fresh frozen plasma, P=0.035; platelets, P<0.001), had a higher peak creatinine level (P=0.011), and spent more time in the ICU (P=0.030) and the hospital (P<0.001) than nondiabetics (Table 34).

Poor preoperative glycemic control is associated with a greater incidence of minor infections when compared with diabetic patients with good glycemic control (P=0.034; Table 34). In particular, the rate of superficial wound infections is increased.

Independent of the presence of diabetes mellitus, for each 1 mg·kg$^{-1}$·min$^{-1}$ decrease in insulin sensitivity, we observed an increased incidence of major complications [odds ratio (OR)=2.23; P=0.004] and severe (OR=4.98; P=0.010) and minor infections (OR=1.97; P=0.003) (Table 35).

TABLE 33

| Stepwise multiple regression analysis | | |
|---|---|---|
| Variable | β-Coefficient | P |
| Nondiabetic patients | | |
| Body weight (kg) | −0.301 | <0.001 |
| Fasting blood glucose (mmol/liter) | −0.180 | 0.015 |
| Creatinine (μmol/liter) | 0.142 | 0.049 |
| Diabetic patients | | |
| HbA$_{1c}$ (%) | −0.494 | <0.001 |
| Body mass index (kg/m$^2$) | −0.222 | 0.004 |

Standardized β-coefficients of correlations between intraoperative insulin sensitivity and variables in nondiabetic and diabetic patients.

TABLE 34

| | Outcomes | | |
|---|---|---|---|
| | | DM | |
| | Non-DM | HbA$_{1c}$ < 6.5% | HbA$_{1c}$ > 6.5% |
| n | 143 | 61 | 69 |
| Major complications | 9 (6.2) | 7 (11.5) | 12 (17.4)[a] |
| Death | 3 (2.1) | 2 (3.3) | 4 (5.8) |
| IABP | 3 (2.1) | 1 (1.6) | 2 (2.9) |
| Dialysis | 2 (1.4) | 1 (1.6) | 3 (4.3) |
| Stroke | 1 (0.7) | 2 (3.3) | 1 (1.6) |
| Severe Infection | 3 (2.1) | 2 (3.3) | 6 (8.7)[a] |
| Septic shock | 1 (0.7) | 0 (0) | 1 (1.4) |
| Pneumonia (requiring ventilation) | 1 (0.7) | 1 (1.6) | 3 (4.3) |
| DSWI | 1 (0.7) | 1 (1.6) | 2 (2.9) |
| Other complications | | | |
| Minor infection | 14 (9.8) | 8 (13.1) | 19 (27.5)[a,b] |
| Pneumonia (not requiring ventilation) | 5 (3.5) | 3 (4.9) | 5 (7.2) |
| Superficial wound infection | 6 (4.2) | 5 (8.2) | 8 (11.6)[a] |
| UTI | 8 (5.6) | 4 (6.6) | 8 (11.6) |
| Blood transfusion | | | |
| RBC | 88 (61.5) | 41 (67.2) | 52 (75.4)[a] |
| Units/patient | 3.0 (2.0-5.0) | 2.5 (2.0-5.0) | 3.0 (2.0-6.0) |
| FFP | 34 (23.8) | 19 (31.1) | 26 (37.7)[a] |
| Units/patient | 3.0 (2.0-4.0) | 2.9 (2.1-4.0) | 4.0 (2.0-6.6) |
| Platelets | 27 (18.9) | 18 (29.5) | 28 (40.6)[a] |
| Units/patient | 5.8 (5.0-10.0) | 6.0 (5.0-7.5) | 6.4 (5.0-10.2) |
| Blood glucose in ICU (mmol/liter) | 7.8 ± 1.4 | 8.3 ± 1.9 | 9.3 ± 2.9[a,b] |
| Creatinine (μmol/liter) | 106 (90-131) | 119 (100-144)[c] | 135 (100-166)[a] |
| Intubation time (h) | 7.8 (4.8-13.8) | 8.8 (6.0-17.5) | 9.3 (6.0-18.0) |
| ICU stay (h) | 20 (19-26) | 21 (20-44) | 25 (20-46)[a] |
| Hospital stay (d) | 8 (6-12) | 8 (7-15) | 11 (9-16)[a] |

Data are expressed as number (percent), median (interquartile range), or mean ± SD
DM, Diabetes mellitus;
IABP, intraaortic balloon pump,
DSWI, deep sternal wound infection;
UTI, urinary tract infection;
RBC, red blood cell;
FFP, fresh frozen plasma.
[a] P < 0.05 non-DM vs. DM HbA$_{1c}$ > 6.5%.
[b] P < 0.05 DM HbA$_{1c}$ < 6.5% vs. DM HbA$_{1c}$ > 6.5%.
[c] P < 0.05 non-DM vs. DM HbA$_{1c}$ < 6.5%.

TABLE 35

OR of outcomes for every decrease in insulin sensitivity by $1 \text{ mg} \cdot \text{kg}^{-1} \cdot \text{min}^{-1}$

| Outcome | OR (95% CI) | P value |
|---|---|---|
| Major complications | 2.23 (1.30-3.85) | 0.004 |
| Death | 2.33 (0.94-5.78) | 0.067 |
| IABP | 1.55 (0.66-3.66) | 0.318 |
| Dialysis | 1.79 (0.52-6.18) | 0.359 |
| Stroke | 2.60 (0.64-10.5) | 0.181 |
| Severe infection | 4.98 (1.48-16.8) | 0.010 |
| Minor infection | 1.97 (1.27-3.06) | 0.003 |

The ORs were adjusted for potential confounders.
CI, Confidence interval;
IABP, intraaortic balloon pump.

Discussion

The results of the present study demonstrate that in diabetic patients there is a weak, but significant, association between the quality of preoperative glycemic control and insulin sensitivity during cardiac surgery. The results further suggest that insulin resistance during surgery, rather than the presence of diabetes mellitus, is associated with an increased risk of major complications. At present, methodological tools that would allow to anticipate the degree of tissue insulin resistance and the hyperglycemic response during surgery are lacking. Taking into account the link between insulin resistance, hyperglycemia, and circulating $HbA_{1c}$ concentrations, the finding that preoperative plasma $HbA_{1c}$ levels predict intraoperative insulin resistance in diabetic patients is not unexpected. The patients' body mass index also is associated with insulin sensitivity. This association, is weaker than that with $HbA_{1c}$, however, is also observed in nondiabetic patients.

Although $HbA_{1c}$ values have been widely investigated as an index of long-term blood glucose control and outcome predictors in diabetic patients, its predictive value in the surgical patient population has received little attention. In agreement with our findings demonstrating worse outcomes in the presence of increased HbA1c values, it is showed that diabetic patients with elevated HbA1c levels had an augmented adverse event rate and a higher 30-d mortality after cardiac procedures. In another small cohort of presumably nondiabetic patients, elevated HbA1c concentrations are associated with an increased risk of complications after vascular surgery. If it holds true that poor preoperative glycemic control adversely affects outcomes of diabetic patients, it remains to be studied whether the timely improvement of glycemic control before surgery reduces complications as seen in the medical patient population.

The impairment of tissue insulin sensitivity is the primary cause of perioperative hyperglycemia and the diabetes of the injury. Due to the specific metabolic and endocrine alterations induced by extracorporeal circulation, insulin sensitivity not surprisingly decreases during CPB in all patients, with poorly controlled diabetic patients showing the greatest decline. Although hyperglycemia has been shown to be an independent risk factor for death, cardiovascular, respiratory, infectious, and renal complications in nondiabetic and diabetic surgical patients, the clinical significance of altered insulin sensitivity is unknown. Furthermore, it is still controversial whether the diagnosis of diabetes mellitus per se or the actual degree of insulin dysfunction and hyperglycemia contributes to mortality and morbidity in patients undergoing cardiac surgery. This controversy is illustrated by the fact that only eight of 19 preoperative risk assessment scores include diabetes mellitus.

Studies in nondiabetic patients undergoing open cholecystectomy show a 50% reduction of postoperative insulin sensitivity with unclear impact on outcome. The present study demonstrates, to our knowledge for the first time, a significant association between the magnitude of insulin resistance during cardiac surgery and outcome, independent of the patient's diabetic state. This finding lends further support to the previously held contention that, perioperatively, alterations in glucose homeostasis are better predictors of adverse events than the presence of diagnosed or suspected diabetes mellitus.

Because perioperative administration of dextrose has been shown to reduce insulin resistance and improve outcomes after noncardiac surgery, applying the hyperinsulinemic-normoglycemic clamp itself might have influenced the incidence of complications. However, all patients enrolled in the present protocol received identical treatment.

Although patients not known for diabetes and presenting with blood glucose levels greater than 7.0 mmol/liter or HbA1c greater than 6.0% are not eligible, we cannot entirely exclude the possibility that some patients who are labelled "nondiabetic" actually had diabetes mellitus.

Because there is no accepted HbA1c value to distinguish between diabetic patients with good and poor glycemic control, using an HbA1c value of 6.5% is, to some extent, arbitrary. The decision to use 6.5% in the present protocol is based on recent recommendations.

In conclusion, in diabetic patients preoperative HbA1c levels predict insulin sensitivity during cardiac surgery and, possibly, outcome. Independent of the patient's diabetic state, intraoperative insulin resistance is associated with an increased risk of complications after surgery.

Example 13

Perioperative Glucose and Insulin Administration while Maintaining Normoglycemia (GIN Therapy) in Patients Undergoing Major Liver Resection Background:

Although hyperglycemia is a well-recognized risk factor in the context of cardiac surgery, the relevance of perioperative glycemic control for patients undergoing major noncardiac operations has received little attention. A study is designed to assess the hyperglycaemic response to liver resection, and to test the hypothesis that perioperative glucose and insulin administration while maintaining normoglycemia (GIN therapy) provides glycemic control superior to that achieved by the conventional use of insulin.

Methods:

Patients are randomly assigned to GIN therapy or standard therapy (control group). In the GIN therapy group, insulin was administered at $2 \text{ mU} \cdot \text{kg}^{-1} \cdot \text{min}^{-1}$ during surgery. At the end of surgery, the insulin infusion was decreased to $1 \text{ mU} \cdot \text{kg}^{-1} \cdot \text{min}^{-1}$ and continued for 24 hours. Dextrose 20% was infused at a rate adjusted to maintain blood glucose within the target range of 3.5 to 6.1 mmol/L (63-110 mg/dL). Patients in the standard therapy group received a conventional insulin sliding scale during and after surgery. The mean and SD of blood glucose as well as the percentage of blood glucose values within the target range were calculated. To evaluate intrasubject variability, the coefficient of variability (CV) of blood glucose was calculated for each patient. Episodes of severe hypoglycemia, i.e., blood glucose<2.2 mmol/L (40 mg/dL), are recorded. The primary outcome is the proportion of normoglycemic measurements.

Results:

We studied 52 patients. The mean blood glucose value in patients receiving GIN therapy always remains within the target range. The blood glucose levels are lower in the GIN therapy group than in the standard therapy group (during surgery, P<0.01; after surgery, P<0.001). In nondiabetic patients receiving GIN therapy (n=19), target glycemia is achieved in 90.1% of the blood glucose measurements during surgery and in 77.8% of the measurements after surgery. In diabetic patients receiving GIN therapy (n=7), target glycemia was achieved in 81.2% of the blood glucose measurements during surgery and in 70.5% of the measurements after surgery. In nondiabetic patients receiving standard therapy (n☐19), target glycemia is achieved in 37.4% of the blood glucose measurements during surgery and in 18.3% of the measurements after surgery. In diabetic patients receiving standard therapy (n=7), target glycemia is achieved in 4.3% of the blood glucose measurements during surgery and in 2.9% of the measurements after surgery. The SD and CV of blood glucose were smaller in the GIN therapy group than in the standard therapy group, especially in nondiabetic patients after surgery (SD, P<0.001; CV, P<0.027). No patients receiving GIN therapy experienced severe hypoglycemia during surgery. One patient receiving GIN therapy experienced hypoglycemia in the intensive care unit after surgery without neurological sequelae.

Conclusions:

GIN therapy effectively provides normoglycemia in patients undergoing liver resection.

Methods

Using computerized randomization tables (with blinded envelopes opened sequentially by study personnel after participants signed the consent form), consenting patients undergoing elective resection of primary or secondary hepatic malignancy (≥2 segments) are randomly assigned to GIN therapy or standard therapy (control group). Exclusion criteria are inability to give written informed consent, severe anemia (hemoglobin<10 g/dL), hemodialysis, or conditions that contraindicated the use of epidural anesthesia.

In diabetic patients, the administration of oral hypoglycaemic drugs is discontinued 24 hours before surgery. If patients received insulin, the daily dose is held the evening before surgery, and subcutaneous insulin is administered using a sliding scale. Arterial blood glucose concentrations are measured using the Accu-Chek® glucose monitor (Roche Diagnostics, Switzerland). Humulin® R regular insulin (Eli Lilly and Company, Indianapolis, Ind.) is administered using the concentration 100 U of insulin in 100 mL normal saline.

In the standard therapy group, blood glucose measurements are performed before the induction of anesthesia, every 30 minutes during surgery, and hourly in the ICU for 24 hours. If the blood glucose was >6.1 mmol/L (110 mg/dL), an insulin infusion of 1 U/h is started. This is then titrated according to the sliding scale shown in Table 1, aiming at a blood glucose between 3.5 and 6.1 mmol/L (63-110 mg/dL) during surgery and 3.5 and 7.9 mmol/L (63-143 mg/dL) after surgery.

In the GIN therapy group, after obtaining a baseline preoperative blood glucose value, 2 U of insulin is administered IV followed by an infusion of 2 mU·kg$^{-1}$·min$^{-1}$. Ten minutes after starting the insulin infusion, and when the blood glucose is <6.1 mmol/L (110 mg/dL), dextrose 20% supplemented with phosphate (30 mmol/L) is administered. In the operating room, blood glucose levels are measured every 15 minutes, and the dextrose infusion rate is adjusted to maintain arterial glycemia between 3.5 and 6.1 mmol/L (63-110 mg/dL). At the end of the surgery, the insulin infusion is decreased to 1 mU·kg$^{-1}$·min$^{-1}$. The blood glucose is measured hourly for 24 hours in the ICU, and the dextrose infusion rate modified by the attending nurse according to the protocol shown in Table 2.

TABLE 36

Standard protocol

| If blood glucose mmol·L$^{-1}$ (mg·dL$^{-1}$) | Action |
|---|---|
| During surgery | |
| >10.0 (180) | Increase insulin infusion by 3 U·h$^{-1}$ |
| 8.0-10.0 (144-180) | Increase insulin infusion by 2 U·h$^{-1}$ |
| 6.2-7.9 (111-143) | Increase insulin infusion by 1 U·h$^{-1}$ |
| 3.5-6.1 (63-110) | Maintain current insulin infusion rate |
| <3.5 (63) | Stop insulin infusion and administer a 10 mL dextrose 20% |
| In the intensive care unit | |
| >10.0 (180) | Increase insulin infusion by 2 U·h$^{-1}$ |
| 8.0-10.0 (144-180) | Increase insulin infusion by 1 U·h$^{-1}$ |
| 3.5-7.9 (63-143) | Maintain current insulin infusion rate |
| <3.5 (63) | Stop insulin infusion and administer a 10 mL dextrose 20% |
| During surgery and in the intensive care unit | |
| Drops to a lower blood glucose range | Maintain current insulin infusion rate |

TABLE 37

GIN protocol in the intensive care unit

| If blood glucose mmol·L$^{-1}$ (mg·dL$^{-1}$) | Action |
|---|---|
| >7.0 (126) | Decrease dextrose infusion rate by half |
| 6.5-7.0 (117-126) | Decrease dextrose infusion rate by 15 mL·h$^{-1}$ |
| 6.2-6.4 (111-116) | Decrease dextrose infusion rate by 10 mL·h$^{-1}$ |
| 5.5-6.1 (99-110) | Decrease dextrose infusion rate by 5 mL·h$^{-1}$ |
| 4.6-5.4 (82-98) | Maintain dextrose infusion rate |
| 4.2-4.5 (75-81) | Increase dextrose infusion rate by 5 mL·h$^{-1}$ |
| 3.5-4.1 (63-74) | Increase dextrose infusion rate by 10 ml·h$^{-1}$ and administer a 10 mL bolus of dextrose 20% |
| <3.5 (63) | Increase dextrose infusion rate by 15 mL·h$^{-1}$ and administer a 20 mL bolus of dextrose 20% |

Severe hyperglycemia is defined as a blood glucose>10.0 mmol/L (180 mg/dL) and moderate hyperglycemia as a blood glucose between 6.2 and 10.0 mmol/L (111-180 mg/dL). Mild hypoglycemia is defined as a blood glucose between 3.5 and 2.2 mmol/L (63-40 mg/dL) and severe hypoglycemia as a blood glucose<2.2 mmol/L (40 mg/dL).

The primary outcome of the study is the relative proportion of normoglycemic measurements in patients receiving GIN therapy and standard therapy. Secondary outcomes are the incidence of severe hypoglycemia, the incidence of hyperglycemia, the average and SD of the blood glucose measurements, and the oscillation in blood glucose defined as the average absolute point-to-point blood glucose variation over time.

For each patient, we calculate the mean and intrasubject SD of blood glucose concentration during and after surgery.

Intrasubject variability is reported as the coefficient of variability (CV=SD/average blood glucose) in each patient.

Patients are operated on by the same surgeon, and anesthesia is provided by 1 of the 3 experienced staff anesthesiologists. All patients receive general anesthesia combined with epidural anesthesia followed by postoperative epidural analgesia. General anesthesia is induced using propofol and fentanyl and maintained with nitrous oxide and desflurane. Rocuronium is used to provide muscle relaxation. The epidural catheter is inserted before induction of anesthesia at a thoracic vertebral level between T6 and T9. Bupivacaine 0.5% (10-15 mL) is injected to produce a confirmed bilateral, segmental sensory block from T4 to L3. Additional 0.25% bupivacaine (5-mL) boluses are injected via the epidural catheter every 30 minutes during surgery. Postoperatively, epidural bupivacaine 0.1%, supplemented with 2 µg/mL fentanyl, is administered continuously at a rate of 8 to 15 mL/h and maintained throughout the study period. Serum potassium levels in the ICU are measured every 4 hours.

The data are presented as means±SD or medians (with interquartile ranges), unless otherwise indicated. Continuous biometric and surgical data between standard and GIN therapy groups are analyzed by the Student t test or the Mann-Whitney U test. $\chi^2$ was used for categorical variables. Mean blood glucose values, SD, and CV of blood glucose between 2 study groups are compared using Student t test with adjustment for unequal variances (Welch test). $\chi^2$ tests or Fisher exact tests are applied to compare proportions of each blood glucose range. Blood glucose levels are compared using 2-way analysis of variance with repeated measures across time and a comparison across groups. We consider 2-sided P values<0.05 to be statistically significant.

The number of patients needed is calculated based on the assumption that the percentage of normoglycemic measurements is at least 80% in the GIN therapy group and <40% in the standard therapy group. To achieve a power level of 80%, with an α error of 5% and β error of 20%, 26 patients are needed in each group. All statistical analyses are performed using SPSS17.0 for Windows (SPSS, Chicago, Ill.) and PASS 2008 (NCSS, Kaysville, Utah).

Results

Figure 18:
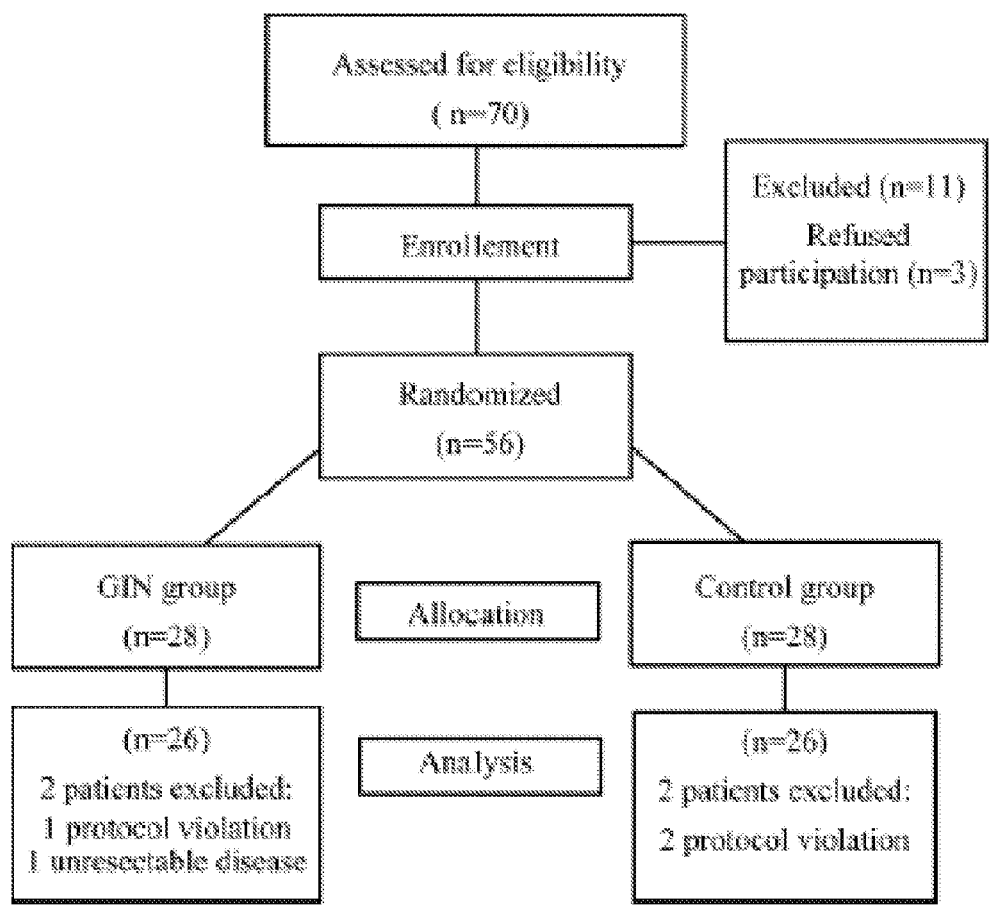
FIG. 18 illustrates Patient distribution. Seventy patients are assessed for eligibility for the study and 56 patients are randomized. After randomization, 4 patients are excluded, 1 for unresectable disease and 3 for protocol violations.

Seventy patients are assessed for eligibility and 56 patients are randomized. After randomization, 4 patients are excluded, 1 for unresectable disease and 3 for protocol violations (FIG. 18).

There are no significant differences in the characteristics of the 2 study groups (Table 38). Seven patients in each group have Type 2 diabetes mellitus. A total of 268 plasma potassium levels and 1719 blood glucose levels are recorded, 422 during surgery and 1297 in the ICU.

TABLE 38

Biometric and surgical data

| | GIN | Standard |
|---|---|---|
| Patients (n) | 26 | 26 |
| Age (y) | 58.7 ± 12.5 | 56.6 ± 13.7 |
| Gender (M/F) | 14/12 | 14/12 |
| Weight (kg) | 70.4 ± 10.5 | 72.9 ± 10.3 |
| Height (m) | 1.65 ± 0.08 | 1.69 ± 0.06 |
| Body mass index (kg · m$^{-2}$) | 25.9 ± 3.0 | 25.6 ± 3.7 |
| Diabetes, n (%) | 7 (27) | 7 (27) |
| Albumin (g · dL$^{-1}$) | 3.6 ± 0.8 | 3.7 ± 0.9 |
| Total billrubin (mg · dL$^{-1}$) | 2.0 ± 2.6 | 1.9 ± 2.1 |
| Platelet (10$^4$ · µL$^{-1}$) | 254 ± 97 | 233 ± 91 |
| INR | 1.1 ± 0.2 | 1.1 ± 0.3 |
| Duration of surgery (min) | 183 (163-223) | 188 (165-218) |
| Number of segments resected | 3.5 ± 1.0 | 3.6 ± 0.8 |
| Estimated blood loss (mL) | 1150 (850-2000) | 1100 (1000-1925) |
| Blood transfusion, n (%) | 21 (81) | 22 (85) |
| Blood transfusion (unit) | 4.4 ± 3.7 | 4.6 ± 3.8 |

Data are expressed as mean ± SD. n (%), or median (interquartile ranges).
There were no significant differences between the 2 study groups.
INR = international normalized ratio.

Figure 19:
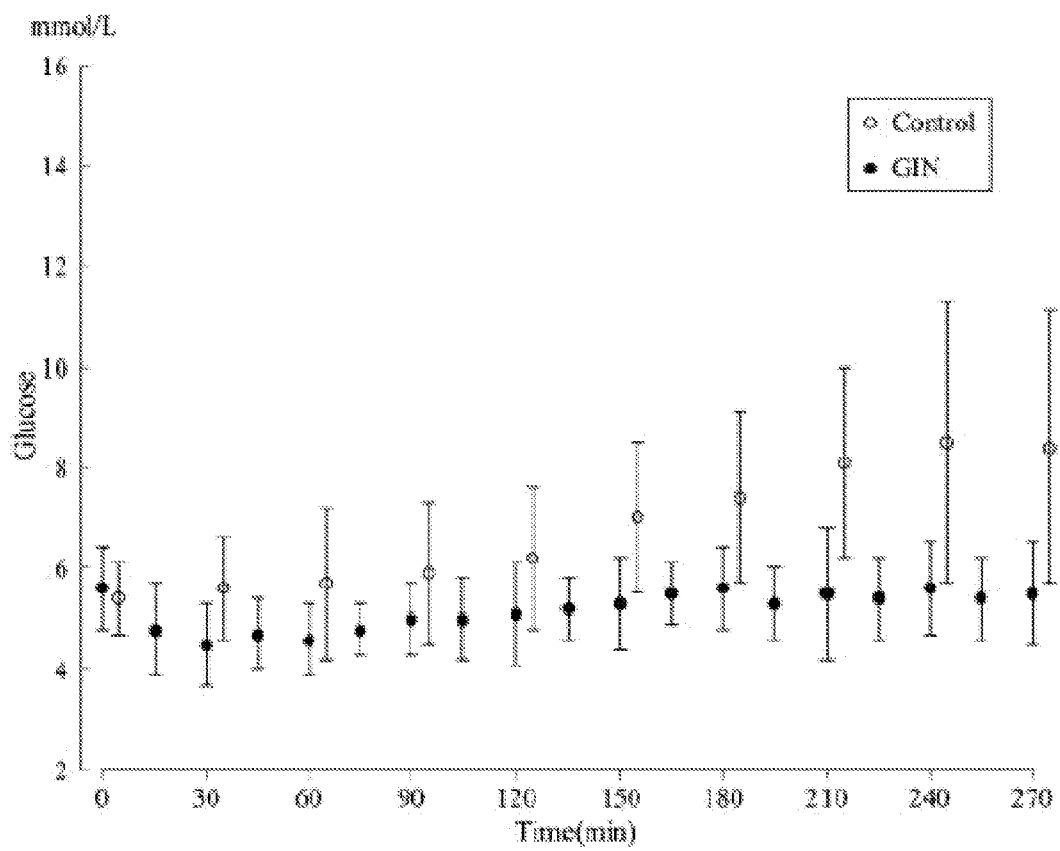
FIG. 19 illustrates time dependence of intraoperative blood glucose concentrations in nondiabetic patients. Data are mean blood glucose concentration±SD (mmol/L). In the standard therapy group, the mean blood glucose gradually increased (P=0.029). The mean blood glucose in the GIN therapy group always remained within the normoglycemic target range (3.5-6.1 mmol/L [63-110 mg/dL]). The blood glucose levels are lower in the GIN therapy group than in the standard therapy group (P=0.003).
Figure 20:
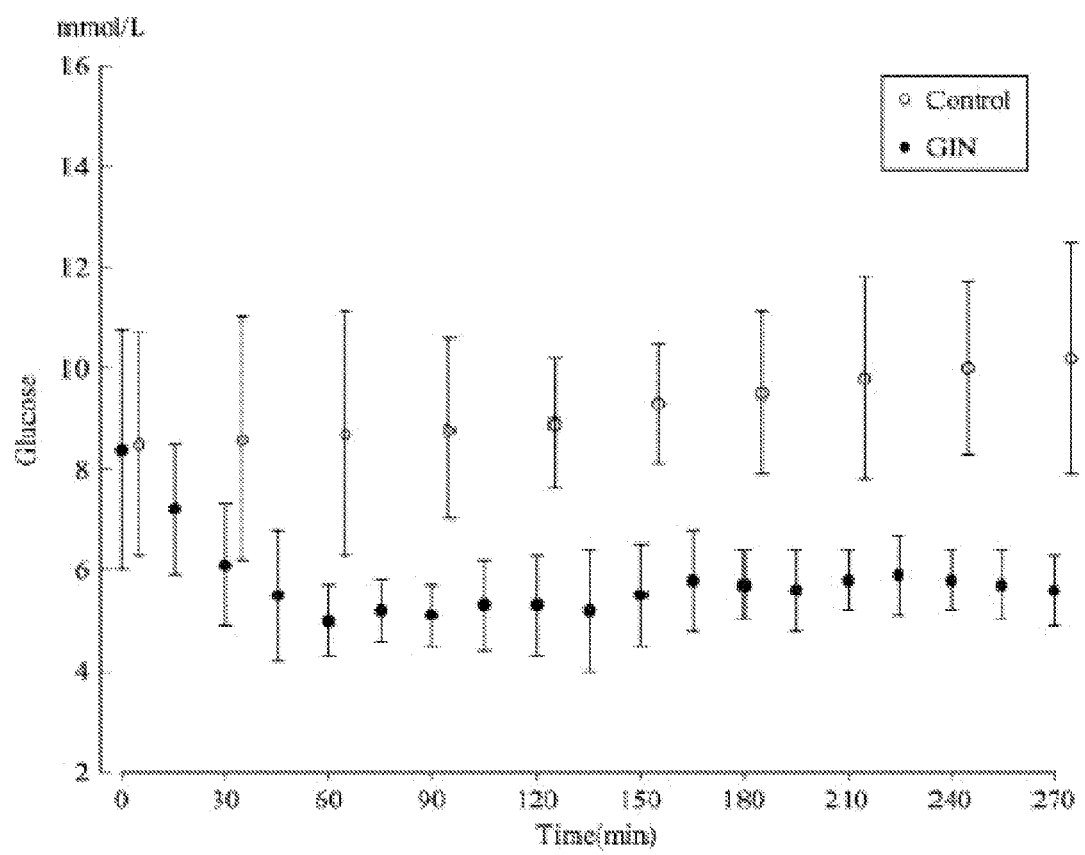
FIG. 20 illustrates Time dependence of intraoperative blood glucose concentrations in diabetic patients. Data are mean blood glucose concentration±SD (mmol/L). In the standard therapy group, glycemia slightly increased to 10.0 mmol/L (180 mg/dL) toward the end of surgery (P=0.102). The blood glucose levels were lower in the GIN therapy group than in the standard therapy group (P=0.002).
Figure 21:
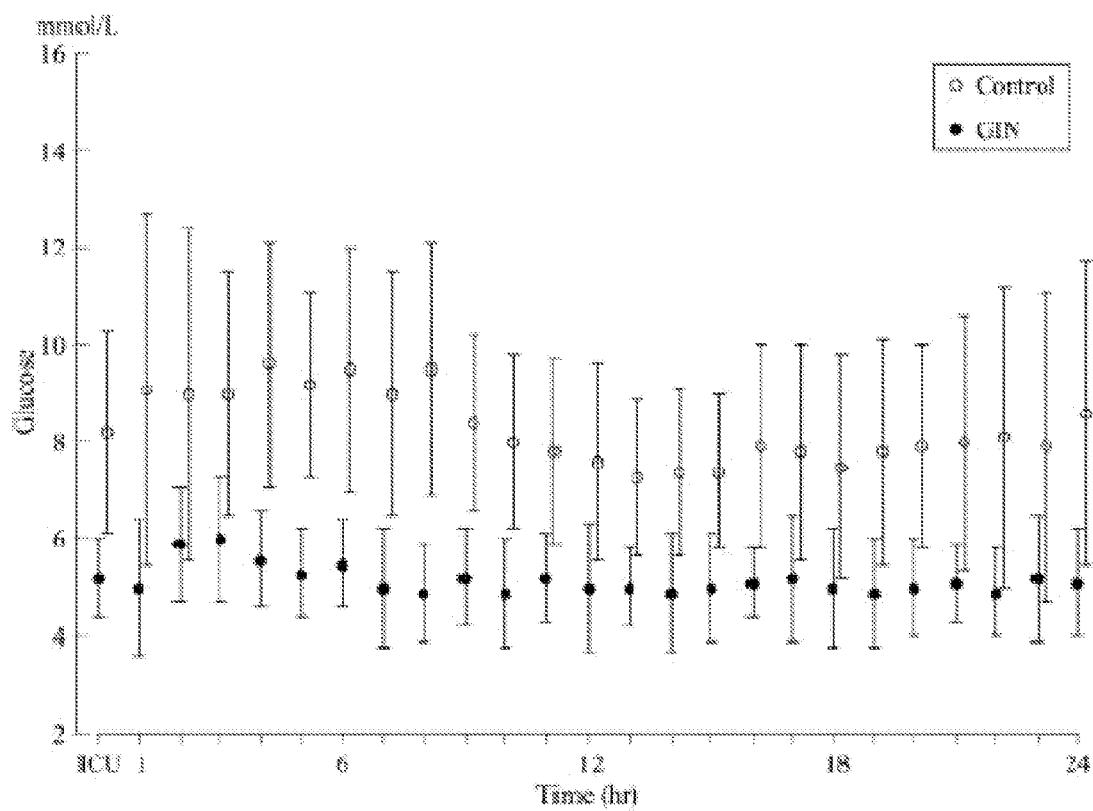
FIG. 21 illustrates time dependence of postoperative blood glucose concentrations in nondiabetic patients. Data are mean blood glucose concentration±SD (mmol/L). In the standard therapy group, glycemia remained between 7.0 and 10.0 mmol/L (126-180 mg/dL). The mean blood glucose in the GIN therapy group always remained within the normoglycemic target range (3.5-6.1 mmol/L [63-110 mg/dL]). The blood glucose levels are lower in the GIN therapy group than in the standard therapy group (P<0.001). ICU=intensive care unit; ICU 1, 6, 12, 18, 24 hr=1, 6, 12, 18, 24 hours after the patient's arrival in the ICU.
Figure 22:
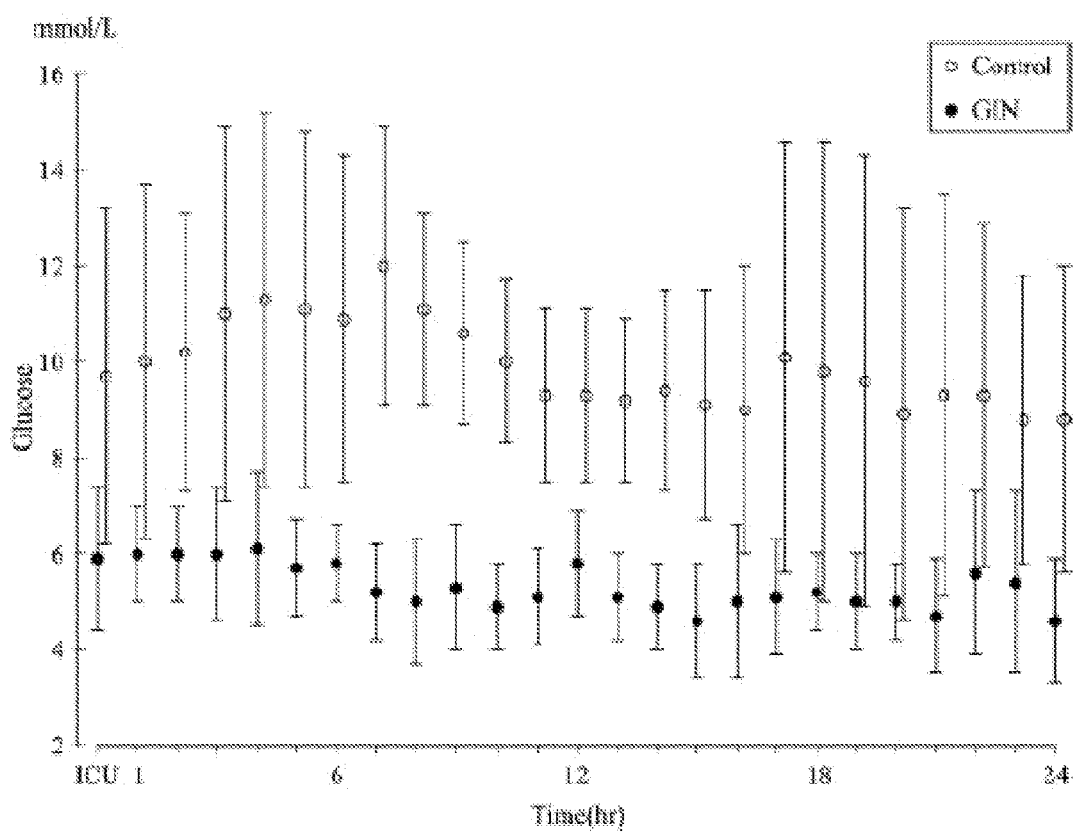
FIG. 22 illustrates time dependence of postoperative blood glucose concentrations in diabetic patients. Data are mean blood glucose concentration±SD (mmol/L). In the standard therapy group, glycemia remained between 9.0 and 12.0 mmol/L (162-216 mg/dL). The mean blood glucose in the GIN therapy group always remained within the normoglycemic target range (3.5-6.1 mmol/L [63-110 mg/dL]). The blood glucose levels were lower in the GIN therapy group than in the standard therapy group (P<0.001). ICU=intensive care unit; ICU 1, 6, 12, 18, 24 hr=1, 6, 12, 18, 24 hours after the patient's arrival in the ICU.

In the standard therapy group, the mean blood glucose gradually increases during surgery in nondiabetic patients and remains increased in the ICU at approximately 9.0 mmol/L (162 mg/dL (P=0.029) (FIGS. 19 and 21). Diabetic patients show a mean blood glucose concentration>8.0 mmol/L (144 mg/dL) before surgery. Glycemia slightly increases to 10.0 mmol/L (180 mg/dL) toward the end of surgery (P=0.102) and remains between 9.0 and 12.0 mmol/L (162-216 mg/dL) in the ICU (FIGS. 20 and 22). Target glycemia is achieved in 37.4% of measurements during surgery and 18.3% after surgery in the absence of diabetes mellitus (P<0.001). In diabetic patients, 4.3% of values are within target during surgery and 2.9% in the ICU (P=0.953) (Table 39).

The mean blood glucose in the GIN therapy group always remained within the normoglycemic target range. The blood glucose levels were lower in the GIN therapy group than in the standard therapy group during and after surgery (during surgery, P=0.003 in nondiabetic patients [FIG. 19], P=0.002 in diabetic patients [FIG. 20]; after surgery, P<0.001 [FIGS. 21 and 22]). In nondiabetic patients receiving GIN therapy, target glycemia is achieved in 90.1% of blood glucose measurements during surgery and in 77.8% of blood glucose measurements after surgery (P<0.001). In diabetic patients, target glycemia is achieved in 81.2% of blood glucose measurements during surgery and in 70.5% of blood glucose measurements postoperatively (P=0.071) (Table 37). In the GIN therapy group, nondiabetic patients are more likely to achieve target glycemia than diabetic patients (during surgery, P=0.048; after surgery, P=0.054).

The oscillation of blood glucose is smaller in the GIN therapy group compared with the standard therapy group (SD, P=0.046 in nondiabetic patients; P=0.050 in diabetic patients during surgery). This is especially pronounced in nondiabetic patients after surgery (SD, P<0.001; CV, P=0.027).

No patient receiving GIN therapy experienced severe hypoglycemia (blood glucose<2.2 mmol/L [40 mg/dL]) during surgery. One patient in the GIN therapy group experienced hypoglycemia in the ICU after surgery (3.8% of patients). Mild hypoglycaemia (blood glucose between 2.2 and 3.5 mmol/L [40-63 mg/dL]) occurred in 1.1% of measurements during surgery (7.7% of patients) and 3.8% of measurements (30.8% of patients) in the ICU (combined data from both groups). In diabetic patients, the incidence of mild hypoglycemia after surgery is 2.9% (11.5% of patients) (Table 39). Mild hypoglycemia occurs more frequently after surgery in the GIN therapy group than the standard therapy group (during surgery, P=0.266; after surgery, P=0.001). There are no neurological sequelae from the episodes of hypoglycemia.

Plasma potassium levels were lower in the GIN therapy group compares with the standard therapy group in the ICU (P<0.001). Mild hypokalemia, i.e., $K^+$<3.4 mmol/L, occurred in 10.4% of measurements in the GIN therapy group (23.1% of patients) and 3.7% of measurements in the standard therapy group (11.5% of patients) (P=0.032) (Table 40).

TABLE 39

Glucose control during and after surgery

| | GIN | | Standard | |
|---|---|---|---|---|
| | Non-DM | *DM | Non-DM | DM |
| During surgery | | | | |
| N | 19 | 7 | 19 | 7 |
| Blood glucose (mmol · $L^{-1}$) | 5.2 ± 0.7 | 5.3 ± 0.9 | 7.2 ± 1.7* | 9.2 ± 1.8* |
| SD glucose (mmol · $L^{-1}$) | 0.6 ± 0.3 | 0.6 ± 0.3 | 0.9 ± 0.6* | 1.2 ± 0.6 |
| CV glucose (%) | 11.8 ± 4.9 | 11.1 ± 5.3 | 12.9 ± 7.3 | 13.2 ± 8.1 |
| Blood glucose range | 2.7-7.4 | 3.5-7.5 | 4.6-12.0 | 5.9-12.9 |
| Measurements (n) | 181 | 80 | 115 | 46 |
| <2.2 mmol · $L^{-1}$ | 0 (0%) | 0 (0%) | 0 (0%) | 0 (0%) |
| 2.2-3.4 mmol · $L^{-1}$ | 2 (1.1%) | 0 (0%) | 0 (0%) | 0 (0%) |
| 3.5-6.1 mmol · $L^{-1}$ | 163 (90.1%) | 65 (81.2%) | 43 (37.4%)* | 2 (4.3%)* |
| 6.2-7.9 mmol · $L^{-1}$ | 16 (8.8%) | 15 (18.8%) | 30 (26.1%)* | 10 (21.7%) |
| 8.0-10.0 mmol · $L^{-1}$ | 0 (0%) | 0 (0%) | 38 (33.0%)* | 21 (45.7%)* |
| >10 mmol · $L^{-1}$ | 0 (0%) | 0 (0%) | 4 (3.5%)* | 13 (28.3%)* |
| Intensive care unit | | | | |
| N | 19 | 7 | 19 | 7 |
| Blood glucose (mmol · $L^{-1}$) | 5.5 ± 1.1 | 5.6 ± 1.3 | 8.3 ± 2.5* | 10.2 ± 3.4* |
| SD glucose (mmol · $L^{-1}$) | 1.1 ± 0.3 | 1.2 ± 0.4 | 2.2 ± 0.9* | 2.6 ± 1.6* |
| CV glucose (%) | 20.6 ± 4.2 | 21.1 ± 4.5 | 26.1 ± 9.6* | 25.1 ± 11.1 |
| Blood glucose range | 2.0-8.7 | 2.3-9.7 | 4.0-20.3 | 5.3-24.4 |
| Measurements (n) | 474 | 173 | 475 | 175 |
| <2.2 mmol · $L^{-1}$ | 1 (0.2%) | 0 (0%) | 0 (0%) | 0 (0%) |
| 2.2-3.4 mmol · $L^{-1}$ | 18 (3.8%) | 5 (2.9%) | 0 (0%)* | 0 (0%)* |
| 3.5-6.1 mmol · $L^{-1}$ | 369 (77.8%) | 122 (70.5%) | 87 (18.3%)* | 5 (2.9%)* |
| 6.2-7.9 mmol · $L^{-1}$ | 80 (16.9%) | 42 (24.3%) | 144 (30.3%)* | 34 (19.4%) |
| 8.0-10.0 mmol · $L^{-1}$ | 6 (1.3%) | 4 (2.3%) | 152 (32.0%)* | 72 (41.1%)* |
| >10 mmol · $L^{-1}$ | 0 (0%) | 0 (0%) | 92 (19.4%)* | 64 (36.6%)* |

Data are expressed as mean ± SD. n (%), or range (minimum-maximum).
DM = diabetes mellitus.
*P < 0.05 compared with GIN group.

TABLE 40

Plasma potassium levels in the intensive care unit

| | GIN | Standard |
|---|---|---|
| Potassium (mmol $L^{-1}$) | 3.9 ± 0.3 | 4.3 ± 0.5* |
| Potassium range | 3.2-4.7 | 3.3-5.6 |
| Measurements (n) | 134 | 134 |
| Hyperkalemia (5.1-6.3 mmol · $L^{-1}$) | 0 | 5 (3.7%) |
| Normal range (3.5-4.5 mmol · $L^{-1}$) | 117 (87.3%) | 86 (64.2%)* |
| Mild hypokalemia (<3.4 mmol · $L^{-1}$) | 14 (10.4%) | 5 (3.7%)* |

Data are expressed as mean ± SD. n (%), or range (minimum-maximum).
*P < 0.05 compared with GIN group.

Discussion

The results of this study demonstrate that major liver resection is associated with a moderate to severe hyperglycaemic response and that GIN therapy effectively provides normoglycemia in this patient population with little risk of hypoglycemia. Although the clinical relevance of hyperglycemia in cardiac surgery and critical care is recognized, little information is available on glucose metabolism in patients undergoing major upper abdominal procedures.

In the standard therapy group, using a traditional insulin sliding scale prompting insulin therapy at a blood glucose exceeding 6.1 mmol/L (110 mg/dL) during surgery and 7.9 mmol/L (143 mg/dL) after surgery, we obtained moderate glycemic control with mean blood glucose values of 7.2 mmol/L (130 mg/dL) intraoperatively and 8.3 mmol/L (150 mg/dL) postoperatively. Not surprisingly, in the standard therapy group, glycemic control in diabetic patients is worse as reflected by mean blood glucose values of 9.2 mmol/L (166 mg/dL) intraoperatively and 10.2 mmol/L (184 mg/dL) postoperatively. A large proportion of measurements show values >6.1 mmol/L (110 mg/dL) in nondiabetic patients, whereas in diabetic patients, the vast majority of values are outside the target range.

All patients in this protocol received intraoperative epidural anesthesia followed by postoperative epidural analgesia. Because neuraxial blockade significantly attenuates the hyperglycemic response to abdominal surgery, it is assumed that the lack of epidural anesthesia would have further impaired glucose homeostasis. A recent study on glycemic control in nondiabetic patients after hepatectomies with an unspecified type of anesthesia and analgesia reported average glycemia values>12.0 mmol□L□1 (216 mg/dL) within the first 10 hours after surgery.

Strict maintenance of normoglycemia by intensive insulin therapy has been shown to reduce mortality and to attenuate liver, kidney, and endothelial dysfunction in critically ill patients. Insulin has a variety of nonmetabolic, pharmacological properties with potential clinical benefit. Exploiting these antiinflammatory, antiaggregatory, and inotropic effects during critical illness requires large amounts of insulin and normal blood glucose levels. Unfortunately, in perioperative medicine, the fear of hypoglycaemia has led to insulin therapies that are neither high dose nor effective. Current insulin administration regimens are reactive and permit hyperglycemia to occur before treatment can be initiated. The only randomized controlled trial focused on glycemic control during the intraoperative period compared continuous insulin infusion with traditional treatment; the continuous insulin infusion group did not have good glucose control or improved outcomes. This observation lends further support to the contention that, independent of the provider of insulin therapy (computer, physician, or nurse), optimal glucose control cannot be achieved by occasional blood glucose measurements followed by adjustments of the insulin infusion. Conversely, the GIN therapy concept, as outlined herein, modifies the rate of dextrose infusion while keeping the insulin infusion constant throughout the perioperative period. At a rate of 2 $mU \cdot kg^{-1} \cdot min^{-1}$, endogenous glucose production is totally suppressed, and the plasma glucose level is maintained constant by matching the glucose infusion rate with the glucose utilization rate. Traditional insulin sliding scales, however, despite a long history in medicine, are not effective.

Besides the potential clinical advantages of insulin administration and normoglycemia, the administration of dextrose as an essential part of GIN therapy might add benefits, specifically for patients undergoing major liver resections. Animal studies suggest that the hepatic glycogen content is a key regulator of liver function and that glycogen depletion, a mandatory consequence of prolonged preoperative fasting, may have a negative impact on liver homeostasis and integrity. Patients receiving GIN therapy in this study show mean blood glucose values that are always within the normal range. The percentage of measured glucose values within the target range was higher than in previous reports. Using a technique similar to ours, but administering a lower dose of insulin (1.66 $mU \cdot kg^{-1} \cdot min^{-1}$) and performing less-frequent blood sampling during surgery, Visser et al. reported a comparable success rate of 85% in a small group of 10 nondiabetic patients undergoing cardiac surgery.

The continuous blood glucose monitoring and closedloop insulin administration system (STG-22™, Nikkiso, Tokyo, Japan) have also been studied in patients undergoing hepatic resection. Although the "artificial pancreas" was reported to be effective and safe, the blood glucose level only stabilized 12 hours after surgery and the mean blood glucose level remained above the defined target range of 5.0 to 6.1 mmol/L (90-110 mg/dL). Therefore, even with continuous blood glucose monitoring, the artificial pancreas did not effectively maintain normoglycemia, likely because the complex perioperative physiologic changes imposed by fluid shifts and surgery-induced insulin resistance are not captured in the algorithms designed for routine glucose management. Several closed-loop systems 30 and software programs have also been used and studied for glucose control in the ICU, but no device has been effective in maintaining normoglycemia.

In our study, severe hypoglycemia, the most feared complication of intensive insulin therapy, is rarely induced. Patients receiving GIN therapy show no severe hypoglycemic event (blood glucose<2.2 mmol/L [40 mg/dL] during surgery and only 1 episode in the ICU without any neurological sequelae. The prevalence of hypoglycaemia varies widely with intensive insulin therapy and has been reported to occur in 0% to 94% of patients.

The investigators from Leuven, where the international interest in intensive insulin therapy originated, were unable to prevent severe hypoglycemia in 18.7% of their medical ICU population. The VISEP trial, using the original Leuven protocol, in patients with sepsis, was prematurely terminated because of a 17% incidence of severe hypoglycemia. The GLUCONTROL study was also stopped before completion because the target of 4.4 to 6.1 mmol/L (80-110 mg/dL) was not achieved and the risk of hypoglycemia was unacceptably high. Most recently in a mixed surgical-medical population, intensive insulin therapy was associated with a 6.8% incidence of severe hypoglycemia.

There is evidence to suggest that the variability of glycemia, rather than the absolute blood glucose value, influences outcome. It has been proposed that fluctuations in glycemia trigger oxidative stress to a greater degree than sustained hyperglycemia. Therefore, strict glycemic control may improve outcome not only by maintaining normoglycemia but also by mitigating the extreme swings that occur during, and especially after, surgery. Data obtained from critically ill patients showed that survivors experienced significantly less blood glucose variability than nonsurvivors (CV of glucose in survivors: 20%±12%; in nonsurvivors: 26%±13%). The SD of blood glucose was an independent predictor of ICU mortality and a stronger predictor of survival than the mean blood glucose concentration. In this study, during the postoperative period, SD and CV of blood glucose in the GIN therapy group are similar to the values of the survivor group as reported previously. In our standard therapy group, SD and CV values are similar to those documented in nonsurvivors.

In the present study, during surgery, blood glucose sampling is more frequent in the GIN therapy group. This difference in the blood sampling frequency may seem to be unfair for comparison between 2 groups. However, the performance of both protocols is considered to arrive at a sampling frequency. In the GIN therapy group, blood is sampled every 15 minutes because it takes about that amount of time for infused dextrose to distribute. Another reason is safety, i.e., the potential for hypoglycemia when high-dose insulin is given IV. In the standard therapy group, blood was sampled every 30 minutes, reflecting the slower change in blood glucose concentration in response to changes in insulin infusion rate. Indeed, more rapid sampling might lead to inappropriately high insulin infusion rates because of titration before reaching the peak effect of the last rate adjustment.

Transfusion of blood products that contain nontrivial amounts of glucose also complicates glucose control. Because GIN therapy patients are already receiving dextrose when transfusions are administered, the blood glucose is easily maintained constant by reducing the dextrose infusion rate. With standard therapy, the effects of changing the insulin infusion rate are too slow to counteract the glucose load from transfused blood products, leading to hyperglycemia that is then corrected over hours.

The lower edge of the blood glucose target (of 3.5 mmol/L [63 mg/dL]) in this protocol is lower than in other insulin trials, which typically aim at blood glucose levels>4.0 mmol/L (72 mg/dL) or 4.4 mmol/L (80 mg/dL). The circulating concentration of glucose in the human body, contrary to other metabolic substrates such as fatty acids or amino acids, is controlled within a narrow range. Although there is no absolute definition of normoglycemia, healthy individuals maintain a blood glucose between 3.6 and 7.8 mmol/L (65-140 mg/dL) across physiologic states (fasting, feeding, and exercise). For these reasons, we consider 3.3 to 3.9 mmol/L (60-70 mg/dL) to be normal values.

Routine use of GIN therapy is labor intensive because of the high frequency of blood glucose measurements necessary for the safe conduct of the protocol.

In conclusion, we demonstrated that the perioperative use of GIN therapy effectively provides normoglycemia in diabetic and nondiabetic patients undergoing major liver resection.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of improving liver function comprising: administering to a subject in need thereof prior to, during and after a liver surgery a high dose of insulin and a dose of dextrose sufficient to avoid hypoglycemia for a time sufficient for improving organ function, wherein a starting blood glucose level of said subject prior to said administering is from about 4 mmol/L to about 6 mmol/L, wherein said administering is for maintaining a target blood glucose level of said subject from about 3.5 mmol/L to less than about 8.5 mmol/L, wherein said method is for the treatment of a liver requiring surgical resection, a resected liver, a liver transplant, or a liver condition caused by a cancer, and wherein a rate of administration of said high dose of insulin is from about 1 mU/kg/min to about 5 mU/kg/min.

2. The method as claimed in claim 1, wherein said dose of dextrose is provided from a 20% w/v dextrose solution, and a rate of administration of said dose of dextrose is adjusted to maintain normoglycemia.

3. The method as claimed in claim 1, wherein said rate of administration of said dose of dextrose is 40 ml/hour.

4. The method as claimed in claim 1, wherein said time sufficient is about 8 hours.

5. The method as claimed in claim 1, wherein said time sufficient is about 8 hours, twice a week.

6. The method as claimed in claim 1, wherein said time sufficient is about 8 hours, twice a week for 24 weeks.

7. The method as claimed in claim 1, wherein said target blood sugar level is from about 4.6 mmol/L to about 5.5 mmol/L.

8. The method as claimed in claim 7, wherein said target blood glucose level is measured 10 minutes after starting of said administering.

9. The method as claimed in claim 8, wherein said target blood glucose level is measured every 60 minutes until the end of said administering.

10. The method as claimed in claim 1, wherein said method is for the treatment of a condition chosen from a liver requiring surgical resection, a resected liver, liver transplant, and a liver condition.

11. The method as claimed in claim 10, wherein said cancer is a cancer of the liver, a cancer that originated in the colorectum and which then metastasized to the liver, a cancer that originated in the breast and which then metastasized to the liver, or a combination thereof.

12. The method as claimed in claim 10, wherein said method is at least one of a pre-operative treatment, a peri-operative treatment, a post-operative treatment, a long term intermittent treatment, a long term continuous treatment, or combinations thereof.

* * * * *

UNITED STATES PATENT AND TRADEMARK OFFICE
CERTIFICATE OF CORRECTION

PATENT NO. : 8,592,372 B2  
APPLICATION NO. : 13/171597  
DATED : November 26, 2013  
INVENTOR(S) : Thomas P. S. Schricker et al.

Page 1 of 1

It is certified that error appears in the above-identified patent and that said Letters Patent is hereby corrected as shown below:

On the title page item (75),
The second inventor, named "Ralph Latterman" in the patent, should appear as "Ralph Lattermann".

Signed and Sealed this
Thirteenth Day of May, 2014

Michelle K. Lee
*Deputy Director of the United States Patent and Trademark Office*